United States Patent
Dekany et al.

(10) Patent No.: US 9,234,225 B2
(45) Date of Patent: Jan. 12, 2016

(54) METHOD FOR GENERATING HUMAN MILK OLIGOSACCHARIDES (HMOS) OR PRECURSORS THEREOF

(75) Inventors: Gyula Dekany, Sinnamon Park (AU); Elise Champion, Toulouse (FR); Andreas Schroven, Barssel (DE); Markus Hederos, Svedala (SE)

(73) Assignee: GLYCOM A/S, KGS. Lyngby (DK)

( * ) Notice: Subject to any disclaimer, the term of this patent is extended or adjusted under 35 U.S.C. 154(b) by 73 days.

(21) Appl. No.: 14/117,348

(22) PCT Filed: May 14, 2012

(86) PCT No.: PCT/IB2012/052400
§ 371 (c)(1),
(2), (4) Date: Dec. 19, 2013

(87) PCT Pub. No.: WO2012/156897
PCT Pub. Date: Nov. 22, 2012

(65) Prior Publication Data
US 2014/0234912 A1 Aug. 21, 2014

(30) Foreign Application Priority Data

May 13, 2011 (EP) .................... 11166135
Mar. 19, 2012 (WO) .................. PCT/IB2012/051314

(51) Int. Cl.
| | | |
|---|---|---|
| C12P 19/04 | (2006.01) |
| C12P 19/12 | (2006.01) |
| C12P 19/14 | (2006.01) |
| C07H 17/02 | (2006.01) |
| C07H 17/04 | (2006.01) |
| C07H 9/06 | (2006.01) |
| C08B 37/00 | (2006.01) |
| A23L 1/29 | (2006.01) |
| C12P 19/18 | (2006.01) |
| C07H 17/075 | (2006.01) |
| C07H 19/01 | (2006.01) |

(52) U.S. Cl.
CPC ............. *C12P 19/14* (2013.01); *A23L 1/296* (2013.01); *C07H 9/06* (2013.01); *C07H 17/02* (2013.01); *C07H 17/04* (2013.01); *C07H 17/075* (2013.01); *C07H 19/01* (2013.01); *C08B 37/006* (2013.01); *C12P 19/04* (2013.01); *C12P 19/12* (2013.01); *C12P 19/18* (2013.01); *C12Y 302/0114* (2013.01)

(58) Field of Classification Search
None
See application file for complete search history.

(56) References Cited

FOREIGN PATENT DOCUMENTS

| WO | 96/32492 | 10/1996 |
| WO | WO 9840512 A2 * | 9/1998 |
| WO | 99/08511 | 2/1999 |
| WO | 03/016469 | 2/2003 |
| WO | 2005/055944 | 6/2005 |
| WO | 2011/100980 | 8/2011 |
| WO | 2012/007585 | 1/2012 |
| WO | 2012/007588 | 1/2012 |
| WO | 2012/127410 | 9/2012 |

OTHER PUBLICATIONS

European Search Report and Written Opinion dated Sep. 4, 2014 in corresponding European Patent Application No. 12 78 5846.
Adriane R. Todeschini et al., "Trans-sialidase from Trypanosoma cruzi catalyzes sialoside hydrolysis with retention of configuration," Glycobiology, vol. 10, No. 2, pp. 213-221 (2000).
Xi Chen et al., "Large-scale enzymatic synthesis of oligosaccharides," Current Opinion in Drug Discovery & Development, vol. 3, No. 6, pp. 756-763 (2000).
International Search Report and Written Opinion dated Aug. 10, 2012 in International Patent Application No. PCT/IB2012/052400.
Annie Malleron et al., "Chemoenzymatic synthesis of the 3-sulfated Lewis pentasaccharide," Carbohydrate Research, vol. 341, pp. 29-34 (2006).
Zsuzsanna Marton et al., "Engineering of glucoside acceptors for the regioselective synthesis of β-(1 → 3)-disaccharides with glycosynthases," Carbohydrate Research, vol. 343, pp. 2939-2946 (2008).
Rosalia Agusti et al., "Lactose derivatives are inhibitors of *Trypanosoma cruzi* trans-sialidase activity toward conventional substrates in vitro and in vivo." Glycobiology, vol. 14, No. 7, pp. 659-670 (2004).
Takeomi Murata et al., "Facile enzymatic conversion of lactose into lacto-N-tetraose and lacto-N-neotetraose," Glycoconjugate Journal, vol. 16, pp. 189-195 (1999).
Mutsumi Sano et al., "Purification and Characterization of an Enzyme Releasing Lacto-N-biose from Oligosaccharides with Type 1 Chain," Journal of Biological Chemistry, vol. 268, No. 25, pp. 18560-18566 (Issue of Sep. 5, 1993).
Gastón Paris et al., "A Sialidase Mutant Displaying trans-Sialidase Activity," J. Mol. Biol., vol. 345, pp. 923-934 (2005).
George Oyamo Osanjo et al., "Engineering the functional fitness of transglycosidases and glycosynthases by directed evolution," Afr. J. Biotechnol., vol. 10, No. 10, pp. 1727-1735 (Mar. 7, 2011).
Jun Wada et al., "*Bifidobacterium bifidum* Lacto-N-Biosidase, a Critical Enzyme for the Degradation of Human Milk Oligosaccharides with a Type 1 Structure," Appl. Environ. Microbiol., vol. 74, No. 13, pp. 3996-4004 (Jul. 2008).
David A. Sela et al., "*Bifidobacterium longum* subsp. Infantis ATCC 15697 α-Fucosidases Are Active on Fucosylated Human Milk Oligosaccharides," Appl. Environ. Microbiol., vol. 78, No. 3, pp. 795-803 (Feb. 2012).

(Continued)

*Primary Examiner* — Layla Bland
(74) *Attorney, Agent, or Firm* — Pillsbury Winthrop Shaw Pittman LLP

(57) ABSTRACT

A method for generating human milk oligosaccharides (HMOs) or precursors thereof, compounds obtainable by the method, and uses and compositions involving such compounds. The method comprising the steps of a) providing at least one donor selected from the group of compounds of any of formulae 5 to 10, b) providing at least one acceptor from a group of lactose, LNT, LNnT and derivatives thereof, c) providing at least one enzyme comprising a transglycosidase activity and/or a glycosynthase activity, d) preparing a mixture of the at least one donor, at least one acceptor and at least one enzyme provided in steps a), b) and c); and e) incubating the mixture prepared according to step d).

25 Claims, 3 Drawing Sheets

(56) References Cited

OTHER PUBLICATIONS

George Osanjo et al. "Directed Evolution of the α-L-Fucosidase from *Thermotoga maritima* into an α-L-Transfucosidase," Biochemistry, vol. 46, No. 4, pp. 1022-1033 (2007).

Shin-ichiro Shoda et al., "Chemo-enzymatic synthesis of novel oligo-N-acetyllactosamine derivatives having a β(1-4)-β(1-6) repeating unit by using transition state analogue substrate," Cellulose, vol. 13, pp. 477-484 (2006).

Jun Wada et al., "1,2-α-L-Fucosynthase: A glycosynthase derived from an inverting α-glycosidase with an unusual reaction mechanism," FEBS Letters, vol. 582, pp. 3739-3743 (2008).

Haruko Sakurama et al., "1,3-1,4-α-L-Fucosynthase That Specifically Introduces Lewis a/x Antigens into Type-1/2 Chains," Journal of Biological Chemistry, vol. 287, No. 20, pp. 16709-16719 (May 11, 2012).

Suddham Singh et al., "Synthesis of sialyloligosaccharides using the trans-sialidase from *Trypanosoma cruzi*: novel branched and di-sialylated products from digalactoside acceptors," Chem. Commun., pp. 1013-1014 (2000).

Dirk Schmidt et al., "Sialidase-catalyzed transsialylation using polymer-supported solution-phase techniques," Chem. Commun., pp. 1919-1920 (2000).

Takeomi Murata et al., "Enzymatic synthesis of α-L-fucosyl-N-acetyllactosamines and 3'-O-α-L-fucosyllactose utilizing α-L-fucosidases," Carbohydrate Research, vol. 320, pp. 192-199 (1999).

David S. Newburg et al., "Carboyhydrates in Milks: Analysis, Quantities, and Significance," Handbook of Milk Composition, Chapter 4, pp. 273-349 (1995).

Chris J. Hamilton, "Enzymes in preparative mono- and oligo-saccharide synthesis," Nat. Prod. Rep., vol. 21, pp. 365-385 (2004).

Stephen F. Altschul et al., "Gapped BLAST and PSI-BLAST: a new generation of protein database search programs," Nucleic Acids Research, vol. 25, No. 17, pp. 3389-3402 (1997).

Björn Neubacher et al., "Preparation of sialylated oligosaccharides employing recombinant trans-sialidase from *Trypanosoma cruzi*," Org. Biomol. Chem., vol. 3, pp. 1551-1556 (2005).

Mutsumi Sano et al., "An enzyme releasing lacto-N-biose from oligosaccharides," Proc. Natl. Acad. Sci. USA, vol. 89, pp. 8512-8516 (Sep. 1992).

Samuel Karlin et al., "Applications and statistics for multiple high-scoring segments in molecular sequences," Proc. Natl. Acad. Sci. USA, vol. 90, pp. 5873-5877 (Jun. 1993).

Dirk Schmidt et al., "Chemoenzymatic Synthesis of Sialyl Oligosaccharides with Sialidases Employing Transglycosylation Methodology," J. Org. Chem., vol. 65, No. 25, pp. 8518-8526 (2000).

Sungjin Park et al., "Profiling of Glycosidase Activities Using Coumarin-Conjugated Glycoside Cocktails," Organic Letters, vol. 9, No. 4, pp. 619-622 (2007).

Sarah Hanson et al., "Chemoenzymatic synthesis of oligosaccharides and glycoproteins," Trends in Biochemical Sciences, vol. 29, No. 12, pp. 656-661 (Dec. 2004).

Michael Messer et al., "Evolution of Milk Oligosacharides and Lactose," Trends in Glycoscience and Glycotechnology, vol. 14, No. 77, pp. 153-176 (May 2002).

Tadasu Urashima et al., "Milk Oligosaccharides," Nutrition and Diet Research Progress, Nova Biomedical Books, pp. i-88 (2011).

T. Urashima et al., "Milk Oligosaccharides," Advanced Dairy Chemistry, vol. 3: Lactose, Water, Salts and Minor Constituents, Chapter 8, pp. 295-349 (2009).

Akihiro Imamura et al., "Di-tert-butylsilylene-Directed α-Selective Synthesis of 4-Methylumbelliferyl T-Antigen," Organic Letters, vol. 7, No. 20, pp. 4415-4418 (2005).

Wei Li et al., "Synthesis of oligosaccharides with lactose and N-acetylglucosamine as substrates by using β-D-galactosidase from *Bacillus circulans*," Eur. Food Res. Technol., vol. 231, pp. 55-63 (2010).

Rosalía Agustí et al., "Comparative rates of sialylation by recombinant trans-sialidase and inhibitor properties of synthetic oligosaccharides from *Trypanosoma cruzi* mucins-containing galactofuranose and galactopyranose," Bioorganic & Medicinal Chemistry, vol. 15, pp. 2611-2616 (2007).

Joachim Thiem et al., "Chemoenzymatic Syntheses of Sialyloligosaccharides with Immobilized Sialidase," Angew. Chem. Int. Ed. Engl., vol. 30, No. 11, pp. 1503-1505 (1991).

* cited by examiner

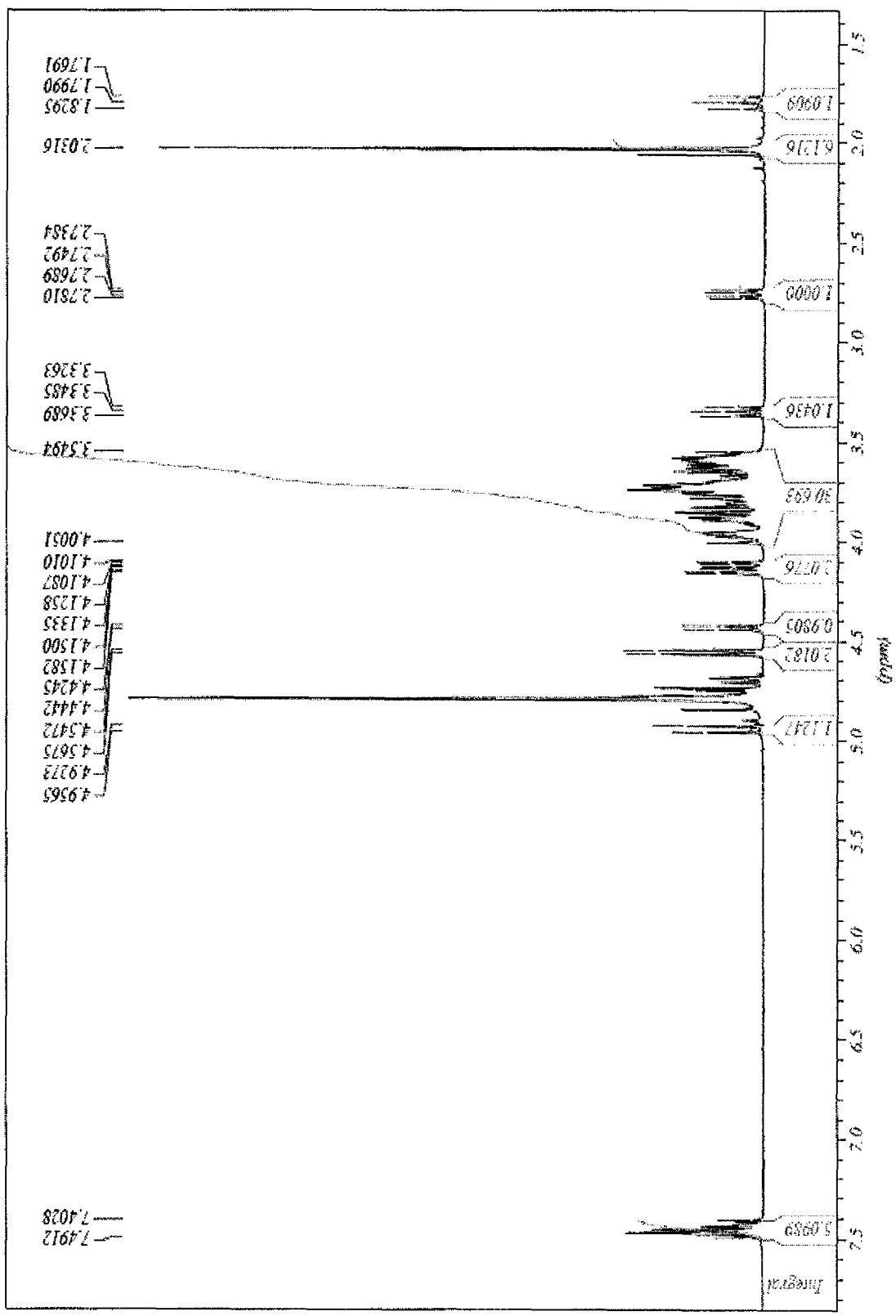
Figure 3. The 400 MHz $^1$H-NMR spectrum of benzyl 3'''-$O$-sialyl-β-LNnT

SEQUENCE LISTING

```
<160> NUMBER OF SEQ ID NOS: 21

<210> SEQ ID NO 1
<211> LENGTH: 448
<212> TYPE: PRT
<213> ORGANISM: Thermotoga maritima
<220> FEATURE:
<223> OTHER INFORMATION: Alpha-L-fucosidase, putative
<300> PUBLICATION INFORMATION:
<308> DATABASE ACCESSION NUMBER: gi 4980806
```

```
<300> PUBLICATION INFORMATION:
<308> DATABASE ACCESSION NUMBER: AAD35394.1
<300> PUBLICATION INFORMATION:
<308> DATABASE ACCESSION NUMBER: AE001712_7

<400> SEQUENCE: 1
```

| Met | Ile | Ser | Met | Lys | Pro | Arg | Tyr | Lys | Pro | Asp | Trp | Glu | Ser | Leu | Arg |
|---|---|---|---|---|---|---|---|---|---|---|---|---|---|---|---|
| 1 | | | | 5 | | | | | 10 | | | | | 15 | |

| Glu | His | Thr | Val | Pro | Lys | Trp | Phe | Asp | Lys | Ala | Lys | Phe | Gly | Ile | Phe |
|---|---|---|---|---|---|---|---|---|---|---|---|---|---|---|---|
| | | | 20 | | | | | 25 | | | | | 30 | | |

| Ile | His | Trp | Gly | Ile | Tyr | Ser | Val | Pro | Gly | Trp | Ala | Thr | Pro | Thr | Gly |
|---|---|---|---|---|---|---|---|---|---|---|---|---|---|---|---|
| | | | 35 | | | | | 40 | | | | | 45 | | |

| Glu | Leu | Gly | Lys | Val | Pro | Met | Asp | Ala | Trp | Phe | Phe | Gln | Asn | Pro | Tyr |
|---|---|---|---|---|---|---|---|---|---|---|---|---|---|---|---|
| | 50 | | | | | 55 | | | | | 60 | | | | |

| Ala | Glu | Trp | Tyr | Glu | Asn | Ser | Leu | Arg | Ile | Lys | Glu | Ser | Pro | Thr | Trp |
|---|---|---|---|---|---|---|---|---|---|---|---|---|---|---|---|
| 65 | | | | | 70 | | | | | 75 | | | | | 80 |

| Glu | Tyr | His | Val | Lys | Thr | Tyr | Gly | Asn | Phe | Glu | Tyr | Glu | Lys | Phe |
|---|---|---|---|---|---|---|---|---|---|---|---|---|---|---|
| | | | | 85 | | | | | 90 | | | | | 95 |

| Ala | Asp | Leu | Phe | Thr | Ala | Glu | Lys | Trp | Asp | Pro | Gln | Glu | Trp | Ala | Asp |
|---|---|---|---|---|---|---|---|---|---|---|---|---|---|---|---|
| | | | 100 | | | | | 105 | | | | | 110 | | |

| Leu | Phe | Lys | Lys | Ala | Gly | Ala | Lys | Tyr | Val | Ile | Pro | Thr | Thr | Lys | His |
|---|---|---|---|---|---|---|---|---|---|---|---|---|---|---|---|
| | | | 115 | | | | | 120 | | | | | 125 | | |

| His | Asp | Gly | Phe | Cys | Leu | Trp | Gly | Thr | Lys | Tyr | Thr | Asp | Phe | Asn | Ser |
|---|---|---|---|---|---|---|---|---|---|---|---|---|---|---|---|
| | 130 | | | | | 135 | | | | | 140 | | | | |

| Val | Lys | Arg | Gly | Pro | Lys | Arg | Asp | Leu | Val | Gly | Asp | Leu | Ala | Lys | Ala |
|---|---|---|---|---|---|---|---|---|---|---|---|---|---|---|---|
| 145 | | | | | 150 | | | | | 155 | | | | | 160 |

| Val | Arg | Glu | Ala | Gly | Leu | Arg | Phe | Gly | Val | Tyr | Tyr | Ser | Gly | Gly | Leu |
|---|---|---|---|---|---|---|---|---|---|---|---|---|---|---|---|
| | | | | 165 | | | | | 170 | | | | | 175 | |

| Asp | Trp | Arg | Phe | Thr | Thr | Glu | Pro | Ile | Arg | Tyr | Pro | Glu | Asp | Leu | Ser |
|---|---|---|---|---|---|---|---|---|---|---|---|---|---|---|---|
| | | | 180 | | | | | 185 | | | | | 190 | | |

| Tyr | Ile | Arg | Pro | Asn | Thr | Tyr | Glu | Tyr | Ala | Asp | Tyr | Ala | Tyr | Lys | Gln |
|---|---|---|---|---|---|---|---|---|---|---|---|---|---|---|---|
| | | 195 | | | | | 200 | | | | | 205 | | | |

| Val | Met | Glu | Leu | Val | Asp | Leu | Tyr | Leu | Pro | Asp | Val | Leu | Trp | Asn | Asp |
|---|---|---|---|---|---|---|---|---|---|---|---|---|---|---|---|
| 210 | | | | | 215 | | | | | 220 | | | | | |

| Met | Gly | Trp | Pro | Glu | Lys | Gly | Lys | Glu | Asp | Leu | Lys | Tyr | Leu | Phe | Ala |
|---|---|---|---|---|---|---|---|---|---|---|---|---|---|---|---|
| 225 | | | | | 230 | | | | | 235 | | | | | 240 |

| Tyr | Tyr | Tyr | Asn | Lys | His | Pro | Glu | Gly | Ser | Val | Asn | Asp | Arg | Trp | Gly |
|---|---|---|---|---|---|---|---|---|---|---|---|---|---|---|---|
| | | | | 245 | | | | | 250 | | | | | 255 | |

| Val | Pro | His | Trp | Asp | Phe | Lys | Thr | Ala | Glu | Tyr | His | Val | Asn | Tyr | Pro |
|---|---|---|---|---|---|---|---|---|---|---|---|---|---|---|---|
| | | | 260 | | | | | 265 | | | | | 270 | | |

| Gly | Asp | Leu | Pro | Gly | Tyr | Lys | Trp | Glu | Phe | Thr | Arg | Gly | Ile | Gly | Leu |
|---|---|---|---|---|---|---|---|---|---|---|---|---|---|---|---|
| | | 275 | | | | | 280 | | | | | 285 | | | |

| Ser | Phe | Gly | Tyr | Asn | Arg | Asn | Glu | Gly | Pro | His | Met | Leu | Ser | Val |
|---|---|---|---|---|---|---|---|---|---|---|---|---|---|---|
| | 290 | | | | | 295 | | | | | 300 | | | |

| Glu | Gln | Leu | Val | Tyr | Thr | Leu | Val | Asp | Val | Ser | Lys | Gly | Gly | Asn |
|---|---|---|---|---|---|---|---|---|---|---|---|---|---|---|
| 305 | | | | | 310 | | | | | 315 | | | | | 320 |

| Leu | Leu | Leu | Asn | Val | Gly | Pro | Lys | Gly | Asp | Gly | Thr | Ile | Pro | Asp | Leu |
|---|---|---|---|---|---|---|---|---|---|---|---|---|---|---|---|
| | | | | 325 | | | | | 330 | | | | | 335 | |

| Gln | Lys | Glu | Arg | Leu | Leu | Gly | Leu | Gly | Glu | Trp | Leu | Arg | Lys | Tyr | Gly |
|---|---|---|---|---|---|---|---|---|---|---|---|---|---|---|---|
| | | | 340 | | | | | 345 | | | | | 350 | | |

| Asp | Ala | Ile | Tyr | Gly | Thr | Ser | Val | Trp | Glu | Arg | Cys | Ala | Lys | Thr |
|---|---|---|---|---|---|---|---|---|---|---|---|---|---|---|
| | | 355 | | | | | 360 | | | | | 365 | | |

| Glu | Asp | Gly | Thr | Glu | Ile | Arg | Phe | Thr | Arg | Lys | Cys | Asn | Arg | Ile | Phe |
|---|---|---|---|---|---|---|---|---|---|---|---|---|---|---|---|
| | 370 | | | | | 375 | | | | | 380 | | | | |

```
Val Ile Phe Leu Gly Ile Pro Thr Gly Glu Lys Ile Val Ile Glu Asp
385                 390                 395                 400

Leu Asn Leu Ser Ala Gly Thr Val Arg His Phe Leu Thr Gly Glu Arg
                405                 410                 415

Leu Ser Phe Lys Asn Val Gly Lys Asn Leu Glu Ile Thr Val Pro Lys
            420                 425                 430

Lys Leu Leu Glu Thr Asp Ser Ile Thr Leu Val Leu Glu Ala Val Glu
        435                 440                 445

<210> SEQ ID NO 2
<211> LENGTH: 403
<212> TYPE: PRT
<213> ORGANISM: Sulfolobus solfataricus
<220> FEATURE:
<223> OTHER INFORMATION: Alpha-fucosidase C-terminal fragment (fucA1)
<300> PUBLICATION INFORMATION:
<308> DATABASE ACCESSION NUMBER: gi 13816464
<300> PUBLICATION INFORMATION:
<308> DATABASE ACCESSION NUMBER: AAK43159.1

<400> SEQUENCE: 2

Met Phe Thr Gly Glu Asn Trp Asp Pro Tyr Glu Trp Ala Lys Val Phe
1               5                   10                  15

Lys Lys Ser Gly Ala Lys Phe Val Val Leu Val Ala Glu His His Asp
            20                  25                  30

Gly Phe Ala Leu Trp Glu Ser Asn Tyr Thr Arg Trp Cys Ala Thr Lys
        35                  40                  45

Ile Gly Pro Lys Arg Asp Ile Val Arg Glu Leu Lys Glu Ala Val Glu
    50                  55                  60

Gly Gln Gly Leu Ile Phe Gly Ile Ser Tyr His Arg Ala Glu His Trp
65                  70                  75                  80

Trp Phe Phe Asp Gln Gly Met Lys Ile Glu Ser Asp Val Lys Asp Pro
                85                  90                  95

Arg Tyr Leu Asp Leu Tyr Gly Pro Ala Gln Ser Ala Ser Leu Asn Pro
            100                 105                 110

Arg Asp Pro Pro Ser Leu Asp Asn Val Gln Pro Asn Asp Glu Phe Leu
        115                 120                 125

Met Asp Trp Leu Leu Arg Ile Val Glu Ala Val Glu Lys Tyr Arg Pro
130                 135                 140

Trp Leu Val Tyr Phe Asp Trp Trp Ile Ala Asn Pro Ser Phe Gln Pro
145                 150                 155                 160

Tyr Leu Lys Ala Phe Ala Ser Tyr Tyr Asn Arg Ser Tyr Lys Trp
            165                 170                 175

Gly Ile Glu Pro Val Ile Ile Tyr Lys Gln Gly Ala Phe Gly Glu Gly
            180                 185                 190

Thr Ala Ile Pro Asp Leu Ala Glu Arg Gly Thr Ile Lys Asn Val Tyr
        195                 200                 205

Pro Ser Thr Trp Leu Ala Asp Thr Ser Ile Asp Tyr Lys Ser Trp Gly
    210                 215                 220

Tyr Ile Lys Asp Ala Glu Tyr Lys Leu Pro Ser Val Ile Leu Ser His
225                 230                 235                 240

Leu Gly Asp Val Val Ser Lys Asn Gly Val Phe Leu Leu Asn Ile Gly
                245                 250                 255

Pro Lys Ala Asp Gly Thr Ile Pro Glu Glu Ala Lys Arg Ile Leu Leu
            260                 265                 270

Asp Val Gly Asp Trp Leu Asn Val Asn Gly Glu Ala Ile Phe Gly Ser
        275                 280                 285
```

```
Lys Pro Trp Arg Val Tyr Gly Glu Gly Pro Ser Gly Ile Asn Glu Gly
    290                 295                 300

Gly Phe Phe Thr Glu Arg Lys Ile Thr Leu Gly Tyr Gln Asp Val Arg
305                 310                 315                 320

Tyr Thr Val Lys Asp Tyr Tyr Pro Arg Gln Arg His Ile Tyr Ala Ile
                325                 330                 335

Leu Phe Gly Lys Pro Lys Glu Ile Thr Leu Arg Ser Phe Met Lys Asn
                340                 345                 350

Leu Lys Leu Ile Glu Glu Ala Val Ile Val Asp Val Ser Arg Leu Asp
                355                 360                 365

Gly Lys Gly Lys Leu Glu Trp Ser Leu Ser Asp Glu Gly Leu Lys Ile
    370                 375                 380

Lys Ile Glu Glu Val Ile Arg Ala Pro Leu Val Ile Arg Val Ile Leu
385                 390                 395                 400

Asp Tyr Arg

<210> SEQ ID NO 3
<211> LENGTH: 1959
<212> TYPE: PRT
<213> ORGANISM: Bifidobacterium bifidum
<220> FEATURE:
<223> OTHER INFORMATION: Alpha-fucosidase
<300> PUBLICATION INFORMATION:
<308> DATABASE ACCESSION NUMBER: gi 34451973
<300> PUBLICATION INFORMATION:
<308> DATABASE ACCESSION NUMBER: AAQ72464.1

<400> SEQUENCE: 3

Met Lys His Arg Ala Met Ser Ser Arg Leu Met Pro Leu Val Ala Ser
1               5                   10                  15

Cys Ala Thr Val Gly Met Leu Leu Ala Gly Leu Pro Val Ser Ala Val
                20                  25                  30

Ala Val Gly Thr Thr Arg Ala Ala Ala Ser Asp Ala Ser Ser Ser Thr
            35                  40                  45

Thr Ala Thr Ile Thr Pro Ser Ala Asp Thr Thr Leu Gln Thr Trp Thr
    50                  55                  60

Ser Glu Lys Asn Ser Ser Met Ala Ser Lys Pro Tyr Ile Gly Thr Leu
65                  70                  75                  80

Gln Gly Pro Ser Gln Gly Val Phe Gly Glu Lys Phe Glu Ser Thr Asp
                85                  90                  95

Ala Ala Asp Thr Thr Asp Leu Lys Thr Gly Leu Leu Thr Phe Asp Leu
                100                 105                 110

Ser Ala Tyr Asp His Ala Pro Asp Ser Ala Thr Phe Glu Met Thr Tyr
            115                 120                 125

Leu Gly Tyr Arg Gly Asn Pro Thr Ala Thr Asp Thr Asp Thr Ile Lys
    130                 135                 140

Val Thr Pro Val Asp Thr Thr Val Cys Thr Asn Asn Ala Thr Asp Cys
145                 150                 155                 160

Gly Ala Asn Val Ala Thr Gly Ala Thr Lys Pro Lys Phe Ser Ile Asn
                165                 170                 175

Asp Ser Ser Phe Val Ala Glu Ser Lys Pro Phe Glu Tyr Gly Thr Thr
                180                 185                 190

Val Tyr Thr Gly Asp Ala Ile Thr Val Val Pro Ala Asn Thr Lys Lys
            195                 200                 205

Val Thr Val Asp Val Thr Glu Ile Val Arg Gln Gln Phe Ala Glu Gly
    210                 215                 220
```

```
Lys Lys Val Ile Thr Leu Ala Val Gly Glu Thr Lys Thr Glu Val
225                 230                 235                 240

Arg Phe Ala Ser Ser Glu Gly Thr Thr Ser Leu Asn Gly Ala Thr Ala
                245                 250                 255

Asp Met Ala Pro Lys Leu Thr Val Ser Val Ser Thr Lys Asp Asp Leu
            260                 265                 270

Lys Pro Ser Ala Asp Thr Thr Leu Gln Ala Trp Ala Ser Glu Lys Asn
        275                 280                 285

Glu Lys Lys Asn Thr Ala Ala Tyr Val Gly Ala Leu Gln Pro Glu Gly
    290                 295                 300

Asp Tyr Gly Asp Phe Gly Glu Lys Phe Lys Ser Thr Asp Val His Asp
305                 310                 315                 320

Val Thr Asp Ala Lys Met Gly Leu Met Thr Phe Asp Leu Ser Asp Tyr
                325                 330                 335

Thr Ala Ala Pro Glu His Ser Ile Leu Thr Leu Thr Tyr Leu Gly Tyr
            340                 345                 350

Ala Gly Ala Asp Lys Thr Ala Thr Ala Thr Asp Lys Val Lys Val Val
        355                 360                 365

Ala Val Asp Thr Ser Arg Cys Thr Gly Thr Ala Pro Cys Asp Thr Asn
    370                 375                 380

Asn Ala Thr Trp Ala Asn Arg Pro Asp Phe Glu Val Thr Asp Thr Thr
385                 390                 395                 400

Lys Thr Ala Thr Ser His Ala Phe Ala Tyr Gly Ser Lys Lys Tyr Ser
                405                 410                 415

Asp Gly Met Thr Val Glu Ser Gly Asn Ala Lys Lys Val Leu Leu Asp
            420                 425                 430

Val Ser Asp Val Ile Lys Ala Glu Phe Ala Lys Phe Ser Ala Gly Ala
        435                 440                 445

Thr Glu Lys Lys Ile Thr Leu Ala Leu Gly Glu Leu Asn Lys Ser Asp
    450                 455                 460

Met Arg Phe Gly Ser Lys Glu Val Thr Ser Leu Thr Gly Ala Thr Glu
465                 470                 475                 480

Ala Met Gln Pro Thr Leu Ser Val Thr Lys Lys Pro Lys Ala Tyr Thr
                485                 490                 495

Leu Ser Ile Glu Gly Pro Thr Lys Val Lys Tyr Gln Lys Gly Glu Ala
            500                 505                 510

Phe Asp Lys Ala Gly Leu Val Val Lys Ala Thr Ser Thr Ala Asp Gly
        515                 520                 525

Thr Val Lys Thr Leu Thr Glu Gly Asn Gly Glu Asp Asn Tyr Thr Ile
    530                 535                 540

Asp Thr Ser Ala Phe Asp Ser Ala Ser Ile Gly Val Tyr Pro Val Thr
545                 550                 555                 560

Val Lys Tyr Asn Lys Asp Pro Glu Ile Ala Ala Ser Phe Asn Ala Tyr
                565                 570                 575

Val Ile Ala Ser Val Glu Asp Gly Asp Gly Asp Thr Ser Lys Asp
            580                 585                 590

Asp Trp Leu Trp Tyr Lys Gln Pro Ala Ser Gln Thr Asp Ala Thr Ala
        595                 600                 605

Thr Ala Gly Gly Asn Tyr Gly Asn Pro Asp Asn Asn Arg Trp Gln Gln
    610                 615                 620

Thr Thr Leu Pro Phe Gly Asn Gly Lys Ile Gly Gly Thr Val Trp Gly
625                 630                 635                 640
```

```
Glu Val Ser Arg Glu Arg Val Thr Phe Asn Glu Thr Leu Trp Thr
                645                 650                 655

Gly Gly Pro Gly Ser Ser Thr Ser Tyr Asn Gly Asn Asn Glu Thr
            660                 665                 670

Lys Gly Gln Asn Gly Ala Thr Leu Arg Ala Leu Asn Lys Gln Leu Ala
        675                 680                 685

Asn Gly Ala Glu Thr Val Asn Pro Gly Asn Leu Thr Gly Gly Glu Asn
690                 695                 700

Ala Ala Glu Gln Gly Asn Tyr Leu Asn Trp Gly Asp Ile Tyr Leu Asp
705                 710                 715                 720

Tyr Gly Phe Asn Asp Thr Thr Val Thr Glu Tyr Arg Arg Asp Leu Asn
            725                 730                 735

Leu Ser Lys Gly Lys Ala Asp Val Thr Phe Lys His Asp Gly Val Thr
            740                 745                 750

Tyr Thr Arg Glu Tyr Phe Ala Ser Asn Pro Asp Asn Val Met Val Ala
            755                 760                 765

Arg Leu Thr Ala Ser Lys Ala Gly Lys Leu Asn Phe Asn Val Ser Met
770                 775                 780

Pro Thr Asn Thr Asn Tyr Ser Lys Thr Gly Glu Thr Thr Val Lys
785                 790                 795                 800

Gly Asp Thr Leu Thr Val Lys Gly Ala Leu Gly Asn Asn Gly Leu Leu
            805                 810                 815

Tyr Asn Ser Gln Ile Lys Val Val Leu Asp Asn Gly Glu Gly Thr Leu
                820                 825                 830

Ser Glu Gly Ser Asp Gly Ala Ser Leu Lys Val Ser Asp Ala Lys Ala
            835                 840                 845

Val Thr Leu Tyr Ile Ala Ala Thr Asp Tyr Lys Gln Lys Tyr Pro
850                 855                 860

Ser Tyr Arg Thr Gly Glu Thr Ala Ala Glu Val Asn Thr Arg Val Ala
865                 870                 875                 880

Lys Val Val Gln Asp Ala Ala Asn Lys Gly Tyr Thr Ala Val Lys Lys
                885                 890                 895

Ala His Ile Asp Asp His Ser Ala Ile Tyr Asp Arg Val Lys Ile Asp
            900                 905                 910

Leu Gly Gln Ser Gly His Ser Ser Asp Gly Ala Val Ala Thr Asp Ala
        915                 920                 925

Leu Leu Lys Ala Tyr Gln Arg Gly Ser Ala Thr Thr Ala Gln Lys Arg
930                 935                 940

Glu Leu Glu Thr Leu Val Tyr Lys Tyr Gly Arg Tyr Leu Thr Ile Gly
945                 950                 955                 960

Ser Ser Arg Glu Asn Ser Gln Leu Pro Ser Asn Leu Gln Gly Ile Trp
            965                 970                 975

Ser Val Thr Ala Gly Asp Asn Ala His Gly Asn Thr Pro Trp Gly Ser
            980                 985                 990

Asp Phe His Met Asn Val Asn Leu Gln Met Asn Tyr Trp Pro Thr Tyr
            995                 1000                1005

Ser Ala Asn Met Gly Glu Leu Ala Glu Pro Leu Ile Glu Tyr Val
    1010                1015                1020

Glu Gly Leu Val Lys Pro Gly Arg Val Thr Ala Lys Val Tyr Ala
    1025                1030                1035

Gly Ala Glu Thr Thr Asn Pro Glu Thr Thr Pro Ile Gly Glu Gly
    1040                1045                1050

Glu Gly Tyr Met Ala His Thr Glu Asn Thr Ala Tyr Gly Trp Thr
```

```
                   1055                1060                1065
Ala Pro Gly Gln Ser Phe Ser Trp Gly Trp Ser Pro Ala Ala Val
            1070                1075                1080
Pro Trp Ile Leu Gln Asn Val Tyr Glu Ala Tyr Glu Tyr Ser Gly
            1085                1090                1095
Asp Pro Ala Leu Leu Asp Arg Val Tyr Ala Leu Leu Lys Glu Glu
            1100                1105                1110
Ser His Phe Tyr Val Asn Tyr Met Leu His Lys Ala Gly Ser Ser
            1115                1120                1125
Ser Gly Asp Arg Leu Thr Thr Gly Val Ala Tyr Ser Pro Glu Gln
            1130                1135                1140
Gly Pro Leu Gly Thr Asp Gly Asn Thr Tyr Glu Ser Ser Leu Val
            1145                1150                1155
Trp Gln Met Leu Asn Asp Ala Ile Glu Ala Ala Lys Ala Lys Gly
            1160                1165                1170
Asp Pro Asp Gly Leu Val Gly Asn Thr Thr Asp Cys Ser Ala Asp
            1175                1180                1185
Asn Trp Ala Lys Asn Asp Ser Gly Asn Phe Thr Asp Ala Asn Ala
            1190                1195                1200
Asn Arg Ser Trp Ser Cys Ala Lys Ser Leu Leu Lys Pro Ile Glu
            1205                1210                1215
Val Gly Asp Ser Gly Gln Ile Lys Glu Trp Tyr Phe Glu Gly Ala
            1220                1225                1230
Leu Gly Lys Lys Lys Asp Gly Ser Thr Ile Ser Gly Tyr Gln Ala
            1235                1240                1245
Asp Asn Gln His Arg His Met Ser His Leu Leu Gly Leu Phe Pro
            1250                1255                1260
Gly Asp Leu Ile Thr Ile Asp Asn Ser Glu Tyr Met Asp Ala Ala
            1265                1270                1275
Lys Thr Ser Leu Arg Tyr Arg Cys Phe Lys Gly Asn Val Leu Gln
            1280                1285                1290
Ser Asn Thr Gly Trp Ala Ile Gly Gln Arg Ile Asn Ser Trp Ala
            1295                1300                1305
Arg Thr Gly Asp Gly Asn Thr Thr Tyr Gln Leu Val Glu Leu Gln
            1310                1315                1320
Leu Lys Asn Ala Met Tyr Ala Asn Leu Phe Asp Tyr His Ala Pro
            1325                1330                1335
Phe Gln Ile Asp Gly Asn Phe Gly Asn Thr Ser Gly Val Asp Glu
            1340                1345                1350
Met Leu Leu Gln Ser Asn Ser Thr Phe Thr Asp Thr Ala Gly Lys
            1355                1360                1365
Lys Tyr Val Asn Tyr Thr Asn Ile Leu Pro Ala Leu Pro Asp Ala
            1370                1375                1380
Trp Ala Gly Gly Ser Val Ser Gly Leu Val Ala Arg Gly Asn Phe
            1385                1390                1395
Thr Val Gly Thr Thr Trp Lys Asn Gly Lys Ala Thr Glu Val Arg
            1400                1405                1410
Leu Thr Ser Asn Lys Gly Lys Gln Ala Ala Val Lys Ile Thr Ala
            1415                1420                1425
Gly Gly Ala Gln Asn Tyr Glu Val Lys Asn Gly Asp Thr Ala Val
            1430                1435                1440
Asn Ala Lys Val Val Thr Asn Ala Asp Gly Ala Ser Leu Leu Val
            1445                1450                1455
```

-continued

```
Phe Asp Thr Thr Ala Gly Thr Thr Tyr Thr Ile Thr Lys Lys Ala
    1460            1465            1470

Ser Ala Asn Val Pro Val Thr Gly Val Thr Val Thr Gly Ala Asn
    1475            1480            1485

Thr Ala Thr Ala Gly Asp Thr Val Thr Leu Thr Ala Thr Val Ala
    1490            1495            1500

Pro Ala Asn Ala Thr Asp Lys Ser Val Thr Trp Ser Thr Ser Asp
    1505            1510            1515

Ala Ala Val Ala Thr Val Asn Ala Asn Gly Val Val Thr Thr Lys
    1520            1525            1530

Lys Ala Gly Lys Val Thr Ile Thr Ala Thr Ser Asn Gly Asp Lys
    1535            1540            1545

Thr Lys Phe Gly Ser Ile Glu Ile Thr Val Ser Ala Ala Thr Val
    1550            1555            1560

Pro Val Thr Ser Val Thr Val Ala Gly Asp Ala Ala Met Thr Val
    1565            1570            1575

Asp Gly Glu Gln Thr Leu Thr Ala Thr Val Ala Pro Ala Thr Ala
    1580            1585            1590

Thr Asp Lys Thr Val Thr Trp Lys Ser Ser Asp Ala Thr Val Ala
    1595            1600            1605

Thr Val Asp Ala Asn Gly Lys Val Val Ala Lys Lys Ala Gly Glu
    1610            1615            1620

Val Thr Ile Thr Ala Thr Ala Gly Gly Val Ser Gly Thr Leu Lys
    1625            1630            1635

Ile Thr Val Ser Asp Lys Ala Pro Thr Val Ile Pro Val Gln Ser
    1640            1645            1650

Val Thr Val Thr Gly Lys Gln Glu Leu Val Glu Gly Ala Ser Thr
    1655            1660            1665

Thr Leu Thr Ala Thr Val Ala Pro Ala Asp Ala Thr Asp Lys Thr
    1670            1675            1680

Val Thr Trp Lys Ser Ser Asp Glu Ser Val Ala Thr Val Asp Lys
    1685            1690            1695

Asp Gly Val Val Thr Ala Lys Lys Ala Gly Thr Val Thr Ile Thr
    1700            1705            1710

Ala Thr Ala Gly Gly Val Ser Gly Thr Leu His Ile Thr Val Thr
    1715            1720            1725

Ala Lys Pro Val Glu Thr Val Pro Val Thr Ser Val Glu Val Thr
    1730            1735            1740

Val Glu Ala Gly Thr Thr Val Ser Val Gly Lys Thr Leu Gln Ala
    1745            1750            1755

Thr Ala Thr Val Lys Pro Gly Asn Ala Thr Asn Lys Lys Val Thr
    1760            1765            1770

Trp Lys Ser Ser Asp Glu Ser Ile Ala Thr Val Asp Ala Asn Gly
    1775            1780            1785

Val Ile Thr Ala Lys Lys Ala Gly Lys Val Val Ile Thr Ala Thr
    1790            1795            1800

Ser Thr Asp Gly Thr Asp Lys Ser Gly Ser Val Glu Ile Thr Val
    1805            1810            1815

Val Asp Glu Thr Lys Pro Thr Pro Asp His Lys Ser Val Lys Ala
    1820            1825            1830

Asp Thr Gly Asp Val Thr Ala Gly Lys Thr Gly Thr Val Thr Glu
    1835            1840            1845
```

```
Pro Lys Asp Val Ala Gly Trp Lys Ser Arg Ser Ile Ile Lys Gln
    1850                1855                1860

Gly Lys Leu Gly Lys Ala Glu Ile Ala Asp Gly Thr Leu Val Tyr
    1865                1870                1875

Ala Ala Gly Asp Lys Thr Gly Asp Asp Ser Phe Val Val Gln Tyr
    1880                1885                1890

Thr Met Ala Asp Gly Thr Val Ile Asp Val Thr Tyr Ser Val Thr
    1895                1900                1905

Val Lys Ala Ala Glu Thr Gly Lys Asn Asp Gly Asp Gly Lys Gly
    1910                1915                1920

Asp Gly Val Ala Lys Thr Gly Ala Ala Val Gly Ala Leu Ala Gly
    1925                1930                1935

Leu Gly Leu Met Leu Leu Ala Val Gly Val Ser Val Val Met Ile
    1940                1945                1950

Arg Arg Lys His Ser Ala
    1955

<210> SEQ ID NO 4
<211> LENGTH: 1493
<212> TYPE: PRT
<213> ORGANISM: Bifidobacterium bifidum
<220> FEATURE:
<223> OTHER INFORMATION: Alpha-L-fucosidase
<300> PUBLICATION INFORMATION:
<308> DATABASE ACCESSION NUMBER: gi 242345155
<300> PUBLICATION INFORMATION:
<308> DATABASE ACCESSION NUMBER: BAH80310.1

<400> SEQUENCE: 4

Met Leu His Thr Ala Ser Arg Gly Cys Ser Arg Ser Trp Leu Arg Arg
1               5                   10                  15

Leu Thr Ala Leu Ile Ala Val Ser Ala Leu Ala Phe Val Ala Leu Pro
                20                  25                  30

Asn Val Ala Val Ala Ala Asp Pro Met Glu Tyr Leu Asp Val Ser Phe
            35                  40                  45

Gly Gly Thr Phe Ala Ala Asp Thr Tyr Thr Thr Gly Gly Asp Glu Val
        50                  55                  60

Ala Lys Gly Pro Val Thr Lys His Gly Ser Ile Pro Thr Lys Leu Asp
65                  70                  75                  80

Gly Gly Gly Ile Thr Leu Ala Gly Gly Thr Asn Gly Val Thr Phe Thr
                85                  90                  95

Ser Thr Ala Ser Phe Ser Glu Ser Gly Lys Val Asn Lys Gly Phe Arg
            100                 105                 110

Ala Glu Met Glu Tyr Arg Thr Thr Gln Thr Pro Ser Asn Leu Ala Thr
        115                 120                 125

Leu Phe Ser Ala Met Gly Asn Ile Phe Val Arg Ala Asn Gly Ser Asn
    130                 135                 140

Leu Glu Tyr Gly Phe Ser Thr Asn Pro Ser Gly Ser Thr Trp Asn Asp
145                 150                 155                 160

Tyr Thr Lys Ser Val Thr Leu Pro Ser Asn Asn Val Lys His Ile Ile
                165                 170                 175

Gln Leu Thr Tyr Leu Pro Gly Ala Asp Gly Ala Ala Ser Thr Leu Gln
            180                 185                 190

Leu Ser Val Asp Gly Val Ala Gly Glu Thr Ala Thr Ser Ala Ala Gly
        195                 200                 205

Glu Leu Ala Ala Val Ser Asp Ser Val Gly Asn Lys Phe Gly Ile Gly
    210                 215                 220
```

```
Tyr Glu Val Asn Pro Ala Ser Gly Ala Ala Ser Arg Gly Leu Ala Gly
225                 230                 235                 240

Asp Val Phe Arg Ala Arg Val Ala Asp Ser Asp Ala Pro Trp Glu Ile
            245                 250                 255

Leu Asp Ala Ser Gln Leu Leu His Val Asn Phe Asn Gly Thr Phe Ser
        260                 265                 270

Gly Thr Ser Tyr Thr Ala Ala Ser Gly Glu Gln Met Leu Gly Ser Leu
    275                 280                 285

Val Ser Arg Ser Ala Asn Pro Ser Ile Ser Asn Ser Ala Val Thr Leu
290                 295                 300

Gly Gly Gly Thr Ala Gly Phe Asp Phe Thr Pro Thr Asp Phe Thr Leu
305                 310                 315                 320

Gly Asp Asn Glu Ala Ile Thr Arg Pro Leu Val Ala Glu Leu Arg Phe
            325                 330                 335

Thr Pro Thr Gln Thr Gly Asp Asn Gln Thr Leu Phe Gly Ala Gly Gly
        340                 345                 350

Asn Leu Phe Leu Arg Tyr Glu Ser Asn Lys Leu Val Phe Gly Ala Ser
    355                 360                 365

Thr Lys Ser Gly Asp Asn Trp Thr Asp His Lys Ile Glu Ser Ala Ala
370                 375                 380

Ala Thr Gly Ala Glu His Val Ser Val Ala Tyr Val Pro Asn Lys
385                 390                 395                 400

Ala Gly Thr Gly Ala Lys Leu Val Met Arg Val Asp Gly Gly Asp Ala
            405                 410                 415

Gln Thr Lys Asp Ile Thr Gly Leu Ala Tyr Leu Asn Ser Ser Ile Lys
        420                 425                 430

Gly Lys Val Gly Phe Gly Asn Asp Val His Thr Asp Ala Leu Ser Arg
    435                 440                 445

Gly Phe Val Gly Ser Leu Ser Glu Ile Arg Leu Ala Glu Thr Ser Ala
450                 455                 460

Asn Phe Thr Thr Asn Glu Phe Lys Leu Val Tyr Ser Gln Val Ser Cys
465                 470                 475                 480

Asp Thr Ser Gly Ile Lys Glu Ala Asn Thr Phe Asp Val Glu Pro Ala
            485                 490                 495

Glu Cys Glu Ala Ala Leu Lys Thr Lys Leu Ser Lys Leu Arg Pro Thr
        500                 505                 510

Glu Gly Gln Ala Asp Tyr Ile Asp Trp Gly Gln Ile Gly Phe Leu His
    515                 520                 525

Tyr Gly Ile Asn Thr Tyr Tyr Asn Gln Glu Trp Gly His Gly Asn Glu
530                 535                 540

Asp Pro Ser Arg Ile Asn Pro Thr Gly Leu Asp Thr Asp Gln Trp Ala
545                 550                 555                 560

Lys Ser Phe Ala Asp Gly Gly Phe Lys Met Ile Met Val Thr Val Lys
            565                 570                 575

His His Asp Gly Phe Glu Leu Tyr Asp Ser Arg Tyr Asn Thr Glu His
        580                 585                 590

Asp Trp Ala Asn Thr Ala Val Ala Lys Arg Thr Gly Glu Lys Asp Leu
    595                 600                 605

Phe Arg Lys Ile Val Ala Ser Ala Lys Lys Tyr Gly Leu Lys Val Gly
610                 615                 620

Ile Tyr Tyr Ser Pro Ala Asp Ser Tyr Met Glu Arg Lys Gly Val Trp
625                 630                 635                 640
```

-continued

Gly Asn Asn Ser Ala Arg Val Glu Arg Thr Ile Pro Thr Leu Val Glu
            645                 650                 655

Asn Asp Asp Arg Ala Gly Lys Val Ala Ser Gly Lys Leu Pro Thr Phe
        660                 665                 670

Lys Tyr Lys Ala Thr Asp Tyr Gly Ala Tyr Met Leu Asn Gln Leu Tyr
    675                 680                 685

Glu Leu Leu Thr Glu Tyr Gly Asp Ile Ser Glu Val Trp Phe Asp Gly
690                 695                 700

Ala Gln Gly Asn Thr Ala Gly Thr Glu His Tyr Asp Tyr Gly Val Phe
705                 710                 715                 720

Tyr Glu Met Ile Arg Arg Leu Gln Pro Gln Ala Ile Gln Ala Asn Ala
                725                 730                 735

Ala Tyr Asp Ala Arg Trp Val Gly Asn Glu Asp Gly Trp Ala Arg Gln
            740                 745                 750

Thr Glu Trp Ser Pro Gln Ala Ala Tyr Asn Asp Gly Val Asp Lys Val
        755                 760                 765

Ser Leu Lys Pro Gly Gln Met Ala Pro Asp Gly Lys Leu Gly Ser Met
    770                 775                 780

Ser Ser Val Leu Ser Glu Ile Arg Ser Gly Ala Ala Asn Gln Leu His
785                 790                 795                 800

Trp Tyr Pro Ala Glu Val Asp Ala Lys Asn Arg Pro Gly Trp Phe Tyr
                805                 810                 815

Arg Ala Ser Gln Ser Pro Ala Ser Val Ala Glu Val Val Lys Tyr Tyr
            820                 825                 830

Glu Gln Ser Thr Gly Arg Asn Ser Gln Tyr Leu Leu Asn Val Pro Pro
        835                 840                 845

Ser Asp Thr Gly Lys Leu Ala Asp Ala Asp Ala Ala Gly Leu Lys Gly
    850                 855                 860

Leu Gly Glu Glu Leu Ala Arg Arg Tyr Gly Thr Asp Leu Ala Leu Gly
865                 870                 875                 880

Lys Ser Ala Thr Val Ala Ala Ser Ala Asn Asp Thr Ala Val Ala Ala
                885                 890                 895

Pro Lys Leu Thr Asp Gly Ser Lys Leu Ser Ser Asp Lys Ala Val Gly
            900                 905                 910

Asn Thr Pro Thr Tyr Thr Ile Asp Leu Gly Ser Thr Val Ala Val Asp
        915                 920                 925

Ala Val Lys Ile Ser Glu Asp Val Arg Asn Ala Gly Gln Gln Ile Glu
    930                 935                 940

Ser Ala Thr Leu Gln Gly Arg Val Asn Gly Thr Trp Thr Asn Leu Ala
945                 950                 955                 960

Thr Met Thr Thr Val Gly Gln Gln Arg Asp Leu Arg Phe Thr Ser Gln
                965                 970                 975

Asn Ile Asp Ala Ile Arg Leu Val Val Asn Ser Ser Arg Gly Pro Val
            980                 985                 990

Arg Leu Ser Arg Leu Glu Val Phe His Thr Glu Ser Glu Ile Gln Thr
        995                 1000                1005

Gly Ala Arg Ala Tyr Tyr Ile Asp Pro Thr Ala Gln Thr Ala Gly
        1010                1015                1020

Asp Gly Phe Thr Lys Asp Lys Pro Met Thr Ser Ile Glu Gln Leu
        1025                1030                1035

His Asp Val Thr Val Ala Pro Gly Ser Val Ile Phe Val Lys Ala
        1040                1045                1050

Gly Thr Glu Leu Thr Gly Asp Phe Ala Val Phe Gly Tyr Gly Thr

```
                  1055                1060                1065
Lys Asp Glu Pro Ile Thr Val Thr Thr Tyr Gly Glu Ser Asp Lys
     1070                1075                1080
Ala Thr Thr Ala Ser Phe Asp Gly Met Thr Ala Gly Leu Thr Leu
     1085                1090                1095
Lys Gln Ala Leu Lys Ala Leu Gly Lys Asp Asp Ala Gly Trp Val
     1100                1105                1110
Val Ala Asp Ser Ala Thr Ala Pro Ala Ser Arg Val Tyr Val Pro
     1115                1120                1125
Gln Asp Glu Ile Ser Val His Ala Gln Ser Ser Gln Asn Ser Gly
     1130                1135                1140
Ala Glu Ala Ala Arg Ala Leu Asp Gly Asp Ser Thr Ser Trp
     1145                1150                1155
His Ser Gln Tyr Ser Pro Thr Thr Ala Ser Ala Pro His Trp Val
     1160                1165                1170
Thr Leu Asp Leu Gly Lys Ser Arg Glu Asn Val Ala Tyr Phe Asp
     1175                1180                1185
Tyr Leu Ala Arg Ile Asp Gly Asn Asn Asn Gly Ala Ala Lys Asp
     1190                1195                1200
Tyr Glu Val Tyr Val Ser Asp Asp Pro Asn Asp Phe Gly Ala Pro
     1205                1210                1215
Val Ala Ser Gly Thr Leu Lys Asn Val Ala Tyr Thr Gln Arg Ile
     1220                1225                1230
Lys Leu Thr Pro Lys Asn Gly Arg Tyr Val Lys Phe Val Ile Lys
     1235                1240                1245
Thr Asp Tyr Ser Gly Ser Asn Phe Gly Ser Ala Ala Glu Met Asn
     1250                1255                1260
Val Glu Leu Leu Pro Thr Ala Val Glu Glu Asp Lys Val Ala Thr
     1265                1270                1275
Pro Gln Lys Pro Thr Val Asp Asp Ala Asp Thr Tyr Thr Ile
     1280                1285                1290
Pro Asp Ile Glu Gly Val Val Tyr Lys Val Asp Gly Lys Val Leu
     1295                1300                1305
Ala Ala Gly Ser Val Val Asn Val Gly Asp Glu Asp Val Thr Val
     1310                1315                1320
Thr Val Thr Ala Glu Pro Ala Asp Gly Tyr Arg Phe Pro Asp Gly
     1325                1330                1335
Val Thr Ser Pro Val Thr Tyr Glu Leu Thr Phe Thr Lys Lys Gly
     1340                1345                1350
Gly Glu Lys Pro Pro Thr Glu Val Asn Lys Asp Lys Leu His Ala
     1355                1360                1365
Thr Ile Thr Lys Ala Gln Ala Ile Asp Arg Ser Ala Tyr Thr Asp
     1370                1375                1380
Glu Ser Leu Lys Val Leu Asp Asp Lys Leu Ala Ala Ala Leu Lys
     1385                1390                1395
Val Tyr Asp Asp Asp Lys Val Ser Gln Asp Asp Val Asp Ala Ala
     1400                1405                1410
Glu Ala Ala Leu Ser Ala Ala Ile Asp Ala Leu Lys Thr Lys Pro
     1415                1420                1425
Thr Thr Pro Gly Gly Glu Gly Glu Lys Pro Gly Glu Gly Glu Lys
     1430                1435                1440
Pro Gly Asp Gly Asn Lys Pro Gly Asp Gly Lys Lys Pro Gly Asp
     1445                1450                1455
```

-continued

```
Val Ile Ala Lys Thr Gly Ala  Ser Thr Met Gly Val  Val Phe Ala
    1460            1465                 1470

Ala Leu Ala Met Val Ala Gly  Ala Val Val Thr Leu  Glu Ala Lys
    1475            1480                 1485

Arg Lys  Ser Asn Arg
    1490

<210> SEQ ID NO 5
<211> LENGTH: 478
<212> TYPE: PRT
<213> ORGANISM: Bifidobacterium longum
<220> FEATURE:
<223> OTHER INFORMATION: Alpha-1,3/4-fucosidase, putative
      Bifidobacterium longum subsp. infantis ATCC 15697=JCM 1222
<300> PUBLICATION INFORMATION:
<308> DATABASE ACCESSION NUMBER: gi 213524647
<300> PUBLICATION INFORMATION:
<308> DATABASE ACCESSION NUMBER: ACJ53394.1

<400> SEQUENCE: 5

Met Asn Asn Pro Ala Asp Ala Gly Ile Asn Leu Asn Tyr Leu Ala Asn
1                5                  10                  15

Val Arg Pro Ser Ser Arg Gln Leu Ala Trp Gln Arg Met Glu Met Tyr
            20                  25                  30

Ala Phe Leu His Phe Gly Met Asn Thr Met Thr Asp Arg Glu Trp Gly
        35                  40                  45

Leu Gly His Glu Asp Pro Ala Leu Phe Asn Pro Arg Asn Val Asp Val
    50                  55                  60

Asp Gln Trp Met Asp Ala Leu Val Ala Gly Met Ala Gly Val Ile
65                  70                  75                  80

Leu Thr Cys Lys His His Asp Gly Phe Cys Leu Trp Pro Ser Arg Leu
                85                  90                  95

Thr Arg His Thr Val Ala Ser Ser Pro Trp Arg Glu Gly Lys Gly Asp
            100                 105                 110

Leu Val Arg Glu Val Ser Glu Ser Ala Arg Arg His Gly Leu Lys Phe
        115                 120                 125

Gly Val Tyr Leu Ser Pro Trp Asp Arg Thr Glu Glu Ser Tyr Gly Lys
    130                 135                 140

Gly Lys Ala Tyr Asp Asp Phe Tyr Val Gly Gln Leu Thr Glu Leu Leu
145                 150                 155                 160

Thr Gln Tyr Gly Pro Ile Phe Ser Val Trp Leu Asp Gly Ala Asn Gly
                165                 170                 175

Glu Gly Lys Asn Gly Lys Thr Gln Tyr Tyr Asp Trp Asp Arg Tyr Tyr
            180                 185                 190

Asn Val Ile Arg Ser Leu Gln Pro Asp Ala Val Ile Ser Val Cys Gly
        195                 200                 205

Pro Asp Val Arg Trp Ala Gly Asn Glu Ala Gly His Val Arg Asp Asn
    210                 215                 220

Glu Trp Ser Val Val Pro Arg Arg Leu Arg Ser Ala Glu Leu Thr Met
225                 230                 235                 240

Glu Lys Ser Gln Gln Glu Asp Asp Ala Ser Phe Ala Thr Thr Val Ser
                245                 250                 255

Ser Gln Asp Asp Asp Leu Gly Ser Arg Glu Ala Val Ala Gly Tyr Gly
            260                 265                 270

Asp Asn Val Cys Trp Tyr Pro Ala Glu Val Asp Thr Ser Ile Arg Pro
        275                 280                 285
```

```
Gly Trp Phe Tyr His Gln Ser Glu Asp Asp Lys Val Met Ser Ala Asp
            290                 295                 300

Gln Leu Phe Asp Leu Trp Leu Ser Ala Val Gly Gly Asn Ser Ser Leu
305                 310                 315                 320

Leu Leu Asn Ile Pro Pro Ser Pro Glu Gly Leu Leu Ala Glu Pro Asp
                325                 330                 335

Val Gln Ser Leu Lys Gly Leu Gly Arg Arg Val Ser Glu Phe Arg Glu
            340                 345                 350

Ala Leu Ala Ser Val Arg Cys Glu Ala Arg Thr Ser Ser Ala Ser Ala
            355                 360                 365

Ala Ala Ala His Leu Val Asp Gly Asn Arg Asp Thr Phe Trp Arg Pro
370                 375                 380

Asp Ala Asp Asp Ala Ala Pro Ala Ile Thr Leu Thr Leu Pro Gln Pro
385                 390                 395                 400

Thr Thr Ile Asn Ala Ile Val Ile Glu Glu Ala Ile Glu His Gly Gln
                405                 410                 415

Arg Ile Glu His Leu Arg Val Thr Gly Ala Leu Pro Asp Gly Thr Glu
            420                 425                 430

Arg Val Leu Gly Gln Ala Gly Thr Val Gly Tyr Arg Arg Ile Leu Arg
            435                 440                 445

Phe Asp Asp Val Glu Val Ser Ser Val Thr Leu His Val Asp Gly Ser
450                 455                 460

Arg Leu Ala Pro Met Ile Ser Arg Ala Ala Ala Val Arg Ile
465                 470                 475

<210> SEQ ID NO 6
<211> LENGTH: 378
<212> TYPE: PRT
<213> ORGANISM: Lactobacillus casei
<220> FEATURE:
<223> OTHER INFORMATION: Alpha-L-fucosidase [Lactobacillus casei BL23]
<300> PUBLICATION INFORMATION:
<308> DATABASE ACCESSION NUMBER: gi 190713109
<300> PUBLICATION INFORMATION:
<308> DATABASE ACCESSION NUMBER: CAQ67115.1

<400> SEQUENCE: 6

Met Thr Lys Pro Ser Ala Val Asn Ile His Arg Thr Asn Pro Pro Asp
1               5                   10                  15

Trp Phe Lys Gln Ala Asp Phe Gly Ile Ile His Trp Gly Pro Tyr
            20                  25                  30

Ser Val Pro Ala Tyr Ala Pro Val Asn Ile Pro Asp Tyr Gly Thr Leu
            35                  40                  45

Ile Lys Thr Lys Ser Leu Gly Tyr Leu Phe Glu His Gln Pro Tyr Ala
50                  55                  60

Glu Trp Tyr Gly Asn Ser Met Leu Leu Pro Ser Pro Val Ala Ala
65                  70                  75                  80

Tyr His Arg Thr His Tyr Gly Asn Thr Ser Tyr Ala Asp Phe Ala Lys
                85                  90                  95

Thr Phe Lys Gln Thr Ala Gln Asn Val Asp Val Gln Ala Trp Ala Ala
            100                 105                 110

Ala Phe Ala Asn Ala Gly Ala Lys Tyr Val Val Ile Val Thr Lys His
            115                 120                 125

His Asp Gly Phe Val Met Phe Asp Pro His Thr Lys Asn Pro Tyr Glu
130                 135                 140

Pro Asp Tyr His Leu Asn Phe Asp Phe Val Gly Glu Leu Ala Gln Ala
145                 150                 155                 160
```

```
Val Arg Ala His Gly Met Arg Phe Gly Thr Tyr Tyr Ser Ser Leu Leu
                165                 170                 175

Asp Trp Thr Phe Pro His Leu Pro Ile Lys Asp Tyr Gly Ser Phe Leu
            180                 185                 190

Leu Gly Asn Asp Lys Ser Gln Thr Tyr Lys Asp Tyr Val Trp His Gln
        195                 200                 205

Trp His Glu Leu Ile Asp Arg Tyr His Pro Asp Val Leu Trp Asn Asp
    210                 215                 220

Ile Gly Tyr Pro Asp Asp His Arg Leu Glu Thr Leu Phe Lys Tyr Tyr
225                 230                 235                 240

Tyr Gln Gln Val Pro Glu Gly Leu Val Asn Asp Arg Trp Gln Gln Phe
                245                 250                 255

Pro Asp Trp Met Arg Thr Ser Trp Ile Arg Pro Ile Phe Asn Leu Val
            260                 265                 270

Ala Ala Gln Val Ile Lys Arg Asp Gln His His Ser Asn Asp Leu Ser
        275                 280                 285

Glu Val Lys Tyr Tyr Asp Tyr Arg Thr Phe Glu Tyr Arg Thr Asp Trp
    290                 295                 300

Pro Gln Thr Asn Arg Tyr Phe Glu Met Thr Arg Gly Met Asp Lys Ser
305                 310                 315                 320

Phe Gly Tyr Asn Arg Leu Ser Arg Pro Glu Asp Tyr Ile Thr Ala Asp
                325                 330                 335

Asp Ile Lys Gln Leu Ile Ala Glu Leu Arg Ser Lys Arg Gly Arg Leu
            340                 345                 350

Leu Leu Asn Val Gly Pro Asp Met Asn Gly Ile Pro Ser Ala Gln
        355                 360                 365

Leu Ser Ile Leu Gln Gln Leu Ser Asp Arg
    370                 375
```

<210> SEQ ID NO 7
<211> LENGTH: 414
<212> TYPE: PRT
<213> ORGANISM: Lactobacillus casei
<220> FEATURE:
<223> OTHER INFORMATION: Alpha-L-fucosidase [Lactobacillus casei BL23]
<300> PUBLICATION INFORMATION:
<308> DATABASE ACCESSION NUMBER: gi 190713871
<300> PUBLICATION INFORMATION:
<308> DATABASE ACCESSION NUMBER: CAQ67877.1

<400> SEQUENCE: 7

```
Met Thr Glu Pro Leu Pro Arg Ile Gln His Tyr Glu Asp Leu Gly Leu
1               5                   10                  15

Gly Leu Phe Ile His Trp Gly Leu Tyr Ser Gln Met Ala Val Gly Glu
            20                  25                  30

Trp Thr Glu Leu Ile His His Arg Asn Gln His Asp Tyr Glu Gln Leu
        35                  40                  45

Ile Lys Thr Phe Thr Ala Ala Gln Phe Asp Ala Lys Lys Ile Ala His
    50                  55                  60

Ala Ala Lys Ala Val Gly Ala Lys Tyr Ile Val Leu Thr Thr Lys His
65                  70                  75                  80

His Glu Gly Phe Phe Leu Tyr Asp Thr Lys Gly Leu Ser Asp Phe Asp
                85                  90                  95

Val Met His Ala Pro Ala Arg Arg Asp Leu Ile Ala Glu Phe Val Ala
            100                 105                 110

Ala Cys Arg Glu Glu Asp Leu Leu Pro Phe Phe Tyr Met Ala Thr Tyr
```

```
            115                 120                 125
Asp Trp His Thr Pro Leu Tyr Asp Asp Phe Pro Ala Tyr Leu Thr
            130                 135                 140
Tyr Leu Gln Lys Ser Val Glu Val Leu Cys Arg Asn Tyr Gly Pro Val
145                 150                 155                 160
Gly Gly Phe Trp Phe Asp Gly Asn Trp Lys Lys Asp Ala Asp Trp
                165                 170                 175
His Leu Pro Glu Leu Tyr Gly Met Ile Arg His Tyr Gln Pro Asn Ala
                180                 185                 190
Ile Ile Val Asn Asn Thr Gly Leu Lys Asn Arg Gly Gln Val Ser Asp
                195                 200                 205
Pro Glu Ile Asp Val Val Thr Tyr Glu Arg Arg Thr Pro Asp Glu Ile
                210                 215                 220
Tyr His Gly Ala Pro Asn Glu Lys Tyr Val Ala Gly Glu Ile Ser Ile
225                 230                 235                 240
Thr Leu Asn Gln His Trp Gly Ile Ala Ala Asn Asp Leu Asn Tyr Lys
                245                 250                 255
Ser Pro Ala Glu Val Ile Glu Thr Val Ala His Ala Arg His Ile Gly
                260                 265                 270
Ala Asn Ile Leu Val Asn Ile Gly Leu Thr Gly Thr Gly Ala Ile Pro
            275                 280                 285
Ala Ala Ala Gln Thr Tyr Met His Leu Leu Gly Arg Trp Thr Ala Met
            290                 295                 300
Ala Ala Pro Val Leu Tyr Lys Gly Arg Pro Val Pro Val Thr Ser Ala
305                 310                 315                 320
His Gly Thr Arg Asp Phe Val Leu His Thr Ser Lys His Asp Phe Leu
                325                 330                 335
Cys Ile Leu Asp Leu Gln Val Val Gly Asn Asp Asn Val Val Leu Gly
            340                 345                 350
Gly Glu Gly Val Asn Pro Arg Ser Phe Val Gly Ile Gly Gln Pro Ile
            355                 360                 365
Gln Arg Ile His Trp Leu Asp Asn Asp Glu Val Leu Ser Phe Thr Gln
            370                 375                 380
Asp Leu Asp Lys Lys Val Leu Thr Val Asp Ala Thr Gly Tyr Pro Tyr
385                 390                 395                 400
Gly Ser Asp Trp Val Val Arg Ile Ala Gln Ile Asp Tyr Glu
                    405                 410

<210> SEQ ID NO 8
<211> LENGTH: 344
<212> TYPE: PRT
<213> ORGANISM: Lactobacillus casei
<220> FEATURE:
<223> OTHER INFORMATION: Alpha-L-fucosidase [Lactobacillus casei BL23]
<300> PUBLICATION INFORMATION:
<308> DATABASE ACCESSION NUMBER: gi 190713978
<300> PUBLICATION INFORMATION:
<308> DATABASE ACCESSION NUMBER: CAQ67984.1

<400> SEQUENCE: 8

Met Asn Asp Asn Val Ala Trp Phe Lys Gln Ala Lys Tyr Gly Met Met
1               5                   10                  15
Ile His Trp Gly Leu Tyr Ser Leu Leu Ala Gly Glu Tyr Arg Gly Glu
                20                  25                  30
Ser Ser Ser Ala Tyr Ala Glu Trp Ile Gln Ser Lys Phe Gln Ile Pro
            35                  40                  45
```

```
Asn Ala Glu Tyr Gly Asn Leu Ala Thr Ala Phe Asn Pro Leu Tyr Phe
    50                  55                  60

Asp Ala Lys Lys Ile Val Ala Leu Ala Lys Gln Cys Gly Met Gln Tyr
65                  70                  75                  80

Leu Val Val Thr Thr Lys His His Asp Gly Phe Ala Met Tyr His Ser
                85                  90                  95

Lys Val Asp Ala Tyr Asn Val Tyr Asp Ala Thr Pro Phe His Arg Asp
            100                 105                 110

Ile Ile Gly Glu Leu Ala Glu Ala Cys Gln Lys Ala Gly Leu Lys Phe
            115                 120                 125

Gly Leu Tyr Tyr Ser Gln Asp Leu Asp Trp His Asp Pro Asn Gly Gly
        130                 135                 140

Gly Tyr Lys Ser Asn Asp Val Glu Thr Ala Gly Thr Thr Trp Asp Asn
145                 150                 155                 160

Ser Trp Asp Phe Pro Asp Glu Asp Gln Lys Asn Phe Asp Leu Cys Phe
                165                 170                 175

Asp Asn Lys Ile Leu Pro Gln Ile Lys Glu Ile Met Ser Asn Tyr Gly
            180                 185                 190

Asp Ile Ala Thr Ala Trp Phe Asp Val Pro Met Thr Leu Ser Glu Ala
        195                 200                 205

Gln Ser Gln Thr Ile Tyr Asp Thr Val Arg Glu Leu Gln Pro Asn Cys
    210                 215                 220

Leu Ile Asn Ser Arg Leu Gly Asn Gly Lys Tyr Asp Phe Val Ser Leu
225                 230                 235                 240

Gly Asp Asn Glu Ile Pro Lys Asn Lys Glu Asp Met Asn Lys Thr Asp
                245                 250                 255

Val Asp Tyr Asn Glu Ile Thr Gly Phe Lys Pro Ser Pro Leu Gly Leu
            260                 265                 270

Tyr Glu Thr Ala Gly Thr Ile Asn Asp Ser Trp Gly Phe Ser Tyr His
        275                 280                 285

Asp Gln Asn Trp Lys Thr Pro Arg Thr Leu Tyr Arg Tyr Lys Gln His
    290                 295                 300

Leu Asn Asp Phe Gly Ile Asn Tyr Leu Leu Asn Val Gly Leu Asp Pro
305                 310                 315                 320

Leu Gly Arg Val Pro Met Met Ala Glu Glu Asn Leu Leu Ala Ala Lys
                325                 330                 335

Ala Leu Glu Asp Glu Ala Asn Arg
            340

<210> SEQ ID NO 9
<211> LENGTH: 1795
<212> TYPE: PRT
<213> ORGANISM: Bifidobacterium bifidum
<220> FEATURE:
<223> OTHER INFORMATION: Exo-alpha-sialidase [Bifidobacterium bifidum
      PRL2010]
<300> PUBLICATION INFORMATION:
<308> DATABASE ACCESSION NUMBER: gi 310867437
<300> PUBLICATION INFORMATION:
<308> DATABASE ACCESSION NUMBER: ADP36806.1

<400> SEQUENCE: 9

Met Thr Thr Ile Phe Arg Arg Ala Thr Ala Lys Thr Leu Met Arg Lys
1               5                   10                  15

Leu Ser Gly Leu Leu Val Ala Ile Ala Met Leu Ala Val Leu Pro Ala
            20                  25                  30

Gly Thr Ile Ser Ala Asn Ala Ala Asp Glu Pro Pro Gln Glu Tyr Leu
```

-continued

```
             35                  40                  45
Gln Leu Thr Leu Thr Arg Thr Asp Ser Asn Gly Thr Pro Ala Glu Val
 50                  55                  60
Gly Asp Lys Leu Thr Tyr Ser Leu Gly Tyr Lys Asn Val Ser Asp Thr
 65                  70                  75                  80
Gly Phe Ile Val His Pro Thr Ala Ser Asn Leu Asn Asn Val Ala Thr
                     85                  90                  95
Pro Gln Ser Ala Ser Asn Pro Asn Pro Met Cys Arg Trp Gly Asn Leu
                100                 105                 110
Ala Ala Gly Ala Ser Ala Ala Cys Thr Trp Ser Ala Ser Lys Glu Phe
                115                 120                 125
Ala Tyr His Val Val Thr Glu Asp Val Ala Asn Gly Phe Thr Pro
                130                 135                 140
Thr Ala Thr Val Ser Ala Thr Thr Gln Asp Gly Thr Asn Gly Val Leu
145                 150                 155                 160
Gln Ser Val Asp Ile Thr Gly Glu Thr Val Pro Ala Val Pro Ala Thr
                    165                 170                 175
Ser Thr Leu Arg Val Ala Met Gln Arg Thr Asp Thr Leu Gly Asp Asn
                180                 185                 190
Val Lys Ile Gly Asp Arg Leu Thr Phe Asn Phe Thr Tyr Thr Asn Lys
                195                 200                 205
Thr Ala Gln Lys Ile Tyr Ala Tyr Pro Ser Glu Ser Asn Ile Glu Arg
210                 215                 220
Val Asp Val Val Ser Phe Pro Arg Asn Ser Cys Arg Ser Gly Val Glu
225                 230                 235                 240
Ala Asn Gln Thr Ala Ser Cys Gly Phe Ala Tyr His Val Ile Thr Ala
                    245                 250                 255
Glu Asp Val Val Ala Arg Arg Tyr Thr Pro Thr Ala Thr Phe Arg Ala
                260                 265                 270
Thr Ser Asp Arg Asp Gly Thr Gln Val Leu Gln Asp Met Thr Phe
                275                 280                 285
Thr Thr Gly Thr Val Thr Val Ala Gly Pro Ala Asp Asp Ala Ala Ser
                290                 295                 300
Thr Pro Thr Glu Arg Lys Asp Gly Glu Pro Leu Leu Leu Ala Thr Asn
305                 310                 315                 320
Lys Gln Ile Gly Asn Thr Asp Tyr Tyr Arg Ile Pro Ala Ile Ala Gln
                    325                 330                 335
Ala Pro Asn Gly Trp Ile Leu Ala Ala Trp Asp Leu Arg Pro Lys Leu
                340                 345                 350
Ala Ala Asp Ala Pro Asn Pro Asn Ser Ile Val Gln Arg Ile Ser Lys
                355                 360                 365
Asp Gly Gly Lys Ser Trp Glu Thr Leu Ala Tyr Val Ala Gln Gly Arg
                370                 375                 380
Ser Ala Thr Asn Lys Tyr Gly Tyr Ser Asp Pro Ser Tyr Val Val Asp
385                 390                 395                 400
Glu Glu Ala Gly Lys Ile Phe Leu Phe Cys Val Lys Ser Tyr Asp Gln
                    405                 410                 415
Gly Tyr Phe Gly Ser Val Leu Gly Val Glu Asp Ala Arg Asn Val Leu
                420                 425                 430
Gln Ala Val Val Met Glu Ser Asp Asn Gly Ala Thr Trp Ser Glu
                435                 440                 445
Pro Arg Asn Ile Thr Lys Asp Ile Thr Lys Gly His Glu Asp Glu Trp
450                 455                 460
```

```
Lys Ser Arg Phe Ala Ser Ser Gly His Gly Ile Gln Leu Lys Tyr Gly
465                 470                 475                 480

Gln Tyr Lys Gly Arg Leu Ile Gln Gln Tyr Ala Val Arg Thr Thr Ser
                485                 490                 495

Asn Thr Asn Ile Ala Val Ser Val Tyr Ser Asp Asp His Gly Lys Thr
                500                 505                 510

Trp Lys Ala Gly Asn Pro Val Thr Glu Ala Asn Met Asp Glu Asn Lys
                515                 520                 525

Val Val Glu Leu Ser Asp Gly Arg Val Met Leu Asn Ser Arg Pro Gly
                530                 535                 540

Ala Ala Gly Tyr Arg Arg Val Ala Ile Ser Glu Asp Gly Gly Val Asn
545                 550                 555                 560

Tyr Gly Pro Ile Lys Ser Glu Thr Gln Leu Pro Asp Pro Asn Asn Asn
                565                 570                 575

Ala Gln Ile Thr Arg Ala Phe Pro Asn Ala Pro Glu Gly Ser Ala Lys
                580                 585                 590

Ala Lys Val Leu Leu Tyr Ser Ala Pro Arg Ala Ser Asn Glu Gly Arg
                595                 600                 605

Ala Asn Gly Val Val Arg Val Ser Phe Asp Asp Gly Thr Thr Trp Ser
610                 615                 620

Ala Gly Lys Leu Phe Lys Glu Gly Ser Met Ala Tyr Ser Val Ile Thr
625                 630                 635                 640

Ala Leu Asn Asp Ala Ala Gly Gly Tyr Gly Leu Leu Tyr Glu Gly
                645                 650                 655

Glu Ser Ile Thr Tyr Thr Arg Val Ser Met Glu Trp Leu Gly Tyr Leu
                660                 665                 670

Thr Ala Thr Ala Ser Gly Thr Ala Thr Val Lys Glu Gly Glu Gly Thr
                675                 680                 685

Leu Thr Ala Pro Val Thr Val Thr Asn Asp Gly Leu Thr Asp Tyr Thr
                690                 695                 700

Asn Val Thr Val Thr Pro Thr Gly Leu Pro Ser Gly Trp Ser Ala Glu
705                 710                 715                 720

Ala Val Asn Val Gly Asn Leu Ala Ala Gly Gln Ser Ala Thr Val Asn
                725                 730                 735

Val Pro Val Thr Val Pro Ala Ala Val Ser Gly Thr Val Ala Lys
                740                 745                 750

Ala Thr Met Lys Ile Thr Gly Lys Tyr Ala Gln Ser Glu Asp Thr Leu
                755                 760                 765

His Ser Phe Ala Glu Gly Glu Leu Ala Val Thr Val Thr Glu Pro Asp
                770                 775                 780

Pro Ala Ala Lys Arg Leu Lys Leu Thr Ile Glu Arg Thr Asp Asp Asn
785                 790                 795                 800

Gly Ala Pro Val Lys Val Gly Asp Thr Leu Thr Tyr Arg Ile Thr Tyr
                805                 810                 815

Glu Asn Val Gly Thr Gln Ser Phe Ala Val Tyr Pro Arg Lys Ser Asn
                820                 825                 830

Leu Asp Gly Val Thr Thr Pro Gln Ser Ala Ser Asn Pro Ala Pro Val
                835                 840                 845

Cys Arg Trp Ser Arg Leu Asp Pro Gly Thr Thr Gly Ala Cys Val Ser
                850                 855                 860

Gly Asn Gly Lys Arg Leu Ala Tyr His Thr Val Thr Glu Ala Asp Ala
865                 870                 875                 880
```

```
Thr Ala Gly Ser Phe Thr Pro Ser Ala Thr Ile Asp Ala Thr Ala Asp
                885                 890                 895

Thr Ser Gly Glu Thr Val Leu Glu Ser Val Ser Ile Thr Gly Asp Pro
            900                 905                 910

Val Thr Val Ser Gln Pro Val Glu Leu Pro Ala Asp Ile Ala Ala Trp
            915                 920                 925

Lys Thr Arg Asn Glu Ala Leu Asp Asp Trp Gln Thr Leu Ser Glu Lys
            930                 935                 940

Leu Ala Lys Thr Asp Arg Ile Asn Trp Leu Phe Thr Gly Asp Ser Ile
945                 950                 955                 960

Thr His Gly Val Gln Leu Thr Arg Gly Tyr Arg Thr Tyr Ser Glu Leu
                965                 970                 975

Phe Ala Asn His Leu Asp Thr Ala Ser Val Arg Gly Val Ser Arg Ala
                980                 985                 990

Asn Asp Val Val Met Asn Thr Gly Ile Ser Ser Ala Asp Ala Ser Trp
                995                 1000                1005

Pro Leu Lys Asp Gly Ala Phe Glu Lys Trp Val Ser Asp Lys His
    1010                1015                1020

Pro Asp Val Val Phe Leu Thr Phe Gly Met Asn Asp Gly Arg Thr
    1025                1030                1035

Gly Gln Ala Phe Thr Val Asp Gln Tyr Thr Ala Asn Leu Ser Thr
    1040                1045                1050

Leu Ile Asp Lys Ile Arg Asp Leu Gly Ala Ile Pro Val Leu Gln
    1055                1060                1065

Thr Gln Asn Tyr Thr Thr Asn Thr Thr Phe Asn Ala Asn Leu Asp
    1070                1075                1080

Thr Tyr Phe Asp Ala Glu Arg Arg Leu Ala Leu Asp Lys Asn Val
    1085                1090                1095

Leu Leu Val Asp Phe Asn Lys Gln Trp Leu Glu Leu Gly Gly Gly
    1100                1105                1110

Asn Arg Glu Ser Gly Thr Tyr Met Gly Ala Gly Asn Asp Ile His
    1115                1120                1125

Pro Gly Glu Asn Gly His Ile Glu Trp Ala Lys Phe Thr Leu Gly
    1130                1135                1140

Ala Leu Asn Met Ile Ala Asn Asp Asp Pro Leu Ala Arg Trp Ser
    1145                1150                1155

Ser Ser Asp Thr Thr Leu Asp Lys Pro Thr Val Thr Val Asp Ala
    1160                1165                1170

Asp Gly Asn Gly Leu Lys Gly Ser Asp Gly Leu Glu Pro Ala Pro
    1175                1180                1185

Ala Ala Ala Lys Ser Val Gly Lys Phe Leu Ser Gly Ala Gln Tyr
    1190                1195                1200

Val Asp Leu Gly Gly Asp Val Val Ser Ala Val Ala Gly Lys Arg
    1205                1210                1215

Glu Ser Asn Val Thr Ile Arg Phe Arg Ala Ser Ala Thr Gly Gln
    1220                1225                1230

Pro Gln Thr Leu Phe Ser Leu Gly Asp Ser Asp Ser Ala Thr Arg
    1235                1240                1245

Ala Thr Val Arg Leu Ser Ala Thr Gly Leu Val Gln Phe Leu Asn
    1250                1255                1260

Ser Gly Asn Thr Gly Asp Phe Tyr Thr Val Gly Thr Asn Asp Leu
    1265                1270                1275

Ala Asp Gly Ala Trp His Thr Val Ser Val Asn Phe Val Ala Asn
```

-continued

```
            1280                1285                1290
Gly Phe Thr Ile Tyr Val Asp Gly Ala Ala Met Arg Ala Ile Ser
    1295                1300                1305
Gly Gly Ala Gly Thr Gln Leu Asn Val Pro Gly Ala Ile Thr Val
    1310                1315                1320
Asn Thr Ala Thr Ala Gly Ala Ile Arg Gly Ala Asp Ser Ala Gly
    1325                1330                1335
Gly Ala Gln Gln Leu Thr Gly Ile Val Asp Tyr Val Ala Ala Trp
    1340                1345                1350
Ser Arg Thr Leu Thr Asp Ala Glu Ala Lys Arg Ile Ser Ala Glu
    1355                1360                1365
Thr Ser Ala Val Ala Val Thr Lys Val Asp Ala Ala Val Asn Ala
    1370                1375                1380
Leu Gln Pro Ile Ile Ser Asp Thr Gly Ala Arg Lys Asn Ile Val
    1385                1390                1395
Phe Val Gly Gly Glu Thr Ile Glu Gly Gly Tyr Thr Asp His Leu
    1400                1405                1410
Ile Ala Lys Asn Ile Val Gln Leu Leu Asp Glu Arg Val Arg Trp
    1415                1420                1425
Glu Tyr Val Thr Gly Leu Ser Ala Thr Asp Arg Glu Leu Gln Arg
    1430                1435                1440
Ala Lys Phe Phe Val Ala Ala Gly Gln Gly Gly Leu Thr Ala Lys
    1445                1450                1455
Gln Met Asp Glu Asp Tyr Ala Ala Met Val Gly Glu Tyr Ser Pro
    1460                1465                1470
Asp Ile Leu Phe Leu Ala Pro Asp Leu Tyr Asp Ala Asp Gly Ile
    1475                1480                1485
Leu Ala Glu Ser Asp Ala Ala Ala Phe Ala Gly His Ile Arg Ser
    1490                1495                1500
Val Ala Ala Lys Ala Lys Glu Ala Gly Ala Lys Val Val Leu Val
    1505                1510                1515
Thr Pro Val Thr Val Arg Gly Gly Glu Asp Glu Tyr Ala Gly Ala
    1520                1525                1530
Met Arg Thr Val Ala Lys Glu Asp Asp Leu Pro Leu Ile Asp Ala
    1535                1540                1545
Gln Ala Trp Ile Gly Lys Val Val Ala Asp Ala Ser Val Lys
    1550                1555                1560
Thr Ala Trp Phe Asn Lys Ala Gly Gln Leu Asn Tyr Ala Gly His
    1565                1570                1575
Leu Gly Tyr Ala Arg Phe Met Met Arg Ser Leu Asp Leu Tyr Pro
    1580                1585                1590
Ser Asn Val Ser Gly Ser Arg Ile Ala Ser Leu Pro Tyr Asp Thr
    1595                1600                1605
Ala Asn Val Thr Leu Val Gly Ala Ser Glu Asn Gly Gly Glu Leu
    1610                1615                1620
Pro Val Gly Arg Val Glu Gly Thr Asp Arg Ala His Ile Asp Thr
    1625                1630                1635
Met Gln Ile Gly Ala Ala Ala Ser Leu Val Val Thr Asp Ser Tyr
    1640                1645                1650
Ala Val Tyr Glu Ile Gly Glu Asp Gly Gly Arg Thr Leu Val Ala
    1655                1660                1665
Asp Gly Leu Lys Pro Ala Asp Val Leu Ala Asp Gly Ile Asp Val
    1670                1675                1680
```

```
Thr Val Asn Asp Thr Ala Ala His Arg Tyr Glu Val Val Gly Ser
    1685                1690                1695

Ala Asn Val Pro Glu Gly Ala Asp Ala Val Thr Val Thr Tyr Thr
    1700                1705                1710

Ala Thr Leu Ala Ala Val Glu Glu Pro Glu Pro Gly Pro Asp Pro
    1715                1720                1725

Asp Pro Thr Pro Asp Pro Ser Glu Lys Pro Asp Gly Asp Gly Thr
    1730                1735                1740

Gly Asp Gly Thr Gly Ala Gly Ala Gly Asp Val Gln Lys Pro Thr
    1745                1750                1755

Pro Asp Ala Val Ala Lys Thr Gly Ala Asp Val Phe Gly Leu Leu
    1760                1765                1770

Ala Ala Val Ala Val Leu Leu Ala Ala Gly Gly Val Thr Leu Ser
    1775                1780                1785

Leu Arg Arg Arg Ala Asn Arg
    1790            1795

<210> SEQ ID NO 10
<211> LENGTH: 770
<212> TYPE: PRT
<213> ORGANISM: Bifidobacterium bifidum
<220> FEATURE:
<223> OTHER INFORMATION: Exo-alpha-sialidase [Bifidobacterium bifidum
      PRL2010]
<300> PUBLICATION INFORMATION:
<308> DATABASE ACCESSION NUMBER: gi 310867438
<300> PUBLICATION INFORMATION:
<308> DATABASE ACCESSION NUMBER: ADP36807.1

<400> SEQUENCE: 10

Met Val Arg Ser Thr Lys Pro Ser Leu Leu Arg Arg Phe Gly Ala Leu
1               5                   10                  15

Val Ala Ala Ala Ala Met Leu Val Val Leu Pro Ala Gly Val Ser Thr
                20                  25                  30

Ala Ser Ala Ala Ser Asp Asp Ala Asp Met Leu Thr Val Thr Met Thr
            35                  40                  45

Arg Thr Asp Ala Leu Gly Asp Glu Val Tyr Val Gly Asp Thr Leu Thr
        50                  55                  60

Tyr Ser Phe Thr Asn Thr Asn Thr Ser Ser Ala Phe Thr Ala Phe
65                  70                  75                  80

Pro Ala Glu Ser Asn Leu Ser Gly Val Leu Thr Thr Gly Thr Pro Asn
                85                  90                  95

Cys Arg Tyr Glu Asn Leu Ala Gly Gly Ala Ser Tyr Pro Cys Ser Thr
            100                 105                 110

Ala Ser His Thr Ile Thr Ala Asp Asp Leu Thr Ala Gly Ser Phe Thr
        115                 120                 125

Pro Arg Thr Val Trp Lys Ala Thr Ser Asp Arg Gly Gly Thr Gln Val
    130                 135                 140

Leu Gln Asp Asn Ile Val Ser Thr Gly Asp Thr Val Thr Val Lys Glu
145                 150                 155                 160

Gly Lys Arg Pro Asp Pro Ala Thr Ile Pro Thr Asp Arg Ala Asp Gly
                165                 170                 175

Glu Ala Val Arg Leu Ala Thr Ala Arg Gln Asn Leu Gly Thr Glu Cys
            180                 185                 190

Tyr Arg Ile Pro Ala Leu Ala Glu Ala Pro Asn Gly Trp Ile Leu Ala
        195                 200                 205
```

```
Ala Phe Asp Gln Arg Pro Asn Thr Ala Met Ala Asn Gly Ser Gly Val
210                 215                 220
Lys Cys Trp Asp Ala Pro Gln Pro Asn Ser Ile Val Gln Arg Ile Ser
225                 230                 235                 240
Lys Asp Gly Gly Lys Ser Trp Thr Pro Ile Gln Tyr Val Ala Gln Gly
                245                 250                 255
Lys Asn Ala Pro Glu Arg Tyr Gly Tyr Ser Asp Pro Ser Tyr Val Val
                260                 265                 270
Asp Lys Glu Thr Gly Glu Ile Phe Leu Phe Val His Ser Tyr Asn
            275                 280                 285
Lys Gly Phe Ala Asp Ser Gln Leu Gly Val Asp Glu Ser Asn Arg Asn
290                 295                 300
Val Leu His Ala Val Val Ser Ser Lys Asp Asn Gly Glu Thr Trp
305                 310                 315                 320
Ser Lys Pro Arg Asp Ile Thr Ala Asp Ile Thr Lys Gly Tyr Glu Asn
                325                 330                 335
Glu Trp Lys Ser Arg Phe Ala Thr Ser Gly Ala Gly Ile Gln Leu Lys
                340                 345                 350
Tyr Gly Lys Tyr Lys Gly Arg Leu Ile Gln Gln Tyr Ala Val Gly Arg
                355                 360                 365
Thr Thr Gly Ser Asn Ala Ala Val Ser Val Tyr Ser Asp Asp His Gly
    370                 375                 380
Lys Thr Trp Gln Ala Gly Asn Pro Val Thr Gly Met Leu Met Asp Glu
385                 390                 395                 400
Asn Lys Val Val Glu Leu Ser Asp Gly Arg Val Met Leu Asn Ser Arg
                405                 410                 415
Pro Gly Asn Gly Ser Gly Tyr Arg Arg Val Ala Ile Ser Glu Asp Gly
                420                 425                 430
Gly Val Asn Tyr Gly Thr Val Lys Asn Glu Thr Gln Leu Pro Asp Pro
            435                 440                 445
Asn Asn Asn Ala His Ile Thr Arg Ala Phe Pro Asn Ala Pro Glu Gly
        450                 455                 460
Ser Ala Lys Ala Lys Val Leu Leu Tyr Ser Ser Pro Arg Ala Asn Asn
465                 470                 475                 480
Glu Gly Arg Ala Asn Gly Val Val Arg Ile Ser Leu Asp Asp Gly Thr
                485                 490                 495
Thr Trp Ser Ser Gly Lys Leu Tyr Lys Glu Gly Ser Met Ala Tyr Ser
            500                 505                 510
Val Ile Thr Ala Leu Ser Gly Ala Gly Gly Tyr Gly Leu Leu
        515                 520                 525
Tyr Glu Gly Ala Trp Val Thr Gly Gly Ile Asp Ser His Asp Ile
    530                 535                 540
Met Tyr Thr His Ile Ser Met Asp Trp Leu Gly Tyr Leu Ser Ala Thr
545                 550                 555                 560
Ala Asp Asp Val Thr Ala Ser Val Glu Glu Gly Ala Ser Thr Val Asp
                565                 570                 575
Val Thr Val Pro Val Ser Asn Val Gly Ser Val Asp Tyr Thr Gly Val
            580                 585                 590
Thr Val Thr Pro Ala Asp Leu Pro Thr Gly Trp Ser Ala Ser Pro Val
        595                 600                 605
Asn Val Gly Ala Leu Ala Ser Gly Ala Ser Lys Asp Val Thr Val Thr
    610                 615                 620
Val Asn Val Pro Ala Thr Ala Lys Lys Asp Asp Val Ala Lys Ile Val
```

```
             625                 630                 635                 640
Leu Arg Val Thr Gly Thr Ser Ala Ala Asn Ala Asn Ala Thr Thr Gly
                    645                 650                 655

Phe Asp Gly Ser Ile Thr Val Asn Val Thr Glu Lys Ser Glu Pro Asp
                    660                 665                 670

Pro Glu Pro Glu Pro Thr Ile Thr Gly Val Ser Ala Val Thr Ser Gln
                    675                 680                 685

Ala Gly Val Lys Val Gly Asp Val Phe Asp Ala Ser Lys Val Ser Val
                    690                 695                 700

Thr Ala Ala Met Ser Asp Gly Ser Ser Lys Ala Leu Ala Ala Gly Glu
705                 710                 715                 720

Tyr Ser Leu Ser Ala Val Asp Ala Asp Gly Lys Ala Val Asp Leu Ala
                    725                 730                 735

Glu Pro Phe Ala Ala Ala Gly Val Val Thr Val Thr Val Ser Val Pro
                    740                 745                 750

Val Glu Gly Ala Asp Pro Leu Thr Ala Ser Phe Thr Ile Asp Val Ala
                    755                 760                 765

Glu Lys
    770

<210> SEQ ID NO 11
<211> LENGTH: 836
<212> TYPE: PRT
<213> ORGANISM: Bifidobacterium bifidum
<220> FEATURE:
<223> OTHER INFORMATION: Sialidase [Bifidobacterium bifidum S17]
<300> PUBLICATION INFORMATION:
<308> DATABASE ACCESSION NUMBER: gi 309252191
<300> PUBLICATION INFORMATION:
<308> DATABASE ACCESSION NUMBER: ADO53939.1

<400> SEQUENCE: 11

Met Val Arg Ser Thr Lys Pro Ser Leu Leu Arg Arg Leu Gly Ala Leu
1               5                   10                  15

Val Ala Ala Ala Met Leu Val Val Leu Pro Ala Gly Val Ser Thr
                20                  25                  30

Ala Ser Ala Ala Ser Asp Asp Ala Asp Met Leu Thr Val Thr Met Thr
                35                  40                  45

Arg Thr Asp Thr Leu Gly Asp Glu Val Tyr Val Gly Asp Thr Leu Thr
        50                  55                  60

Tyr Ser Phe Thr Asn Thr Asn Asn Thr Ser Ser Ala Phe Thr Ala Phe
65              70                  75                  80

Pro Ala Glu Ser Asn Leu Ser Gly Val Leu Thr Thr Gly Thr Pro Asn
                85                  90                  95

Cys Arg Tyr Glu Asn Leu Ala Gly Gly Ala Ser Tyr Pro Cys Ser Thr
                100                 105                 110

Ala Ser His Thr Ile Thr Ala Asp Asp Leu Thr Ala Gly Ser Phe Thr
                115                 120                 125

Pro Arg Thr Val Trp Lys Ala Thr Ser Asp Arg Gly Gly Thr Gln Val
                130                 135                 140

Leu Gln Asp Asn Ile Val Ser Thr Gly Asp Thr Val Thr Val Lys Glu
145                 150                 155                 160

Gly Lys Arg Pro Asp Pro Ala Thr Ile Pro Thr Asp Arg Ala Asp Gly
                165                 170                 175

Glu Ala Val Arg Leu Ala Thr Ala Arg Gln Asn Leu Gly Thr Glu Cys
                180                 185                 190
```

```
Tyr Arg Ile Pro Ala Leu Ala Glu Ala Pro Asn Gly Trp Ile Leu Ala
        195                 200                 205

Ala Phe Asp Gln Arg Pro Asn Thr Ala Met Ala Asn Gly Ser Gly Val
210                     215                 220

Lys Cys Trp Asp Ala Pro Gln Pro Asn Ser Ile Val Gln Arg Ile Ser
225                 230                 235                 240

Lys Asp Gly Gly Lys Ser Trp Thr Pro Ile Gln Tyr Val Ala Gln Gly
                245                 250                 255

Lys Asn Ala Pro Glu Arg Tyr Gly Tyr Ser Asp Pro Ser Tyr Val Val
            260                 265                 270

Asp Glu Glu Thr Gly Glu Ile Phe Leu Phe Val His Ser Tyr Asn
        275                 280                 285

Lys Gly Phe Ala Asp Ser Gln Leu Gly Val Asp Glu Ser Asn Arg Asn
290                     295                 300

Val Leu His Ala Val Val Ser Ser Lys Asp Asn Gly Glu Thr Trp
305                 310                 315                 320

Ser Lys Pro Arg Asp Ile Thr Ala Asp Ile Thr Lys Gly Tyr Glu Asn
                325                 330                 335

Glu Trp Lys Ser Arg Phe Ala Thr Ser Gly Ala Gly Ile Gln Leu Lys
            340                 345                 350

Tyr Gly Lys Tyr Lys Gly Arg Leu Ile Gln Gln Tyr Ala Val Gly Arg
        355                 360                 365

Thr Thr Gly Ser Asn Ala Ala Val Ser Val Tyr Ser Asp Asp His Gly
    370                 375                 380

Lys Thr Trp Gln Ala Gly Asn Pro Val Thr Gly Met Leu Met Asp Glu
385                 390                 395                 400

Asn Lys Val Val Glu Leu Ser Asp Gly His Val Met Leu Asn Ser Arg
                405                 410                 415

Pro Gly Asn Gly Ser Gly Tyr Arg Arg Val Ala Ile Ser Glu Asp Gly
            420                 425                 430

Gly Val Asn Tyr Gly Thr Val Lys Asn Glu Thr Gln Leu Pro Asp Pro
        435                 440                 445

Asn Asn Asn Ala His Ile Thr Arg Ala Phe Pro Asn Ala Pro Glu Gly
    450                 455                 460

Ser Ala Lys Ala Lys Val Leu Leu Tyr Ser Ser Pro Arg Ala Asn Asn
465                 470                 475                 480

Glu Gly Arg Ala Asn Gly Val Val Arg Ile Ser Leu Asp Asp Gly Thr
                485                 490                 495

Thr Trp Ser Ser Gly Lys Leu Tyr Lys Ala Gly Ser Met Ala Tyr Ser
            500                 505                 510

Val Ile Thr Ala Leu Ser Gly Ala Ala Gly Gly Tyr Gly Leu Leu
        515                 520                 525

Tyr Glu Gly Ala Trp Val Thr Gly Gly Ile Asp Ser His Asp Ile
    530                 535                 540

Met Tyr Thr His Ile Ser Met Asp Trp Leu Gly Tyr Leu Ser Ala Thr
545                 550                 555                 560

Ala Asp Asp Val Thr Ala Ser Val Glu Glu Gly Ala Ser Thr Val Asp
                565                 570                 575

Val Thr Val Pro Val Ser Asn Val Gly Ser Val Asp Tyr Thr Gly Val
            580                 585                 590

Thr Val Thr Pro Ala Asp Leu Pro Thr Gly Trp Ser Ala Ser Pro Val
        595                 600                 605

Asn Val Gly Ala Leu Ala Ser Gly Ala Ser Lys Asp Val Thr Val Thr
```

```
                610                 615                 620
Val Asn Val Pro Ala Thr Ala Lys Lys Asp Asp Val Ala Lys Ile Val
625                 630                 635                 640

Leu Arg Val Thr Gly Thr Ser Ala Ala Asn Ala Asp Ala Thr Thr Gly
                645                 650                 655

Phe Asp Gly Ser Ile Thr Val Asn Val Thr Glu Lys Ser Glu Pro Asp
            660                 665                 670

Pro Glu Pro Glu Pro Thr Ile Thr Gly Val Ser Ala Val Thr Ser Gln
        675                 680                 685

Ala Gly Val Lys Val Gly Asp Val Phe Asp Ala Ser Lys Val Ser Val
    690                 695                 700

Thr Ala Ala Met Ser Asp Gly Ser Ser Lys Ala Leu Ala Ala Gly Glu
705                 710                 715                 720

Tyr Ser Leu Ser Ala Val Asp Ala Asp Gly Lys Ala Val Asp Leu Ala
                725                 730                 735

Glu Pro Phe Ala Ala Ala Gly Val Val Thr Val Thr Val Ser Val Pro
            740                 745                 750

Val Glu Gly Ala Asp Pro Leu Thr Ala Ser Phe Thr Ile Asp Val Ala
        755                 760                 765

Glu Lys Ser Ala Asp Pro Glu Pro Lys Pro Glu Pro Glu Pro Lys Pro
    770                 775                 780

Glu Pro Glu Lys Pro Ala Gly Pro Lys Val Asp Val Pro Thr Glu Lys
785                 790                 795                 800

Pro Gly Leu Ser Lys Thr Gly Ala Ser Thr Ala Gly Met Ser Ile Val
                805                 810                 815

Phe Val Leu Leu Ala Leu Ser Gly Val Ala Ala Leu Ser Leu Arg Arg
            820                 825                 830

Arg Ser Val His
        835

<210> SEQ ID NO 12
<211> LENGTH: 1795
<212> TYPE: PRT
<213> ORGANISM: Bifidobacterium bifidum
<220> FEATURE:
<223> OTHER INFORMATION: Sialidase [Bifidobacterium bifidum S17]
<300> PUBLICATION INFORMATION:
<308> DATABASE ACCESSION NUMBER: gi 309252190
<300> PUBLICATION INFORMATION:
<308> DATABASE ACCESSION NUMBER: ADO53938.1

<400> SEQUENCE: 12

Met Thr Thr Ile Phe Arg Arg Ala Thr Ala Lys Thr Leu Met Arg Lys
1               5                   10                  15

Leu Ser Gly Leu Leu Val Ala Ile Ala Met Leu Ala Val Leu Pro Ala
                20                  25                  30

Gly Thr Ile Ser Ala Asn Ala Ala Asp Glu Pro Pro Gln Glu Tyr Leu
            35                  40                  45

Gln Leu Thr Leu Thr Arg Thr Asp Ser Asn Gly Thr Pro Ala Glu Val
        50                  55                  60

Gly Asp Lys Leu Thr Tyr Ser Leu Gly Tyr Lys Asn Val Ser Asp Thr
65                  70                  75                  80

Gly Phe Ile Val His Pro Thr Ala Ser Asn Leu Asn Asn Val Ala Thr
                85                  90                  95

Pro Gln Ser Ala Ser Asn Pro Asn Pro Met Cys Arg Trp Gly Asn Leu
            100                 105                 110
```

```
Ala Ala Gly Ala Ser Ala Ala Cys Thr Trp Ser Ala Ser Lys Glu Phe
            115                 120                 125

Ala Tyr His Val Val Thr Glu Asp Val Ala Asn Gly Phe Thr Pro
    130                 135                 140

Thr Ala Thr Val Ser Ala Thr Thr Gln Asp Gly Thr Asn Gly Val Leu
145                 150                 155                 160

Gln Ser Val Asp Ile Thr Gly Glu Thr Val Pro Ala Val Pro Ala Thr
                165                 170                 175

Ser Thr Leu Arg Val Ala Met Gln Arg Thr Asp Thr Leu Gly Asp Asn
            180                 185                 190

Val Lys Ile Gly Asp Arg Leu Thr Phe Asn Phe Thr Tyr Thr Asn Lys
            195                 200                 205

Thr Ala Gln Lys Ile Tyr Ala Tyr Pro Ser Glu Ser Asn Ile Glu Arg
    210                 215                 220

Val Asp Val Val Ser Phe Pro Arg Asn Ser Cys Arg Ser Gly Val Glu
225                 230                 235                 240

Ala Asn Gln Thr Ala Ser Cys Gly Phe Ala Tyr His Val Ile Thr Ala
                245                 250                 255

Glu Asp Val Val Ala Arg Arg Tyr Thr Pro Thr Ala Thr Phe Arg Ala
            260                 265                 270

Thr Ser Asp Arg Asp Gly Thr Gln Val Leu Gln Asp Met Thr Phe
    275                 280                 285

Thr Thr Gly Thr Val Thr Val Ala Gly Pro Ala Asp Ala Ala Ser
            290                 295                 300

Thr Pro Thr Glu Arg Lys Asp Gly Glu Pro Leu Leu Leu Ala Thr Asn
305                 310                 315                 320

Lys Gln Ile Gly Asn Thr Asp Tyr Tyr Arg Ile Pro Ala Ile Ala Gln
                325                 330                 335

Ala Pro Asn Gly Trp Ile Leu Ala Ala Trp Asp Leu Arg Pro Lys Leu
            340                 345                 350

Ala Ala Asp Ala Pro Asn Pro Asn Ser Ile Val Gln Arg Ile Ser Lys
            355                 360                 365

Asp Gly Gly Lys Ser Trp Glu Thr Leu Ala Tyr Val Ala Gln Gly Arg
370                 375                 380

Ser Ala Thr Asn Lys Tyr Gly Tyr Ser Asp Pro Ser Tyr Val Val Asp
385                 390                 395                 400

Glu Glu Ala Gly Lys Ile Phe Leu Phe Cys Val Lys Ser Tyr Asp Gln
                405                 410                 415

Gly Tyr Phe Gly Ser Val Leu Gly Val Glu Asp Ala Arg Asn Val Leu
            420                 425                 430

Gln Ala Val Val Met Glu Ser Asp Asn Gly Ala Thr Trp Ser Glu
    435                 440                 445

Pro Arg Asn Ile Thr Lys Asp Ile Thr Lys Gly His Glu Asp Glu Trp
    450                 455                 460

Lys Ser Arg Phe Ala Ser Ser Gly His Gly Ile Gln Leu Lys Tyr Gly
465                 470                 475                 480

Gln Tyr Lys Gly Arg Leu Ile Gln Gln Tyr Ala Val Arg Thr Ser
                485                 490                 495

Asn Thr Asn Ile Ala Val Ser Val Tyr Ser Asp His Gly Lys Thr
            500                 505                 510

Trp Lys Ala Gly Asn Pro Val Thr Glu Val Asn Met Asp Glu Asn Lys
            515                 520                 525

Val Val Glu Leu Ser Asp Gly Arg Val Met Leu Asn Ser Arg Pro Gly
```

530                 535                 540
Ala Ala Gly Tyr Arg Arg Val Ala Ile Ser Glu Asp Gly Val Asn
545                 550                 555                 560

Tyr Gly Pro Ile Lys Ser Glu Thr Gln Leu Pro Asp Pro Asn Asn Asn
                    565                 570                 575

Ala Gln Ile Thr Arg Ala Phe Pro Asn Ala Pro Glu Gly Ser Ala Lys
                580                 585                 590

Ala Lys Val Leu Leu Tyr Ser Ala Pro Arg Ala Ser Asn Glu Gly Arg
            595                 600                 605

Ala Asn Gly Val Val Arg Val Ser Phe Asp Asp Gly Thr Thr Trp Ser
        610                 615                 620

Ala Gly Lys Leu Phe Lys Ala Gly Ser Met Ala Tyr Ser Val Ile Thr
625                 630                 635                 640

Ala Leu Asn Asp Ala Ala Gly Gly Tyr Gly Leu Leu Tyr Glu Gly
                    645                 650                 655

Glu Ser Ile Thr Tyr Thr Arg Ala Ser Met Glu Trp Leu Gly Tyr Leu
                660                 665                 670

Thr Ala Thr Ala Ser Gly Thr Ala Ala Val Lys Glu Gly Glu Gly Thr
            675                 680                 685

Leu Thr Ala Pro Val Thr Val Thr Asn Asp Gly Leu Thr Asp Tyr Thr
        690                 695                 700

Asn Val Thr Val Thr Pro Thr Gly Leu Pro Ser Gly Trp Ser Ala Glu
705                 710                 715                 720

Ala Val Asn Val Gly Asn Leu Ala Ala Gly Gln Ser Ala Thr Val Asn
                    725                 730                 735

Val Pro Val Thr Val Pro Ala Ala Val Ser Gly Thr Val Ala Lys
                740                 745                 750

Ala Thr Met Lys Ile Thr Gly Lys Tyr Ala Gln Ser Glu Asp Thr Leu
            755                 760                 765

His Ser Phe Ala Glu Gly Glu Leu Ala Val Thr Val Thr Asp Pro Asp
        770                 775                 780

Pro Ala Ala Lys Arg Leu Lys Leu Thr Ile Glu Arg Thr Asp Asn
785                 790                 795                 800

Gly Asp Pro Val Lys Val Gly Asp Thr Leu Thr Tyr Arg Ile Thr Tyr
                    805                 810                 815

Glu Asn Val Gly Thr Gln Ser Phe Ala Val Tyr Pro Arg Glu Ser Asn
                820                 825                 830

Leu Asp Gly Val Thr Thr Pro Gln Ser Ala Ser Asn Pro Ala Pro Val
            835                 840                 845

Cys Arg Trp Ser Arg Leu Ala Pro Gly Ala Thr Gly Ala Cys Val Ser
850                 855                 860

Gly Asn Gly Lys Gln Leu Ala Tyr His Thr Val Thr Glu Ala Asp Ala
865                 870                 875                 880

Thr Ala Gly Ser Phe Thr Pro Ser Ala Thr Ile Asp Ala Thr Ala Asp
                    885                 890                 895

Ala Ser Gly Glu Thr Val Leu Glu Ser Val Ser Ile Thr Gly Asp Pro
                900                 905                 910

Val Thr Val Ser Gln Pro Val Glu Leu Pro Ala Asp Ile Ala Ala Trp
            915                 920                 925

Lys Thr Arg Asn Glu Ala Leu Ala Asp Trp Gln Thr Leu Ser Glu Lys
        930                 935                 940

Leu Ala Lys Thr Asp Arg Ile Asn Trp Leu Phe Thr Gly Asp Ser Ile
945                 950                 955                 960

-continued

```
Thr His Gly Val Gln Phe Thr Arg Gly Tyr Arg Thr Tyr Ser Glu Leu
            965                 970                 975
Phe Ala Asn His Leu Asp Thr Ala Ser Val Arg Gly Val Ser Arg Ala
            980                 985                 990
Asn Asp Val Val Met Asn Thr Gly Ile Ser Ser Ala Asp Ala Ser Trp
            995                 1000                1005
Pro Leu Lys Asp Gly Ala Phe Glu Lys Trp Val Ser Asp Lys His
        1010                1015                1020
Pro Asp Val Val Phe Leu Thr Phe Gly Met Asn Asp Gly Arg Thr
        1025                1030                1035
Gly Gln Ala Phe Thr Val Asp Gln Tyr Thr Ala Asn Leu Ser Thr
        1040                1045                1050
Leu Ile Asp Lys Ile Arg Asp Leu Gly Ala Ile Pro Val Leu Gln
        1055                1060                1065
Thr Gln Asn Tyr Thr Thr Asn Thr Thr Phe Asn Ala Asn Leu Asp
        1070                1075                1080
Thr Tyr Phe Asp Ala Glu Arg Arg Leu Ala Leu Asp Lys Asn Val
        1085                1090                1095
Leu Leu Val Asp Phe Asn Lys Gln Trp Leu Glu Leu Gly Gly Gly
        1100                1105                1110
Asn Arg Glu Ser Gly Thr Tyr Met Gly Ala Gly Asn Asp Ile His
        1115                1120                1125
Pro Gly Glu Asn Gly His Ile Glu Trp Ala Lys Phe Thr Leu Gly
        1130                1135                1140
Ala Leu Asn Met Ile Ala Asn Asp Asp Pro Leu Ala Arg Trp Ser
        1145                1150                1155
Ser Ser Asp Thr Thr Leu Asp Lys Pro Thr Val Thr Val Asp Ala
        1160                1165                1170
Asp Gly Asn Gly Leu Lys Gly Ser Asp Gly Leu Glu Pro Ala Pro
        1175                1180                1185
Ala Ala Ala Lys Ser Val Gly Lys Phe Leu Ser Gly Ala Gln Tyr
        1190                1195                1200
Val Asp Leu Gly Gly Asp Val Val Ser Ala Val Ala Gly Lys Arg
        1205                1210                1215
Glu Ser Asn Val Thr Ile Arg Phe Arg Ala Ser Ala Thr Gly Gln
        1220                1225                1230
Pro Gln Thr Leu Phe Ser Leu Gly Asp Ser Asp Ser Ala Thr Arg
        1235                1240                1245
Ala Thr Val Arg Leu Ser Ala Thr Gly Leu Val Gln Phe Leu Asn
        1250                1255                1260
Ser Gly Asn Thr Gly Asp Phe Tyr Thr Val Gly Thr Asn Asp Leu
        1265                1270                1275
Ala Asp Gly Ala Trp His Thr Val Ser Val Asn Phe Val Ala Asn
        1280                1285                1290
Gly Phe Thr Ile Tyr Val Asp Gly Ala Ala Met Arg Ala Ile Ser
        1295                1300                1305
Gly Gly Ala Gly Thr Gln Leu Asn Val Pro Gly Ala Ile Thr Val
        1310                1315                1320
Asn Thr Ala Thr Ala Gly Ala Ile Arg Gly Ala Asp Ser Ala Gly
        1325                1330                1335
Gly Ala Gln Gln Leu Thr Gly Ile Val Asp Tyr Val Ala Ala Trp
        1340                1345                1350
```

```
Ser Arg Thr Leu Thr Asp Ala Glu Ala Lys Arg Ile Ser Ala Glu
    1355                1360                1365

Thr Ser Ala Val Ala Val Thr Lys Val Asp Ala Ala Val Asn Ala
    1370                1375                1380

Leu Gln Pro Ile Ile Ser Asp Thr Gly Ala Arg Lys Asn Ile Val
    1385                1390                1395

Phe Val Gly Gly Glu Thr Ile Glu Gly Gly Tyr Thr Asp His Leu
    1400                1405                1410

Ile Ala Lys Asn Ile Val Gln Leu Leu Asp Glu Arg Val Arg Trp
    1415                1420                1425

Glu Tyr Val Thr Gly Leu Ser Ala Thr Asp Arg Glu Arg Gln Arg
    1430                1435                1440

Ala Lys Phe Phe Val Ala Ala Gly Gln Gly Gly Leu Thr Ala Lys
    1445                1450                1455

Gln Met Asp Glu Asp Tyr Ala Ala Met Val Gly Glu Tyr Ser Pro
    1460                1465                1470

Asp Ile Leu Phe Leu Ala Pro Asp Leu Tyr Asp Ala Asp Gly Asn
    1475                1480                1485

Leu Ala Glu Ser Ala Ala Ala Phe Ala Gly His Ile Arg Ser
    1490                1495                1500

Val Ala Ala Lys Ala Lys Glu Ala Gly Ala Lys Val Val Leu Val
    1505                1510                1515

Thr Pro Val Thr Val Arg Gly Gly Glu Asp Glu Tyr Ala Gly Ala
    1520                1525                1530

Met Arg Thr Val Ala Lys Glu Asp Asp Leu Pro Leu Ile Asp Ala
    1535                1540                1545

Gln Ala Trp Ile Gly Lys Val Val Ala Ala Asp Ala Ser Val Lys
    1550                1555                1560

Thr Ala Trp Phe Asn Lys Ala Gly Gln Leu Asn Tyr Ala Gly His
    1565                1570                1575

Leu Gly Tyr Ala Arg Phe Met Met Arg Ser Leu Asp Leu Tyr Pro
    1580                1585                1590

Ser Asn Val Ser Gly Ser Arg Ile Ala Ser Leu Pro Tyr Asp Thr
    1595                1600                1605

Ala Asn Val Thr Leu Val Gly Ala Ser Glu Asn Gly Gly Glu Leu
    1610                1615                1620

Pro Val Gly Arg Val Glu Gly Thr Asp Arg Ala His Ile Asp Thr
    1625                1630                1635

Met Gln Ile Gly Ala Ala Ala Ser Leu Val Val Asp Ser Tyr
    1640                1645                1650

Ala Val Tyr Glu Ile Gly Glu Asp Gly Gly Arg Thr Leu Val Ala
    1655                1660                1665

Asp Gly Leu Lys Pro Ala Asp Val Leu Ala Asp Gly Ile Asp Val
    1670                1675                1680

Thr Val Asn Asp Thr Ala Ala His Arg Tyr Glu Val Val Gly Ser
    1685                1690                1695

Ala Asn Val Pro Glu Gly Ala Asp Ala Val Thr Val Thr Tyr Thr
    1700                1705                1710

Ala Thr Leu Ala Ala Val Glu Glu Pro Glu Pro Gly Pro Asp Pro
    1715                1720                1725

Asp Pro Thr Pro Asp Pro Ser Glu Lys Pro Asp Gly Asp Gly Thr
    1730                1735                1740

Gly Asp Gly Thr Gly Ala Gly Thr Gly Asp Val Gln Lys Pro Thr
```

-continued

```
                1745                1750                1755

Pro Asp Ala Val Ala Lys Thr Gly Ala Asp Val Phe Gly Leu Leu
        1760                1765                1770

Thr Ala Val Ala Ala Leu Leu Ala Ala Gly Gly Val Thr Leu Ser
    1775                1780                1785

Leu Arg Arg Arg Ala Asn Arg
        1790                1795

<210> SEQ ID NO 13
<211> LENGTH: 824
<212> TYPE: PRT
<213> ORGANISM: Bifidobacterium longum
<220> FEATURE:
<223> OTHER INFORMATION: Glycosyl hydrolase, BNR repeat-containing
      protein [Bifidobacterium longum subsp. infantis ATCC
      15697=JCM 1222]
<300> PUBLICATION INFORMATION:
<308> DATABASE ACCESSION NUMBER: gi 213523006
<300> PUBLICATION INFORMATION:
<308> DATABASE ACCESSION NUMBER: ACJ51753.1

<400> SEQUENCE: 13

Met Ala Ala Ser Asn Pro Ile Ser Trp Ser Gln Arg Thr Phe Pro Ser
1               5                   10                  15

Pro Glu Gly Thr Ile Ala Cys Arg Phe Arg Ala His Ala Asp Gly Arg
            20                  25                  30

Ile Phe Asp Ala Val Asn Gly Ser Ala Asn Asp Ala Pro Leu Leu Ile
        35                  40                  45

Cys Ala Ile Glu His Asp Ala Leu Arg Val Arg Ala Thr Thr Pro Arg
    50                  55                  60

Gln His Val Asp Phe Asp Ile Glu Asp Thr Thr Gly Ile Ala Asp Gly
65                  70                  75                  80

Ala Met His Thr Phe Ala Leu Thr Phe Gly Glu Phe Gly Thr Arg Val
                85                  90                  95

Tyr Leu Asp Gly Ser Gln Cys Phe Ser Gly Thr Ala Asn Leu Cys Pro
            100                 105                 110

Thr Thr Leu Thr Gly Thr Glu Gly Ser Gly Gln Gly Ala Ile Arg Leu
        115                 120                 125

Ala Gly Pro Ser Ile Asp Val Thr Asp Met Arg Leu His Ala Ile Pro
    130                 135                 140

Leu Thr Ser Glu Ser Ile Ala Ala Leu Thr Pro Arg Pro Ala Pro Asp
145                 150                 155                 160

Ile Asp Phe Ala Ala Ala Gln Leu Ala Pro Arg Asp Val Arg Arg Val
                165                 170                 175

Arg Thr Leu Arg Ser Gly Thr Ile Phe Met His Phe Arg Val Arg Gly
            180                 185                 190

Pro Arg Gln Tyr Gly Thr Leu Leu Ala Ala Gly Glu Arg Gly Glu Glu
        195                 200                 205

Arg Leu Ala Val Ser Ile Asp Asp Asn Gly Ile Thr Met Thr Ala Ala
    210                 215                 220

Asp Gly Leu Tyr Glu Pro Ser Thr Tyr His Ala Arg Gly Ala Trp Asp
225                 230                 235                 240

Asp Gly Arg Trp His Asp Leu Ser Ile Arg Ser Ala Arg Gly Ala Ile
                245                 250                 255

Asp Met Tyr Val Asp Gly Trp His Glu Leu His Gln Ala Gly Gln Val
            260                 265                 270

Phe Phe Gly Asp Trp Pro Gln Leu Asp Glu Val Ala Ile Gly Gln Asn
```

```
                    275                 280                 285
Thr Glu Gly Val Arg Leu Met Gly Glu Val Arg Asn Gly Val Phe
        290                 295                 300
Thr Thr Pro Leu Thr Asp Gly Ala Ile Arg Arg Leu Ser Asp Ala Pro
305                 310                 315                 320
Ala Leu Thr Thr Thr Ala Leu Phe Asp Lys Gly Tyr His Gly Ser Val
                        325                 330                 335
Ser Tyr Arg Ile Pro Ser Ile Ile Arg Thr Pro His Gly Val Val
            340                 345                 350
Ala Gly Ala Asp Gln Arg Thr Ala Ile Ala Asn Asp Ala Pro Asn His
                355                 360                 365
Ile Asn Phe Val Met Arg Arg Ser Leu Asp Gly Arg Thr Trp Leu
    370                 375                 380
Asp Met Gln Thr Val Ile Ala Asn Pro Gly Glu Gly Val Asp Gly Ala
385                 390                 395                 400
Cys Thr Ile Asp Ser Cys Leu Val Cys Asp Glu Arg Asn Gly Arg Leu
                        405                 410                 415
Thr Val Leu Ile Asp Arg Phe Ala Gly Val Gly Leu Pro Asn Asn
            420                 425                 430
Thr Pro Gly Thr Gly Val Asp Arg His Gly Arg Pro Cys Leu Tyr Asp
                435                 440                 445
Arg Ala Gly Thr Arg Tyr Val Leu Ala Asp Gly Thr Val Leu Asp
    450                 455                 460
Gly Gly Gly Glu Arg Thr Gly Tyr Arg Val Asp Ala His Gly Asn Val
465                 470                 475                 480
Thr His Glu Gly Arg Ala Ser Gly Asn Ile Tyr Leu Lys Glu Gly Ala
                        485                 490                 495
Asp Pro Asp Glu Ser Leu Leu Ile Glu Arg Thr Ser Phe Ile Ile Glu
            500                 505                 510
Leu His Ser Asp Asp Asp Gly Glu Thr Trp Ser Thr Pro Arg Asn Ile
                515                 520                 525
Asn His Met Ile Lys Glu Asp Trp Met His Phe Leu Gly Val Ser Pro
    530                 535                 540
Gly Asn Gly Ile Gln Leu Gln Ala Ser Glu His Arg Gly Arg Leu Leu
545                 550                 555                 560
Val Pro Phe Tyr Cys Thr Gly Ala Ser Leu Lys His Tyr Ser Gly Gly
                        565                 570                 575
Ala Leu Ile Ser Asp Asp Gly Asp Thr Trp Arg Arg Gly Ser Met
            580                 585                 590
Ile Asn Asp Gly Arg Ile Val Asn Gly Thr Ala Val Asp Pro Lys Asn
                595                 600                 605
Ile Arg Asp Asp Asp Ala Thr Thr His Glu Ser Val Phe Val Glu Arg
    610                 615                 620
Ala Asp Gly Thr Val Val Cys Phe Phe Arg Asn Gln Asn His Ala Gly
625                 630                 635                 640
Arg Ile Gly Val Ala Leu Ser His Asp Gly Glu Thr Trp Asp Asp
                        645                 650                 655
Leu Tyr Phe Asp Lys Asp Val Pro Asp Ile Phe Cys Gln Pro Asn Ala
            660                 665                 670
Val Ala Cys Ala Pro Arg Ser Asp Thr Met Val Phe Ala Asn Ala Ser
                675                 680                 685
Gln Met Leu Pro Tyr Arg Gly Asn Gly Val Leu Arg Leu Ser Leu Asp
    690                 695                 700
```

```
Gly Ala Arg Thr Trp Ala Ala His Arg Cys Ile Asn Pro Tyr His Tyr
705                 710                 715                 720

Gly Tyr Gln Cys Met Thr Met Leu Pro Asp Gly Glu Leu Gly Leu Leu
            725                 730                 735

Trp Glu Arg Glu Thr Ala Gly Leu Tyr Phe Thr Thr Leu Pro Leu Ser
        740                 745                 750

Val Phe Gly Ala Ala Glu Thr His Ser Ala Asp Pro Glu Pro Lys Pro
    755                 760                 765

Glu Pro Lys Pro Glu Pro Lys Pro Ala Gly Pro Lys Val Asp Val
770                 775                 780

Pro Thr Glu Lys Pro Gly Leu Ser Lys Thr Gly Ala Ser Thr Ala Gly
785                 790                 795                 800

Met Ser Ile Val Phe Val Leu Leu Ala Leu Ser Gly Val Ala Ala Leu
                805                 810                 815

Ser Leu Arg Arg Arg Ser Val His
            820
```

<210> SEQ ID NO 14
<211> LENGTH: 393
<212> TYPE: PRT
<213> ORGANISM: Bifidobacterium longum
<220> FEATURE:
<223> OTHER INFORMATION: Exo-alpha-sialidase [Bifidobacterium longum
      subsp. infantis ATCC 15697=JCM 1222]
<300> PUBLICATION INFORMATION:
<308> DATABASE ACCESSION NUMBER: gi 213524659
<300> PUBLICATION INFORMATION:
<308> DATABASE ACCESSION NUMBER: ACJ53406.1

<400> SEQUENCE: 14

```
Met Thr Glu Asn Gly Met Met Asn Thr Asn Asn Thr Val Cys Gly Ala
1               5                   10                  15

Asn His Asp Gly Ala Met Ser Leu Ala Ala Pro Gly Asp Tyr Gly Val
            20                  25                  30

Ala Cys Tyr Arg Ile Pro Ala Leu Ala Glu Ala Pro Asn Gly Trp Ile
        35                  40                  45

Leu Ala Ala Phe Asp Ala Arg Pro His Asn Cys Gln Asp Ala Pro Gln
    50                  55                  60

Ala Asn Ser Ile Val Gln Arg Ile Ser Lys Asp Gly Gly Arg Ser Phe
65                  70                  75                  80

Glu Pro Gln His Val Ala Ala Gly His Asp Gly Val Asp Lys Tyr
            85                  90                  95

Gly Tyr Ser Asp Pro Ser Tyr Val Val Asp Arg Gln Thr Gly Glu Val
            100                 105                 110

Phe Leu Phe Phe Val Lys Ser Tyr Asp Ala Gly Phe Gly Thr Ser Gln
        115                 120                 125

Ala Gly Val Asp Pro Ser Ala Arg Glu Val Leu Gln Ala Val Thr
    130                 135                 140

Ser Ser Ile Asp Asn Gly Val Thr Trp Ser Glu Pro Arg Ile Ile Thr
145                 150                 155                 160

Ala Asp Ile Thr Asn Ser Glu Ser Trp Ile Ser Arg Phe Ala Ser Ser
                165                 170                 175

Gly Ala Gly Ile Gln Leu Thr Tyr Gly Glu His Ala Gly Arg Leu Ile
            180                 185                 190

Gln Gln Tyr Thr Ile Lys Glu Leu Asp Gly Arg Tyr Arg Ala Val Ser
        195                 200                 205
```

```
Val Phe Ser Asp Asp His Gly Ala Thr Trp His Ala Gly Thr Pro Val
        210                 215                 220
Gly Asp His Met Asp Glu Asn Lys Val Val Glu Leu Ser Asp Gly Arg
225                 230                 235                 240
Val Met Leu Asn Ser Arg Ser Ser Asp Gly Asn Gly Cys Arg Tyr Val
                245                 250                 255
Ala Ile Ser Arg Asp Gly Ala Thr Tyr Gly Pro Val Ile Arg Glu
            260                 265                 270
Thr Gln Leu Pro Asp Pro Glu Asn Ala Gln Ile Ala Arg Ala Phe
        275                 280                 285
Pro Asp Ala Pro Glu Gly Ser Ala Gln Ala Lys Val Leu Leu Tyr Ser
290                 295                 300
Ser Ser Ser Pro Ser Asp Arg Ile Asp Gly Leu Val Arg Val Ser Ile
305                 310                 315                 320
Asp Asp Gly Lys Thr Trp Ser Ala Gly Arg Arg Phe Thr Thr Gly Pro
                325                 330                 335
Met Ala Tyr Ser Val Ile Ala Ala Leu Ser His Lys Ala Gly Gly Gly
                340                 345                 350
Tyr Gly Leu Leu Tyr Glu Gly Asp Asn Asn Asn Ile Met Tyr Thr Arg
            355                 360                 365
Ile Ser Leu Asp Trp Leu Asn Gly Gln Leu Asn Val Asp Gly Ile Gly
370                 375                 380
Gly Phe Pro Leu Ser Gly Glu Gly Gly
385                 390

<210> SEQ ID NO 15
<211> LENGTH: 642
<212> TYPE: PRT
<213> ORGANISM: Trypanosoma cruzi
<220> FEATURE:
<223> OTHER INFORMATION: Trans-sialidase [Trypanosoma cruzi]
<300> PUBLICATION INFORMATION:
<308> DATABASE ACCESSION NUMBER: gi 432485
<300> PUBLICATION INFORMATION:
<308> DATABASE ACCESSION NUMBER: AAA66352.1

<400> SEQUENCE: 15

Met Leu Ala Pro Gly Ser Ser Arg Val Glu Leu Phe Lys Arg Gln Ser
1               5                   10                  15
Ser Lys Val Pro Phe Glu Lys Asp Gly Lys Val Thr Glu Arg Val Val
                20                  25                  30
His Ser Phe Arg Leu Pro Ala Leu Val Asn Val Asp Gly Val Met Val
            35                  40                  45
Ala Ile Ala Asp Ala Arg Tyr Glu Thr Ser Asn Asp Asn Ser Leu Ile
50                  55                  60
Asp Thr Val Ala Lys Tyr Ser Val Asp Asp Gly Glu Thr Trp Glu Thr
65                  70                  75                  80
Gln Ile Ala Ile Lys Asn Ser Arg Ala Ser Ser Val Ser Arg Val Val
                85                  90                  95
Asp Pro Thr Val Ile Val Lys Gly Asn Lys Leu Tyr Val Leu Val Gly
                100                 105                 110
Ser Tyr Asn Ser Ser Arg Ser Tyr Trp Thr Ser His Gly Asp Ala Arg
            115                 120                 125
Asp Trp Asp Ile Leu Leu Ala Val Gly Glu Val Thr Lys Ser Thr Ala
        130                 135                 140
Gly Gly Lys Ile Thr Ala Ser Ile Lys Trp Gly Ser Pro Val Ser Leu
145                 150                 155                 160
```

-continued

Lys Glu Phe Phe Pro Ala Glu Met Glu Gly Met His Thr Asn Gln Phe
                165                 170                 175
Leu Gly Gly Ala Gly Val Ala Ile Val Ala Ser Asn Gly Asn Leu Val
            180                 185                 190
Tyr Pro Val Gln Val Thr Asn Lys Lys Gln Val Phe Ser Lys Ile
        195                 200                 205
Phe Tyr Ser Glu Asp Glu Gly Lys Thr Trp Lys Phe Gly Lys Gly Arg
    210                 215                 220
Ser Ala Phe Gly Cys Ser Glu Pro Val Ala Leu Glu Trp Glu Gly Lys
225                 230                 235                 240
Leu Ile Ile Asn Thr Arg Val Asp Tyr Arg Arg Leu Val Tyr Glu
                245                 250                 255
Ser Ser Asp Met Gly Asn Ser Trp Leu Glu Ala Val Gly Thr Leu Ser
            260                 265                 270
Arg Val Trp Gly Pro Ser Pro Lys Ser Asn Gln Pro Gly Ser Gln Ser
        275                 280                 285
Ser Phe Thr Ala Val Thr Ile Glu Gly Met Arg Val Met Leu Phe Thr
    290                 295                 300
His Pro Leu Asn Phe Lys Gly Arg Trp Leu Arg Asp Arg Leu Asn Leu
305                 310                 315                 320
Trp Leu Thr Asp Asn Gln Arg Ile Tyr Asn Val Gly Gln Val Ser Ile
                325                 330                 335
Gly Asp Glu Asn Ser Ala Tyr Ser Ser Val Leu Tyr Lys Asp Asp Lys
            340                 345                 350
Leu Tyr Cys Leu His Glu Ile Asn Ser Asn Glu Val Tyr Ser Leu Val
        355                 360                 365
Phe Ala Arg Leu Val Gly Glu Leu Arg Ile Ile Lys Ser Val Leu Gln
    370                 375                 380
Ser Trp Lys Asn Trp Asp Ser His Leu Ser Ser Ile Cys Thr Pro Ala
385                 390                 395                 400
Asp Pro Ala Ala Ser Ser Glu Arg Gly Cys Gly Pro Ala Val Thr
                405                 410                 415
Thr Val Gly Leu Val Gly Phe Leu Ser His Ser Ala Thr Lys Thr Glu
            420                 425                 430
Trp Glu Asp Ala Tyr Arg Cys Val Asn Ala Ser Thr Ala Asn Ala Glu
        435                 440                 445
Arg Val Pro Asn Gly Leu Lys Phe Ala Gly Val Gly Gly Ala Leu
    450                 455                 460
Trp Pro Val Ser Gln Gln Gly Gln Asn Gln Arg Tyr Arg Phe Ala Asn
465                 470                 475                 480
His Ala Phe Thr Val Val Ala Ser Val Thr Ile His Glu Val Pro Ser
                485                 490                 495
Val Ala Ser Pro Leu Leu Gly Ala Ser Leu Asp Ser Ser Gly Gly Lys
            500                 505                 510
Lys Leu Leu Gly Leu Ser Tyr Asp Glu Arg His Gln Trp Gln Pro Ile
        515                 520                 525
Tyr Gly Ser Thr Pro Val Thr Pro Thr Gly Ser Trp Glu Met Gly Lys
    530                 535                 540
Arg Tyr His Val Val Leu Thr Met Ala Asn Lys Ile Gly Ser Glu Tyr
545                 550                 555                 560
Ile Asp Gly Glu Pro Leu Glu Gly Ser Gly Gln Thr Val Val Pro Asp
                565                 570                 575

```
Glu Arg Thr Pro Asp Ile Ser His Phe Tyr Val Gly Gly Tyr Lys Arg
            580                 585                 590

Ser Asp Met Pro Thr Ile Ser His Val Thr Val Asn Asn Val Leu Leu
        595                 600                 605

Tyr Asn Arg Gln Leu Asn Ala Glu Glu Ile Arg Thr Leu Phe Leu Ser
    610                 615                 620

Gln Asp Leu Ile Gly Thr Glu Ala His Met Asp Ser Ser Asp Thr
625                 630                 635                 640

Ser Ala

<210> SEQ ID NO 16
<211> LENGTH: 964
<212> TYPE: PRT
<213> ORGANISM: Trypanosoma cruzi
<220> FEATURE:
<223> OTHER INFORMATION: Trans-sialidase enzyme of T. Cruzi
<300> PUBLICATION INFORMATION:
<308> DATABASE ACCESSION NUMBER: Q26963-1

<400> SEQUENCE: 16

Met Gly Lys Thr Val Val Gly Ala Ser Arg Met Phe Trp Leu Met Phe
1               5                   10                  15

Phe Val Pro Leu Leu Ala Leu Cys Pro Ser Glu Pro Ala His Ala
            20                  25                  30

Leu Ala Pro Gly Ser Ser Arg Val Glu Leu Phe Lys Arg Gln Ser Ser
            35                  40                  45

Lys Val Pro Phe Glu Lys Gly Gly Lys Val Thr Glu Arg Val Val His
    50                  55                  60

Ser Phe Arg Leu Pro Ala Leu Val Asn Val Asp Gly Val Met Val Ala
65                  70                  75                  80

Ile Ala Asp Ala Arg Tyr Glu Thr Ser Asn Asp Asn Ser Leu Ile Asp
                85                  90                  95

Thr Val Ala Lys Tyr Ser Val Asp Asp Gly Glu Thr Trp Glu Thr Gln
            100                 105                 110

Ile Ala Ile Lys Asn Ser Arg Ala Ser Ser Val Ser Arg Val Val Asp
            115                 120                 125

Pro Thr Val Ile Val Lys Gly Asn Lys Leu Tyr Val Leu Val Gly Ser
    130                 135                 140

Tyr Asn Ser Ser Arg Ser Tyr Trp Thr Ser His Gly Asp Ala Arg Asp
145                 150                 155                 160

Trp Asp Ile Leu Leu Ala Val Gly Glu Val Thr Lys Ser Thr Ala Gly
                165                 170                 175

Gly Lys Ile Thr Ala Ser Ile Lys Trp Gly Ser Pro Val Ser Leu Lys
            180                 185                 190

Glu Phe Phe Pro Ala Glu Met Glu Gly Met His Thr Asn Gln Phe Leu
            195                 200                 205

Gly Gly Ala Gly Val Ala Ile Val Ala Ser Asn Gly Asn Leu Val Tyr
    210                 215                 220

Pro Val Gln Val Thr Asn Lys Lys Lys Gln Val Phe Ser Lys Ile Phe
225                 230                 235                 240

Tyr Ser Glu Asp Asp Gly Lys Thr Trp Lys Phe Gly Glu Gly Arg Ser
                245                 250                 255

Ala Phe Gly Cys Ser Glu Ala Val Ala Leu Glu Trp Glu Gly Lys Leu
            260                 265                 270

Ile Ile Asn Thr Arg Val Asp Tyr Arg Arg Arg Leu Val Tyr Glu Ser
            275                 280                 285
```

-continued

```
Ser Asp Met Gly Asn Thr Trp Leu Glu Ala Val Gly Thr Leu Ser Arg
    290                 295                 300

Val Trp Gly Pro Ser Pro Lys Ser Asn Gln Pro Gly Ser Gln Ser Ser
305                 310                 315                 320

Phe Thr Ala Val Thr Ile Glu Gly Met Arg Val Met Leu Phe Thr His
                325                 330                 335

Pro Leu Asn Phe Lys Gly Arg Trp Leu Arg Asp Arg Leu Asn Leu Trp
                340                 345                 350

Leu Thr Asp Asn Gln Arg Ile Tyr Asn Val Gly Gln Val Ser Ile Gly
            355                 360                 365

Asp Glu Asn Ser Ala His Ser Ser Val Leu Tyr Lys Asp Asp Lys Leu
    370                 375                 380

Tyr Cys Leu His Glu Ile Asn Ser Asn Glu Val Tyr Ser Leu Val Phe
385                 390                 395                 400

Ala Arg Leu Val Gly Glu Leu Arg Ile Ile Lys Ser Val Leu Gln Ser
                405                 410                 415

Trp Lys Asn Trp Asp Ser His Leu Ser Ser Ile Cys Thr Pro Ala Asp
                420                 425                 430

Pro Ala Ala Ser Ser Glu Arg Gly Cys Gly Pro Ala Val Thr Thr
            435                 440                 445

Val Gly Leu Val Gly Phe Leu Ser His Ser Ala Thr Lys Thr Glu Trp
    450                 455                 460

Glu Asp Ala Tyr Arg Cys Val Asn Ala Ser Thr Ala Asn Ala Glu Arg
465                 470                 475                 480

Val Pro Asn Gly Leu Lys Phe Ala Gly Val Gly Gly Ala Leu Trp
                485                 490                 495

Pro Val Ser Gln Gln Gly Gln Asn Gln Arg Tyr His Phe Ala Asn His
            500                 505                 510

Ala Phe Thr Leu Val Ala Ser Val Thr Ile His Glu Val Pro Ser Val
    515                 520                 525

Ala Ser Pro Leu Leu Gly Ala Ser Leu Asp Ser Ser Gly Gly Lys Lys
    530                 535                 540

Leu Leu Gly Leu Ser Tyr Asp Glu Lys His Gln Trp Gln Pro Ile Tyr
545                 550                 555                 560

Gly Ser Thr Pro Val Thr Pro Thr Gly Ser Trp Glu Thr Gly Lys Arg
                565                 570                 575

Tyr His Val Val Leu Thr Met Ala Asn Lys Ile Gly Ser Val Tyr Ile
            580                 585                 590

Asp Gly Glu Pro Leu Glu Gly Ser Gly Gln Thr Val Val Pro Asp Gly
    595                 600                 605

Arg Thr Pro Asp Ile Ser His Phe Tyr Val Gly Gly Tyr Arg Arg Ser
    610                 615                 620

Asp Met Pro Thr Ile Ser His Val Thr Val Asn Asn Val Leu Leu Tyr
625                 630                 635                 640

Asn Arg Gln Leu Asn Ala Glu Glu Ile Arg Thr Leu Phe Leu Ser Gln
                645                 650                 655

Asp Leu Ile Gly Thr Glu Ala His Met Asp Ser Ser Ser Asp Ser Asn
            660                 665                 670

Ala His Ser Thr Pro Ser Thr Pro Gly Asp Ser Ser Ala His Ser Thr
    675                 680                 685

Pro Ser Thr Pro Ala Asp Asn Gly Ala His Ser Thr Pro Ser Thr Pro
    690                 695                 700
```

```
Ala Asp Asn Gly Ala His Ser Thr Pro Ser Thr Pro Gly Asp Asn Gly
705                 710                 715                 720

Ala His Ser Thr Pro Leu Thr Pro Ala Asp Asn Gly Ala His Ser Thr
            725                 730                 735

Pro Pro Thr Pro Ala Asp Ser Ser Ala His Ser Thr Pro Ser Thr Pro
        740                 745                 750

Ala Asp Asn Gly Ala His Ser Thr Pro Ser Thr Pro Ala Asp Asn Gly
                755                 760                 765

Ala His Ser Thr Pro Leu Thr Pro Ala Asp Asn Gly Ala His Ser Thr
            770                 775                 780

Pro Pro Thr Pro Ala Asp Ser Ser Ala His Ser Thr Pro Ser Thr Pro
785                 790                 795                 800

Ala Asp Asn Gly Ala His Ser Thr Pro Ser Thr Pro Ala Asp Asn Gly
                805                 810                 815

Ala His Ser Thr Pro Pro Thr Pro Ala Asp Ser Ser Ala His Ser Thr
            820                 825                 830

Pro Ser Thr Pro Gly Asp Asn Gly Ala His Ser Thr Pro Leu Thr Pro
        835                 840                 845

Ala Asp Asn Gly Ala His Ser Thr Pro Leu Thr Pro Ala Asp Ser Ser
                850                 855                 860

Ala His Ser Thr Pro Ser Thr Pro Gly Asp Asn Gly Ala His Ser Thr
865                 870                 875                 880

Pro Ser Ala Pro Ala Asp Asn Gly Ala His Ser Thr Pro Pro Thr Pro
                885                 890                 895

Ala Ser Asn Gly Ala His Ser Thr Pro Ser Ala Pro Gly Asp Asn Gly
            900                 905                 910

Ala His Ser Thr Pro Ser Thr Pro Ala Asp Asn Asp Ala Asn Gly Met
            915                 920                 925

Val Leu Phe Phe Pro Asp Gly Ala Ala Phe Ser Ala Phe Ser Gly Gly
            930                 935                 940

Gly Leu Leu Ser Cys Ala Ser Ala Leu Leu Leu His Val Phe Val Met
945                 950                 955                 960

Ala Val Leu Phe

<210> SEQ ID NO 17
<211> LENGTH: 1112
<212> TYPE: PRT
<213> ORGANISM: Bifidobacterium bifidum
<220> FEATURE:
<223> OTHER INFORMATION: Lacto-N-biosidase [Bifidobacterium bifidum
      JCM1254]
<300> PUBLICATION INFORMATION:
<308> DATABASE ACCESSION NUMBER: gi 167369738
<300> PUBLICATION INFORMATION:
<308> DATABASE ACCESSION NUMBER: ABZ78855.1

<400> SEQUENCE: 17

Met Glu Lys Ser Ser Asn Arg Arg Phe Gly Val Arg Thr Val Ala Ala
1               5                   10                  15

Ile Val Ala Gly Leu Met Val Gly Gly Met Cys Thr Ala Met Thr Ala
            20                  25                  30

Ser Ala Ala Asp Asp Ser Ala Ala Gly Tyr Ser Ala Thr Ala Pro Val
        35                  40                  45

Asn Leu Thr Arg Pro Ala Thr Val Pro Ser Met Asp Gly Trp Thr Asp
    50                  55                  60

Gly Thr Gly Ala Trp Thr Leu Gly Glu Gly Thr Arg Val Val Ser Ser
65              70                  75                  80
```

```
Asp Ala Leu Ala Ala Arg Ala Gln Ser Leu Ala Ser Glu Leu Thr Lys
            85                  90                  95

Phe Thr Asp Val Asp Ile Lys Ala Ala Thr Gly Ser Ala Thr Gly Lys
            100                 105                 110

Asp Ile Ser Leu Thr Leu Asp Ala Ser Lys Lys Ala Glu Leu Gly Asp
            115                 120                 125

Glu Gly Phe Lys Leu Asn Ile Gly Ser Lys Gly Leu Glu Val Ile Gly
            130                 135                 140

Ala Thr Asp Ile Gly Val Phe Tyr Gly Thr Arg Ser Val Ser Gln Met
145                 150                 155                 160

Leu Arg Gln Gly Gln Leu Thr Leu Pro Ala Gly Thr Val Ala Thr Lys
            165                 170                 175

Pro Lys Tyr Lys Glu Arg Gly Ala Thr Leu Cys Ala Cys Gln Ile Asn
            180                 185                 190

Ile Ser Thr Asp Trp Ile Asp Arg Phe Leu Ser Asp Met Ala Asp Leu
            195                 200                 205

Arg Leu Asn Tyr Val Leu Leu Glu Met Lys Leu Lys Pro Glu Glu Asp
            210                 215                 220

Asn Thr Lys Lys Ala Ala Thr Trp Ser Tyr Tyr Thr Arg Asp Asp Val
225                 230                 235                 240

Lys Lys Phe Val Lys Lys Ala Asn Asn Tyr Gly Ile Asp Val Ile Pro
            245                 250                 255

Glu Ile Asn Ser Pro Gly His Met Asn Val Trp Leu Glu Asn Tyr Pro
            260                 265                 270

Glu Tyr Gln Leu Ala Asp Asn Ser Gly Arg Lys Asp Pro Asn Lys Leu
            275                 280                 285

Asp Ile Ser Asn Pro Glu Ala Val Lys Phe Tyr Lys Thr Leu Ile Asp
            290                 295                 300

Glu Tyr Asp Gly Val Phe Thr Thr Lys Tyr Trp His Met Gly Ala Asp
305                 310                 315                 320

Glu Tyr Met Ile Gly Thr Ser Phe Asp Asn Tyr Ser Lys Leu Lys Thr
            325                 330                 335

Phe Ala Glu Lys Gln Tyr Gly Ala Gly Ala Thr Pro Asn Asp Ala Phe
            340                 345                 350

Thr Gly Phe Ile Asn Asp Ile Asp Lys Tyr Val Lys Ala Lys Gly Lys
            355                 360                 365

Gln Leu Arg Ile Trp Asn Asp Gly Ile Val Asn Thr Lys Asn Val Ser
370                 375                 380

Leu Asn Lys Asp Ile Val Ile Glu Tyr Trp Tyr Gly Ala Gly Arg Lys
385                 390                 395                 400

Pro Gln Glu Leu Val Gln Asp Gly Tyr Thr Leu Met Asn Ala Thr Gln
            405                 410                 415

Ala Leu Tyr Trp Ser Arg Ser Ala Gln Val Tyr Lys Val Asn Ala Ala
            420                 425                 430

Arg Leu Tyr Asn Asn Asn Trp Asn Val Gly Thr Phe Asp Gly Gly Arg
            435                 440                 445

Gln Ile Asp Lys Asn Tyr Asp Lys Leu Thr Gly Ala Lys Val Ser Ile
            450                 455                 460

Trp Pro Asp Ser Ser Tyr Phe Gln Thr Glu Asn Glu Val Glu Lys Glu
465                 470                 475                 480

Ile Phe Asp Gly Met Arg Phe Ile Ser Gln Met Thr Trp Ser Asp Ser
            485                 490                 495
```

```
Arg Pro Trp Ala Thr Trp Asn Asp Met Lys Ala Asp Ile Asp Lys Ile
            500                 505                 510

Gly Tyr Pro Leu Asp Ile Arg Glu Tyr Asp Tyr Thr Pro Val Asp Ala
        515                 520                 525

Gly Ile Tyr Asp Ile Pro Gln Leu Lys Ser Ile Ser Lys Gly Pro Trp
    530                 535                 540

Glu Leu Ile Thr Thr Pro Asp Gly Tyr Tyr Gln Met Lys Asp Thr Val
545                 550                 555                 560

Ser Gly Lys Cys Leu Ala Leu Phe Thr Gly Ser Lys His Leu Asp Val
                565                 570                 575

Val Thr Gln Val Gly Ala Arg Pro Glu Leu Arg Asn Cys Ala Asp Val
            580                 585                 590

Ser Val Gly Gln Asp Gln Arg Asn Thr Ala Asn Glu Arg Asn Thr Gln
        595                 600                 605

Lys Trp Gln Ile Arg Ala Asp Lys Asp Gly Lys Tyr Thr Ile Ser Pro
    610                 615                 620

Ala Leu Thr Gln Gln Arg Leu Ala Ile Ala Thr Gly Asn Glu Gln Asn
625                 630                 635                 640

Ile Asp Leu Glu Thr His Arg Pro Ala Ala Gly Thr Val Ala Gln Phe
                645                 650                 655

Pro Ala Asp Leu Val Ser Asp Asn Ala Leu Phe Thr Leu Thr Gly His
            660                 665                 670

Met Gly Met Ser Ala Thr Val Asp Ser Lys Thr Val Asn Pro Ala Ser
        675                 680                 685

Pro Ser Lys Ile Thr Val Lys Val Arg Ala Ala Ser Asn Ala Asn Thr
    690                 695                 700

Gly Asp Val Thr Val Thr Pro Val Val Pro Glu Gly Trp Glu Ile Lys
705                 710                 715                 720

Pro Gly Ser Val Ser Leu Lys Ser Ile Pro Ala Gly Lys Ala Ala Ile
                725                 730                 735

Ala Tyr Phe Asn Val Val Asn Thr Thr Gly Thr Gly Asp Ala Thr Val
            740                 745                 750

Gln Phe Lys Leu Thr Asn Thr Lys Thr Gly Glu Glu Leu Gly Thr Thr
        755                 760                 765

Ser Val Ala Leu Thr Gly Ser Leu Thr Lys Asp Val Glu Ala Ser Asp
    770                 775                 780

Tyr Ala Ala Ser Ser Gln Glu Thr Thr Gly Glu His Ala Pro Val Gly
785                 790                 795                 800

Asn Ala Phe Asp Lys Asn Ala Asn Thr Phe Trp His Ser Lys Tyr Ser
                805                 810                 815

Asn Pro Ser Ala Asn Leu Pro His Trp Leu Ala Phe Lys Ala Ser Pro
            820                 825                 830

Gly Glu Gly Asn Lys Ile Ala Ala Ile Thr His Leu Tyr Arg Gln Asp
        835                 840                 845

Lys Leu Asn Gly Pro Ala Lys Asn Val Ala Val Tyr Val Ala Ala
    850                 855                 860

Ser Asp Ala Asn Ser Val Ala Asp Val Thr Asn Trp Gly Glu Pro Val
865                 870                 875                 880

Ala Thr Ala Glu Phe Pro Tyr Thr Lys Glu Leu Gln Thr Ile Ala Leu
                885                 890                 895

Pro Asn Thr Ile Pro Ser Gly Asp Val Tyr Val Lys Phe Gln Ile Asn
            900                 905                 910

Asp Ala Trp Gly Leu Thr Glu Thr Ser Ala Gly Val Thr Trp Ala Ala
```

```
                915                 920                 925
Val Ala Glu Leu Ala Ala Thr Ala Lys Ala Thr Pro Val Glu Leu Thr
            930                 935                 940
Glu Pro Glu Gln Pro Lys Asp Asn Pro Glu Val Thr Glu Thr Pro Glu
945                 950                 955                 960
Ala Thr Gly Val Thr Val Ser Gly Asp Gly Val Ala Asn Gly Ala Leu
                965                 970                 975
Ser Leu Lys Lys Gly Thr Thr Ala Gln Leu Thr Ala Lys Val Ala Pro
            980                 985                 990
Asp Asp Ala Asp Gln Ala Val Thr Trp Ala Ser Ser Asp Asp Lys Val
            995                1000                1005
Val Thr Val Asp Lys Thr Gly Lys Val Thr Ala Val Ala Lys Gly
            1010                1015                1020
Val Ala Lys Val Thr Ala Thr Thr Ala Asn Gly Lys Ser Ala Ser
            1025                1030                1035
Val Thr Val Thr Val Thr Glu Asp Ser Glu Val Pro Gly Pro Thr
            1040                1045                1050
Gly Pro Thr Glu Pro Thr Lys Pro Gly Thr Glu Lys Pro Thr Thr
            1055                1060                1065
Lys Pro Thr Thr Lys Pro Asn Asp Gly Lys Leu Ser Ala Thr Gly
            1070                1075                1080
Ala Asp Thr Ala Val Leu Ala Thr Ile Ala Ala Leu Phe Ala Leu
            1085                1090                1095
Ala Gly Gly Ala Val Val Ala Val Arg Arg Ser Val Arg
            1100                1105                1110

<210> SEQ ID NO 18
<211> LENGTH: 639
<212> TYPE: PRT
<213> ORGANISM: Streptomyces sp.
<220> FEATURE:
<223> OTHER INFORMATION: Lacto-N-biosidase precursor [Streptomyces sp.]
<300> PUBLICATION INFORMATION:
<308> DATABASE ACCESSION NUMBER: gi 4096812
<300> PUBLICATION INFORMATION:
<308> DATABASE ACCESSION NUMBER: AAD10478.1

<400> SEQUENCE: 18

Met Asp Met Arg Met Ala Arg Arg Thr Ile Gly Ala Val Val Thr
1               5                  10                  15

Ala Leu Ala Ala Ala Leu Leu Pro Trp Gln Ser Ala Thr Ala Glu Gly
            20                  25                  30

Gly Ser Ala Ala Ala Pro Pro Glu Val Leu Pro Thr Leu Arg Glu
            35                  40                  45

Trp Gln Gly Gly Gln Gly Glu Phe Thr Leu Thr Asp Arg Ala Gly Ile
50                  55                  60

Val Leu Asp Gly Val Arg Asp Ser Arg Thr Ala Ala Asp Ala Arg Arg
65                  70                  75                  80

Phe Ala Gly Glu Leu Asn Gly Lys Ala Ser Val Ser Gln Gly Arg Ala
            85                  90                  95

Ala Arg Pro Gly Asp Ile Val Leu Arg Gln Asp Pro Ala Gln Lys Gly
            100                 105                 110

Leu Leu Gly Ala Glu Gly Tyr Arg Leu Thr Val Gly Thr Arg Ile Thr
            115                 120                 125

Val Thr Ala Ala Thr Ser Thr Gly Val Phe Tyr Gly Thr Arg Thr Val
            130                 135                 140
```

-continued

```
Leu Gln Leu Leu Asn Asp Asp Gly Arg Ala Ala Arg Gly Ser Ala Thr
145                 150                 155                 160

Asp Val Pro Ala Tyr Arg Glu Arg Gly Val Gly Val Cys Ala Cys Tyr
                165                 170                 175

Ile Asn Ile Ser Thr Gln Trp Phe Glu Arg Leu Met Lys Asp Met Ala
            180                 185                 190

Ser Gln Lys Leu Asn Gln Leu Trp Ile Glu Ala Lys Val Lys Ser Asp
        195                 200                 205

Thr Asp Pro Ala Ser Ala Phe Trp Gly Tyr Tyr Thr Lys Pro Gln Val
210                 215                 220

Arg Thr Leu Val Ala Met Ala Arg Lys Tyr His Ile Glu Leu Val Pro
225                 230                 235                 240

Glu Ile Asn Ser Pro Gly His Met Asp Thr Tyr Leu Glu Asn His Pro
                245                 250                 255

Glu Leu Gln Leu Lys Asp Arg Asp Gly Val Ala Ser Pro Pro Arg Leu
            260                 265                 270

Asp Ile Ser Arg Pro Glu Ala Leu Ala Tyr Tyr Thr Ser Met Val Asp
        275                 280                 285

Glu Ala Leu Lys Val Trp Asp Ser Arg Tyr Trp His Met Gly Ala Asp
290                 295                 300

Glu Tyr Met Ile Gly Ser Ser Tyr Pro Asp Tyr Pro Gln Leu Gln Ala
305                 310                 315                 320

Ala Ala Arg Ala Lys Phe Gly Ala Ser Ala Thr Pro Asp Asp Leu Phe
                325                 330                 335

Thr Asp Phe Ile Asn Gln Val Asn Ala His Val Lys Ala Asp Gly Arg
            340                 345                 350

Ser Leu Arg Ile Trp Asn Asp Gly Leu Ala Gly Lys Asn Ala Val Val
        355                 360                 365

Pro Leu Asp Arg Asp Ile Thr Val Glu His Trp Leu Ser Gly Gly Ser
370                 375                 380

Ile Gln Gln Pro Ser Ser Leu Leu Ala Glu Gly Arg Pro Val Met Asn
385                 390                 395                 400

Ser Ala Tyr Ser Leu Tyr Leu Val Arg Gly Gly Phe Thr Met Gln Thr
                405                 410                 415

Gln Lys Leu Tyr Glu Ser Asp Trp Thr Pro Leu Arg Phe Glu Gly Gln
            420                 425                 430

Thr Leu Thr Gln Gly Ala Ala Asn Leu Thr Gly Ala Lys Ile Ser Leu
        435                 440                 445

Trp Pro Asp Ser Ala Ala Ala Glu Thr Glu Asn Glu Val Glu Thr Lys
450                 455                 460

Val Phe Met Pro Leu Arg Phe Val Ala Gln Ala Thr Trp Gly Gly Pro
465                 470                 475                 480

Lys Pro Ser Pro Thr Tyr Ala Gly Phe Glu Ala Leu Ala Arg Lys Ile
                485                 490                 495

Gly His Ala Pro Gly Trp Glu Asn Thr Asp Arg Thr Pro Leu Ala Asp
            500                 505                 510

Gly Thr Tyr Arg Leu Thr Thr Gly Ala Lys Ala Leu Ala Pro Thr Ala
        515                 520                 525

Asp Ala Gly Val Ser Leu Val Lys Asn Ser Ala Ala Ser Trp Ala Leu
530                 535                 540

Thr Ala Thr Ala Asp Gly Tyr Tyr Thr Val Arg Ser Thr Glu Ser Gly
545                 550                 555                 560

Gln Cys Leu Asp Ala Val Arg Gly Lys Lys Tyr Leu Gly Ala Pro Leu
```

-continued

```
                565                 570                 575
Glu Val Gly Ala Glu Leu Ser Leu Ala Asn Cys Ser Thr Thr Ala Arg
            580                 585                 590

Thr Gln Arg Trp Gln Leu Asp Thr Gly Ala Gly Ala Leu Thr Leu Arg
            595                 600                 605

Asn Ala Ile Ser Gln Leu His Leu Thr Glu Arg Ala Ser Asp Gly Ala
            610                 615                 620

Ala Val Gln Thr Thr Gly Ala Thr Arg Leu Thr Ala Arg Ala Ala
625                 630                 635

<210> SEQ ID NO 19
<211> LENGTH: 699
<212> TYPE: PRT
<213> ORGANISM: Bacillus circulans
<220> FEATURE:
<223> OTHER INFORMATION: Chitinase1 [Bacillus circulans]
<300> PUBLICATION INFORMATION:
<308> DATABASE ACCESSION NUMBER: gi 142688
<300> PUBLICATION INFORMATION:
<308> DATABASE ACCESSION NUMBER: AAA81528.1

<400> SEQUENCE: 19

Met Ile Asn Leu Asn Lys His Thr Ala Phe Lys Thr Ala Lys Phe
1               5                   10                  15

Phe Leu Gly Leu Ser Leu Leu Leu Ser Val Ile Val Pro Ser Phe Ala
            20                  25                  30

Leu Gln Pro Ala Thr Ala Glu Ala Ala Asp Ser Tyr Lys Ile Val Gly
        35                  40                  45

Tyr Tyr Pro Ser Trp Ala Ala Tyr Gly Arg Asn Tyr Asn Val Ala Asp
    50                  55                  60

Ile Asp Pro Thr Lys Val Thr His Ile Asn Tyr Ala Phe Ala Asp Ile
65                  70                  75                  80

Cys Trp Asn Gly Ile His Gly Asn Pro Asp Pro Ser Gly Pro Asn Pro
                85                  90                  95

Val Thr Trp Thr Cys Gln Asn Glu Lys Ser Gln Thr Ile Asn Val Pro
            100                 105                 110

Asn Gly Thr Ile Val Leu Gly Asp Pro Trp Ile Asp Thr Gly Lys Thr
        115                 120                 125

Phe Ala Gly Asp Thr Trp Asp Gln Pro Ile Ala Gly Asn Ile Asn Gln
    130                 135                 140

Leu Asn Lys Leu Lys Gln Thr Asn Pro Asn Leu Lys Thr Ile Ile Ser
145                 150                 155                 160

Val Gly Gly Trp Thr Trp Ser Asn Arg Phe Ser Asp Val Ala Ala Thr
                165                 170                 175

Ala Ala Thr Arg Glu Val Phe Ala Asn Ser Ala Val Asp Phe Leu Arg
            180                 185                 190

Lys Tyr Asn Phe Asp Gly Val Asp Leu Asp Trp Glu Tyr Pro Val Ser
        195                 200                 205

Gly Gly Leu Asp Gly Asn Ser Lys Arg Pro Glu Asp Lys Gln Asn Tyr
    210                 215                 220

Thr Leu Leu Leu Ser Lys Ile Arg Glu Lys Leu Asp Ala Ala Gly Ala
225                 230                 235                 240

Val Asp Gly Lys Lys Tyr Leu Leu Thr Ile Ala Ser Gly Ala Ser Ala
                245                 250                 255

Thr Tyr Ala Ala Asn Thr Glu Leu Ala Lys Ile Ala Ala Ile Val Asp
            260                 265                 270
```

-continued

```
Trp Ile Asn Ile Met Thr Tyr Asp Phe Asn Gly Ala Trp Gln Lys Ile
            275                 280                 285
Ser Ala His Asn Ala Pro Leu Asn Tyr Asp Pro Ala Ser Ala Ala
    290                 295                 300
Gly Val Pro Asp Ala Asn Thr Phe Asn Val Ala Ala Gly Ala Gln Gly
305                 310                 315                 320
His Leu Asp Ala Gly Val Pro Ala Ala Lys Leu Val Leu Gly Val Pro
                325                 330                 335
Phe Tyr Gly Arg Gly Trp Asp Gly Cys Ala Gln Ala Gly Asn Gly Gln
                340                 345                 350
Tyr Gln Thr Cys Thr Gly Gly Ser Ser Val Gly Thr Trp Glu Ala Gly
            355                 360                 365
Ser Phe Asp Phe Tyr Asp Leu Glu Ala Asn Tyr Ile Asn Lys Asn Gly
    370                 375                 380
Tyr Thr Arg Tyr Trp Asn Asp Thr Ala Lys Val Pro Tyr Leu Tyr Asn
385                 390                 395                 400
Ala Ser Asn Lys Arg Phe Ile Ser Tyr Asp Asp Ala Glu Ser Val Gly
                405                 410                 415
Tyr Lys Thr Ala Tyr Ile Lys Ser Lys Gly Leu Gly Gly Ala Met Phe
            420                 425                 430
Trp Glu Leu Ser Gly Asp Arg Asn Lys Thr Leu Gln Asn Lys Leu Lys
    435                 440                 445
Ala Asp Leu Pro Thr Gly Gly Thr Val Pro Pro Val Asp Thr Thr Ala
    450                 455                 460
Pro Ser Val Pro Gly Asn Ala Arg Ser Thr Gly Val Thr Ala Asn Ser
465                 470                 475                 480
Val Thr Leu Ala Trp Asn Ala Ser Thr Asp Asn Val Gly Val Thr Gly
                485                 490                 495
Tyr Asn Val Tyr Asn Gly Ala Asn Leu Ala Thr Ser Val Thr Gly Thr
                500                 505                 510
Thr Ala Thr Ile Ser Gly Leu Thr Ala Gly Thr Ser Tyr Thr Phe Thr
            515                 520                 525
Ile Lys Ala Lys Asp Ala Ala Gly Asn Leu Ser Ala Ala Ser Asn Ala
    530                 535                 540
Val Thr Val Ser Thr Thr Ala Gln Pro Gly Gly Asp Thr Gln Ala Pro
545                 550                 555                 560
Thr Ala Pro Thr Asn Leu Ala Ser Thr Ala Gln Thr Ser Ser Ile
                565                 570                 575
Thr Leu Ser Trp Thr Ala Ser Thr Asp Asn Val Gly Val Thr Gly Tyr
            580                 585                 590
Asp Val Tyr Asn Gly Thr Ala Leu Ala Thr Thr Val Thr Gly Thr Thr
                595                 600                 605
Ala Thr Ile Ser Gly Leu Ala Ala Asp Thr Ser Tyr Thr Phe Thr Val
    610                 615                 620
Lys Ala Lys Asp Ala Ala Gly Asn Val Ser Ala Ala Ser Asn Ala Val
625                 630                 635                 640
Ser Val Lys Thr Ala Ala Glu Thr Thr Asn Pro Gly Val Ser Ala Trp
                645                 650                 655
Gln Val Asn Thr Ala Tyr Thr Ala Gly Gln Leu Val Thr Tyr Asn Gly
                660                 665                 670
Lys Thr Tyr Lys Cys Leu Gln Pro His Thr Ser Leu Ala Gly Trp Glu
            675                 680                 685
Pro Ser Asn Val Pro Ala Leu Trp Gln Leu Gln
```

-continued

```
         690                 695

<210> SEQ ID NO 20
<211> LENGTH: 702
<212> TYPE: PRT
<213> ORGANISM: Trypanosoma congolense
<220> FEATURE:
<223> OTHER INFORMATION: Trans-sialidase [Trypanosoma congolense]
<300> PUBLICATION INFORMATION:
<308> DATABASE ACCESSION NUMBER: gi 343957998
<300> PUBLICATION INFORMATION:
<308> DATABASE ACCESSION NUMBER: CCD30509.1

<400> SEQUENCE: 20

Gln Cys Cys Asp His Met His Ala Thr Ala Ala Val Gly Thr Thr His
1               5                   10                  15

Gln Ala Leu Leu Trp Gly Ser Lys Trp Ala Leu Arg Asn Lys Thr Thr
            20                  25                  30

Pro Lys Asp Gly Glu Val Trp Trp Ser Asn Pro Gln Pro Gly Trp Lys
        35                  40                  45

Glu Val Tyr Asp Asp Glu Trp Glu Glu Trp Phe Met Glu Gln Lys Gly
    50                  55                  60

Pro Thr Gly Val Asn Gly Val Arg Thr Glu Trp Tyr Arg Arg Met Lys
65                  70                  75                  80

Asp Gly Tyr Ile Leu Val Gly Gly Pro Lys Leu Asn Ser Pro Asp Met
                85                  90                  95

Asn Ser Thr Gly Thr Thr Met Arg Thr Val His Ser Tyr Arg Ile Pro
            100                 105                 110

Ser Ile Val Glu Val Gly Gly Val Leu Met Cys Val Gly Asp Ala Arg
        115                 120                 125

Tyr Ile Thr Ser Thr Asp Tyr Phe Phe Thr Asp Thr Val Ala Ala Tyr
    130                 135                 140

Ser Thr Asp Gly Gly Arg Thr Trp Lys Arg Glu Val Ile Ile Pro Asn
145                 150                 155                 160

Gly Arg Val Asp Ala His Tyr Ser Arg Val Val Asp Pro Thr Val Val
                165                 170                 175

Ala Lys Gly Asn Asn Ile Tyr Val Leu Val Gly Arg Tyr Asn Val Thr
            180                 185                 190

Arg Gly Tyr Trp His Asn Lys Asn Asn Arg Ala Gly Val Ala Asp Trp
        195                 200                 205

Glu Pro Phe Val Tyr Lys Gly Thr Val Asn Val Gly Thr Lys Asp Asn
    210                 215                 220

Ala Thr Asp Val Ser Ile Ser Trp Glu Arg Thr Ala Leu Lys Ser Leu
225                 230                 235                 240

Tyr Asn Phe Pro Val Ser Gly Ser Pro Gly Thr Gln Phe Leu Gly Gly
                245                 250                 255

Ala Gly Gly Gly Val Val Thr Ser Asn Gly Thr Ile Val Leu Pro Val
            260                 265                 270

Gln Ala Arg Asn Lys Ala Asn Arg Val Val Ser Met Ile Leu Tyr Ser
        275                 280                 285

Ala Asp Asp Gly Lys Ser Trp His Phe Gly Lys Gly Glu Ala Gly Val
    290                 295                 300

Gly Thr Ser Glu Ala Ala Leu Thr Glu Trp Asp Gly Lys Leu Leu Ile
305                 310                 315                 320

Ser Ala Arg Ser Asp Gly Gly Gln Gly Tyr Arg Met Ile Phe Glu Ser
                325                 330                 335
```

```
Ser Asp Leu Gly Ala Thr Trp Lys Glu Met Leu Asn Ser Ile Ser Arg
            340                 345                 350

Val Ile Gly Asn Ser Pro Gly Arg Ser Gly Pro Gly Ser Ser Ser Gly
355                 360                 365

Phe Ile Thr Val Thr Val Glu Gly Val Pro Val Met Leu Leu Thr His
        370                 375                 380

Pro Lys Asn Leu Lys Gly Ser Tyr Tyr Arg Asp Arg Leu Gln Met Trp
385                 390                 395                 400

Met Thr Asp Gly Asn Arg Met Trp His Val Gly Gln Val Ser Glu Gly
            405                 410                 415

Asp Asp Asn Ser Ala Tyr Ser Ser Leu Leu Tyr Thr Pro Asp Gly Val
                420                 425                 430

Leu Tyr Cys Leu His Glu Gln Asn Ile Asp Glu Val Tyr Ser Leu His
            435                 440                 445

Leu Val Arg Leu Val Asp Glu Leu Lys Ser Ile Lys Ser Thr Ala Leu
        450                 455                 460

Val Trp Lys Ala Gln Asp Glu Leu Leu Leu Gly Asn Cys Leu Pro Gly
465                 470                 475                 480

Asp Lys Tyr Asp Pro Gly Cys Asp Gly Ile Pro Thr Ala Gly Leu Ala
            485                 490                 495

Gly Leu Leu Val Gly Pro Leu Thr Glu Lys Thr Trp Pro Asp Ala Tyr
                500                 505                 510

Arg Cys Val Asn Ala Ala Thr Ser Gly Ala Val Ser Thr Ala Glu Gly
            515                 520                 525

Val Arg Leu Asp Val Gly Gly Gly His Val Val Trp Pro Val Ser
        530                 535                 540

Glu Gln Gly Gln Asp Gln Arg Tyr Tyr Phe Thr Asn Ser Glu Phe Thr
545                 550                 555                 560

Leu Ala Val Thr Val Arg Phe Asp Glu Met Pro Gln Gly Glu Leu Pro
            565                 570                 575

Leu Leu Gly Phe Val Asn Arg Glu Gly Lys Val Lys Lys Ile Leu Lys
                580                 585                 590

Val Ser Leu Ser Gly Val Glu Trp Leu Leu Ala Tyr Gly Asn Glu Tyr
            595                 600                 605

Asn Ser Thr Ala Ala Glu Pro Leu Asp Val Asn Glu Ser His Gln Val
610                 615                 620

Val Leu Ala Leu His Asp Gly Ile Val Ser Leu His Val Asp Gly Gly
625                 630                 635                 640

Asn Thr Thr Ala Thr Val Ser Val Arg Val Ala Ser Pro Ala Glu Leu
            645                 650                 655

Leu Asn Ile His His Leu Phe Val Gly Thr Pro Val Asp Gly Gly Ala
                660                 665                 670

Lys Glu His Ala Asn Ile Thr Val Ser Asn Val Leu Val Tyr Asn Arg
            675                 680                 685

Pro Leu Arg Gly Val Glu Leu Leu Gly Leu Phe Ala Asn Arg
690                 695                 700
```

```
<210> SEQ ID NO 21
<211> LENGTH: 702
<212> TYPE: PRT
<213> ORGANISM: Trypanosoma congolense
<220> FEATURE:
<223> OTHER INFORMATION: Trans-sialidase [Trypanosoma congolense]
<300> PUBLICATION INFORMATION:
<308> DATABASE ACCESSION NUMBER: gi 343958004
```

<300> PUBLICATION INFORMATION:
<308> DATABASE ACCESSION NUMBER: CCD30512.1

<400> SEQUENCE: 21

| | | | | | | | | | | | | | | | |
|---|---|---|---|---|---|---|---|---|---|---|---|---|---|---|---|
| Gln | Cys | Cys | Asp | His | Met | His | Ala | Thr | Ala | Ala | Val | Gly | Thr | Thr | His |
| 1 | | | | 5 | | | | | 10 | | | | | 15 | |
| Gln | Ala | Leu | Leu | Trp | Gly | Ser | Lys | Trp | Ala | Leu | Arg | Asn | Lys | Thr | Thr |
| | | | 20 | | | | | 25 | | | | | 30 | | |
| Pro | Lys | Asp | Gly | Glu | Val | Trp | Trp | Ser | Asn | Pro | Gln | Pro | Gly | Trp | Lys |
| | | 35 | | | | | 40 | | | | | 45 | | | |
| Glu | Val | Tyr | Asp | Asp | Glu | Trp | Glu | Trp | Phe | Met | Glu | Gln | Glu | Gly | |
| | 50 | | | | | 55 | | | | | 60 | | | | |
| Pro | Thr | Gly | Val | Asn | Gly | Val | Arg | Gly | Glu | Trp | Tyr | Arg | Arg | Met | Thr |
| 65 | | | | | 70 | | | | | 75 | | | | | 80 |
| Asp | Gly | Tyr | Ile | Leu | Val | Gly | Pro | Lys | Leu | Asn | Ser | Pro | Asp | Met | |
| | | | | 85 | | | | | 90 | | | | | 95 | |
| Asn | Ser | Thr | Gly | Thr | Thr | Met | Arg | Thr | Val | His | Ser | Tyr | Arg | Ile | Pro |
| | | | 100 | | | | | 105 | | | | | 110 | | |
| Ser | Ile | Val | Glu | Val | Gly | Gly | Val | Leu | Met | Cys | Val | Gly | Asp | Ala | Arg |
| | | | 115 | | | | | 120 | | | | | 125 | | |
| Tyr | Ile | Thr | Ser | Thr | Asp | Tyr | Phe | Phe | Thr | Asp | Thr | Val | Ala | Ala | Tyr |
| | | 130 | | | | | 135 | | | | | 140 | | | |
| Ser | Thr | Asp | Gly | Arg | Thr | Trp | Lys | Arg | Glu | Val | Ile | Ile | Pro | Asn | |
| 145 | | | | | 150 | | | | | 155 | | | | | 160 |
| Gly | Arg | Val | Asp | Ala | His | Tyr | Ser | Arg | Val | Val | Asp | Pro | Thr | Val | Val |
| | | | | 165 | | | | | 170 | | | | | 175 | |
| Ala | Lys | Gly | Asn | Asn | Ile | Tyr | Val | Leu | Val | Gly | Arg | Tyr | Asn | Val | Thr |
| | | | 180 | | | | | 185 | | | | | 190 | | |
| Arg | Gly | Tyr | Trp | His | Asn | Lys | Asn | Asn | Arg | Ala | Gly | Val | Ala | Asp | Trp |
| | | 195 | | | | | 200 | | | | | 205 | | | |
| Glu | Pro | Phe | Val | Tyr | Lys | Gly | Thr | Val | Asn | Val | Gly | Thr | Lys | Asp | Asn |
| | 210 | | | | | 215 | | | | | 220 | | | | |
| Ala | Thr | Asp | Val | Ser | Ile | Ser | Trp | Glu | Arg | Thr | Ala | Leu | Lys | Ser | Leu |
| 225 | | | | | 230 | | | | | 235 | | | | | 240 |
| Tyr | Asn | Phe | Pro | Val | Ser | Gly | Ser | Pro | Gly | Thr | Gln | Phe | Leu | Gly | Gly |
| | | | 245 | | | | | 250 | | | | | 255 | | |
| Ala | Gly | Gly | Gly | Val | Val | Thr | Ser | Asn | Gly | Thr | Ile | Val | Leu | Pro | Val |
| | | | 260 | | | | | 265 | | | | | 270 | | |
| Gln | Ala | Arg | Asn | Lys | Ala | Asn | Arg | Val | Val | Ser | Met | Ile | Leu | Tyr | Ser |
| | | 275 | | | | | 280 | | | | | 285 | | | |
| Ala | Asp | Asp | Gly | Lys | Ser | Trp | His | Phe | Gly | Lys | Gly | Glu | Ala | Gly | Val |
| | | 290 | | | | | 295 | | | | | 300 | | | |
| Gly | Thr | Ser | Glu | Ala | Ala | Leu | Thr | Glu | Trp | Asp | Gly | Lys | Leu | Leu | Ile |
| 305 | | | | | 310 | | | | | 315 | | | | | 320 |
| Ser | Ala | Arg | Ser | Asp | Gly | Gly | Gln | Gly | Tyr | Arg | Met | Ile | Phe | Glu | Ser |
| | | | 325 | | | | | 330 | | | | | 335 | | |
| Ser | Asp | Leu | Gly | Ala | Thr | Trp | Lys | Glu | Met | Leu | Asn | Ser | Ile | Ser | Arg |
| | | | 340 | | | | | 345 | | | | | 350 | | |
| Val | Ile | Gly | Asn | Ser | Pro | Gly | Arg | Ser | Gly | Pro | Gly | Ser | Ser | Ser | Gly |
| | | | 355 | | | | | 360 | | | | | 365 | | |
| Phe | Ile | Thr | Val | Thr | Val | Glu | Gly | Val | Pro | Val | Met | Leu | Leu | Thr | His |
| | | 370 | | | | | 375 | | | | | 380 | | | |
| Pro | Lys | Asn | Phe | Lys | Gly | Ser | Tyr | Tyr | Arg | Asp | Arg | Leu | Gln | Met | Trp |

```
385                 390                 395                 400
Met Thr Asp Gly Asn Arg Met Trp His Val Gly Gln Val Ser Glu Gly
                405                 410                 415

Asp Asp Asn Ser Ala Tyr Ser Ser Leu Leu Tyr Thr Pro Asp Gly Val
                420                 425                 430

Leu Tyr Cys Leu His Glu Gln Asn Ile Asp Glu Val Tyr Ser Leu His
            435                 440                 445

Leu Val Arg Leu Val Asp Glu Leu Lys Ser Ile Lys Ser Thr Ala Leu
        450                 455                 460

Val Trp Lys Ala Gln Asp Glu Leu Leu Leu Gly Asn Cys Leu Pro Gly
465                 470                 475                 480

Asp Lys Tyr Asp Pro Gly Cys Asp Gly Ile Pro Thr Ala Gly Leu Ala
                485                 490                 495

Gly Leu Leu Val Gly Pro Leu Thr Glu Lys Thr Trp Pro Asp Ala Tyr
                500                 505                 510

Arg Cys Val Asn Ala Ala Thr Ser Gly Ala Val Ser Thr Ala Glu Gly
            515                 520                 525

Val Arg Leu Asp Val Gly Gly Gly His Val Val Trp Pro Val Ser
    530                 535                 540

Glu Gln Gly Gln Asp Gln Arg Tyr Tyr Phe Thr Asn Ser Glu Phe Thr
545                 550                 555                 560

Leu Ala Val Thr Val Arg Phe Asp Glu Met Pro His Gly Glu Leu Pro
                565                 570                 575

Leu Leu Gly Phe Val Asn Arg Lys Asp Gln Val Lys Lys Ile Leu Lys
            580                 585                 590

Val Ser Leu Ser Gly Val Glu Trp Leu Leu Ala Tyr Gly Asn Glu Tyr
        595                 600                 605

Asn Ser Thr Ala Ala Glu Pro Leu Asn Val Asn Glu Ser His Gln Val
        610                 615                 620

Val Leu Thr Leu His Asp Gly Ile Val Ser Leu His Val Asp Gly Gly
625                 630                 635                 640

Asn Met Thr Ala Thr Val Ser Val Arg Val Ala Ser Pro Ala Glu Leu
                645                 650                 655

Leu Asn Ile His His Leu Phe Val Gly Thr Pro Val Asp Gly Gly Ala
            660                 665                 670

Lys Glu His Ala Asn Ile Thr Val Ser Asn Val Leu Val Tyr Asn Arg
        675                 680                 685

Pro Leu Arg Gly Val Glu Leu Leu Gly Leu Phe Ala Asn Arg
        690                 695                 700
```

METHOD FOR GENERATING HUMAN MILK OLIGOSACCHARIDES (HMOS) OR PRECURSORS THEREOF

CROSS REFERENCE TO RELATED APPLICATIONS

This application is the National Phase entry of PCT/IB2012/052400, which claims priority to European Patent Application No. 11166135.1 filed Ma 13, 2011 and International Patent Application No. PCT/IB2012/051314, filed Mar. 19, 2012. The content of these applications is incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 27, 2014, is named 011765-0428049_SL.txt and is 157,309 bytes in size.

FIELD OF THE INVENTION

The present invention relates to a method for generating human milk oligosaccharides (HMOs) or precursors thereof and to compounds suitable for use in or obtainable by the method of the present invention. The invention furthermore describes uses of and products involving such compounds.

BACKGROUND OF THE INVENTION

Human milk oligosaccharides (HMOs) have attracted much interest in the past few years. In particular, commercialization efforts for the synthesis of these complex carbohydrates including secreted oligosaccharides have increased significantly due to their roles in numerous biological processes occurring in the human organism. One prominent natural human source of such complex oligosaccharides is mammalian milk. Mammalian milk contains up to 10% carbohydrate, of which the disaccharide, lactose (Gal($\beta$1-4) Glc), is usually a prominent component. Milk and colostrum also contain lesser amounts of other saccharides, referred to as milk oligosaccharides, nearly all of which have a lactose unit at their reducing end to which GlcNAc, Gal, Fuc and/or Neu5Ac or Neu5Gc residues can be attached (Messer and Urashima, 2002, Trends Glycosci. Glycotech, 14, 153-176; and Urashima et al., Advanced Dairy Chemistry, Volume 3: Lactose, Water, Salts and Minor Constituents, 2009, pp. 295-349).

To date, the structures of at least 115 oligosaccharides of human milk have been determined, while mass spectra (MS) data have suggested the presence of almost 130 oligosaccharides in human milk or colostrums (Newburg and Neubauer, 1995, Carbohydrates in milks: Analysis, quantities and significance. In: Handbook of Milk Composition (R. G. Jensen, ed.), pp. 273-249, Academic Press, San Diego, USA). Moreover, matrix-assisted laser desorption/ionization time-of-flight mass spectrometry (MALDI-TOFMS) analyses suggest that polysaccharides, consisting of more than 50 monosaccharide residues as indicated by size exclusion chromatography, are also present in human milk. Therefore, considerably more than 130 different saccharides are probably present in human milk (see also Urashima et al., Advanced Dairy Chemistry, Volume 3: Lactose, Water, Salts and Minor Constituents, 2009, pp. 295-349; and TADASU URASHIMA et al, MILK OLIGOSACCHARIDES, Nova Biomedical Books, New York, 2011, ISBN: 978-1-61122-831-1).

The 115 human milk oligosaccharides of which the structures have been determined to date, can be grouped into 13 series based on their core structures. Such 13 core structures are exemplarily shown in Table 1 below:

TABLE 1

13 different core structures of human milk oligosaccharides (HMOs)

| No | Core name | Core structure |
|---|---|---|
| 1 | lactose (Lac) | Gal$\beta$1-4Glc |
| 2 | lacto-N-tetraose (LNT) | Gal$\beta$1-3GlcNAc$\beta$1-3Gal$\beta$1-4Glc |
| 3 | lacto-N-neotetraose (LNnT) | Gal$\beta$1-4GlcNAc$\beta$1-3Gal$\beta$1-4Glc |
| 4 | lacto-N-hexaose (LNH) | Gal$\beta$1-3GlcNAc$\beta$1-3(Gal$\beta$1-4GlcNAc$\beta$1-6)Gal$\beta$1-4Glc |
| 5 | lacto-N-neohexaose (LNnH) | Gal$\beta$1-4GlcNAc$\beta$1-3(Gal$\beta$1-4GlcNAc$\beta$1-6)Gal$\beta$1-4Glc |
| 6 | para-lacto-N-hexaose (para-LNH) | Gal$\beta$1-3GlcNAc$\beta$1-3Gal$\beta$1-4GlcNAc$\beta$1-3Gal$\beta$1-4Glc |
| 7 | para-lacto-N-neohexaose (para-LNnH) | Gal$\beta$1-4GlcNAc$\beta$1-3Gal$\beta$1-4GlcNAc$\beta$1-3Gal$\beta$1-4Glc |
| 8 | lacto-N-octaose (LNO) | Gal$\beta$1-3GlcNAc$\beta$1-3(Gal$\beta$1-4GlcNAc$\beta$1-3Gal$\beta$1-4GlcNAc$\beta$1-6)Gal$\beta$1-4Glc |
| 9 | lacto-N-neooctaose (LNnO) | Gal$\beta$1-4GlcNAc$\beta$1-3(Gal$\beta$1-3GlcNAc$\beta$1-3Gal$\beta$1-4GlcNAc$\beta$1-6)Gal$\beta$1-4Glc |
| 10 | Iso-lacto-N-octaose (iso-LNO) | Gal$\beta$1-3GlcNAc$\beta$1-3(Gal$\beta$1-3GlcNAc$\beta$1-3Gal$\beta$1-4GlcNAc$\beta$1-6)Gal$\beta$1-4Glc |
| 11 | para-lacto-N-octaose (para-LNO) | Gal$\beta$1-3GlcNAc$\beta$1-3Gal$\beta$1-4GlcNAc$\beta$1-3Gal$\beta$1-4GlcNAc$\beta$1-3Gal$\beta$1-4Glc |
| 12 | lacto-N-neodecaose (LNnD) | Gal$\beta$1-3GlcNAc$\beta$1-3[Gal$\beta$1-4GlcNAc$\beta$1-3(Gal$\beta$1-4GlcNAc$\beta$1-6)Gal$\beta$1-4GlcNAc$\beta$1-6]Gal$\beta$1-4Glc |
| 13 | lacto-N-decaose (LND) | Gal$\beta$1-3GlcNAc$\beta$1-3[Gal$\beta$1-3GlcNAc$\beta$1-3(Gal$\beta$1-4GlcNAc$\beta$1-6)Gal$\beta$1-4GlcNAc$\beta$1-6]Gal$\beta$1-4Glc |

As found by Urashima et al. (see also Urashima et al., Advanced Dairy Chemistry, Volume 3: Lactose, Water, Salts and Minor Constituents, 2009, pp. 295-349; and TADASU URASHIMA et al, MILK OLIGOSACCHARIDES, Nova Biomedical Books, New York, 2011, ISBN: 978-1-61122-831-1) the many variations of the oligosaccharides are constructed by the addition of a Neu5Ac$\beta$2-3/2-6 residue to Gal or GlcNAc, and of Fuc$\alpha$1-2/1-3/1-4 to Gal, GlcNAc or a reducing Glc of the core units. The main structural features of human milk oligosaccharides are the presence of oligosaccharides containing the type I unit (Gal($\beta$1-3)GlcNAc), as well as those containing the type II unit (Gal($\beta$1-4)GlcNAc), and oligosaccharides containing the type I predominate over those containing the type II unit. The milk oligosaccharides of other species investigated to date mostly exhibit the type II but not the type I unit.

The large variety of oligosaccharides in human milk and colostrum and the difference to other species, however, makes it difficult to prepare suitable replacements in foods, particularly in infant food formulae, which display at least part of the entire spectrum of human milk oligosaccharides. Furthermore, their recognized importance in the maturation of the immune system and their prognostic use as immunomodulators underlines their importance as a possible immunomodulator.

Accordingly, there is an urgent need in the art for the preparation of complex oligosaccharides and mixtures thereof, which resemble as much as possible or even reproduce the variety of complex oligosaccharides in human milk.

Many attempts have been carried out in this respect to produce individual HMOs via organo-chemical synthesis and, due to its stereoselectivity, via enzymatic means. Enzymatic means have been increasingly explored in the last two decades.

Notably, in biological systems, Leloir-type glycosyltransferases (GTs, EC 2.4.1.-) and glycosidases (also called glycoside hydrolases: GHs, EC 3.2.1.-) constitute the two major classes of carbohydrate-processing enzymes, which may be utilized in the production of HMOs. Both classes of enzymes act to transfer a glycosyl group from a donor to an acceptor resulting in oligosaccharide production. The use of glycosyltransferases for synthesis in industrial processes, however, is limited both by the availability of the desired enzymes due to problems with expression and solubility and the high costs of the activated donor sugars. These nucleotide donors may be typically generated in situ, but the process requires additional enzymes (see Hanson, S., et al., Trends Biochem Sci, 2004. 29(12): p. 656-63). In contrast to glycosyltransferases, glycosidases have a wide range of donor substrates employing usually monosaccharides, oligosaccharides or/and engineered substrates (i.e. substrates carrying various functional groups). They often display activity towards a large variety of carbohydrate and non-carbohydrats acceptors. Another advantage of the use of glycosidases compared to glycosyltransferases is their robustness and accessibility.

In vivo, glycosidases usually catalyze the hydrolysis of glycosidic linkages with either retention or inversion of stereochemical configuration in the product. In vitro, they can catalyse the formation of a new glycosidic bond either by transglycosylation or by reverse hydrolysis (ie condensation). Under kinetically controlled reactions these enzymes (typically, retaining glycosidases) can be used to form glycosidic linkages using a glycosyl donor activated by a good anomeric leaving group (e.g. nitrophenyl glycoside). In contrast, the thermodynamically controlled reverse hydrolysis uses high concentrations of free sugars. However, even though the appropriate application of glycosidases in the synthetic direction is of considerable interest, it remains challenging as optimal conditions and suitable substrates have to be found to drive the reaction in the desired direction and to avoid hydrolysis of the products.

Another approach to overcome this bottleneck and to make glycosidases more suitable for oligosaccharide synthesis has been recently developed by providing modified enzymes (variants). Thus, during these two past decades, protein engineering based on rational or combinatorial techniques has proven to be extremely powerful to generate biocatalysts with improved transglycosylation activity and efficiency.

The synthesis of Fucα1-3Galβ1-4Glc using p-nitrophenyl fucoside, lactose and α-fucosidase from *Alcaligenes* sp. has been reported by Murata et al. *Carbohydr. Res.* 320, 192 (1999). Synthesis of 2'-fucosyllactose using fucosyl fluoride, lactose and 1,2-α-L-fucosynthase has been disclosed in Wada et al. *FEBS Lett.* 582, 3739 (2008). Sialylation of lactose with p-nitrophenyl sialoside employing recombinant transsialidase from *T. cruzi* has been described by Neubacher et al. *Org. Biomol. Chem.* 3, 1551 (2005). Transsialylation of benzyl glycosides of galactosyl oligosaccharides has been claimed in WO 2012/007588. Direct conversion of lactose into LNT with p-nitrophenyl lacto-N-bioside using a lacto-N-biosidase from *Aureobacterium* sp. L-101 has been reported in Murata et al. *Glycoconj. J.* 16, 189 (1999). However, even though many organo-chemical syntheses or enzyme based syntheses for basic human milk oligosaccharide structures or their precursors have been published meanwhile, such synthesis methods still do not allow the preparation of complex mixtures of naturally occurring oligosaccharides or derivatives thereof. Preparing such mixtures on the basis of individually designed syntheses of single HMOs is furthermore costly and may not resemble the large variety of naturally occurring HMOs.

Accordingly, it is an object underlying the present invention to provide a method, which allows the provision of a larger variety of human milk oligosaccharides than is obtained by prior art methods, preferably in a cost efficient manner, and preferably on an industrial scale.

BRIEF DESCRIPTION OF THE FIGURES

The following figures are intended to illustrate the invention further. They are not intended to limit the subject matter of the invention thereto.

FIG. 3: shows the NMR spectrum of benzyl 3'''-O-sialyl-β-LNnT.

DESCRIPTION OF THE INVENTION

Figure 1:
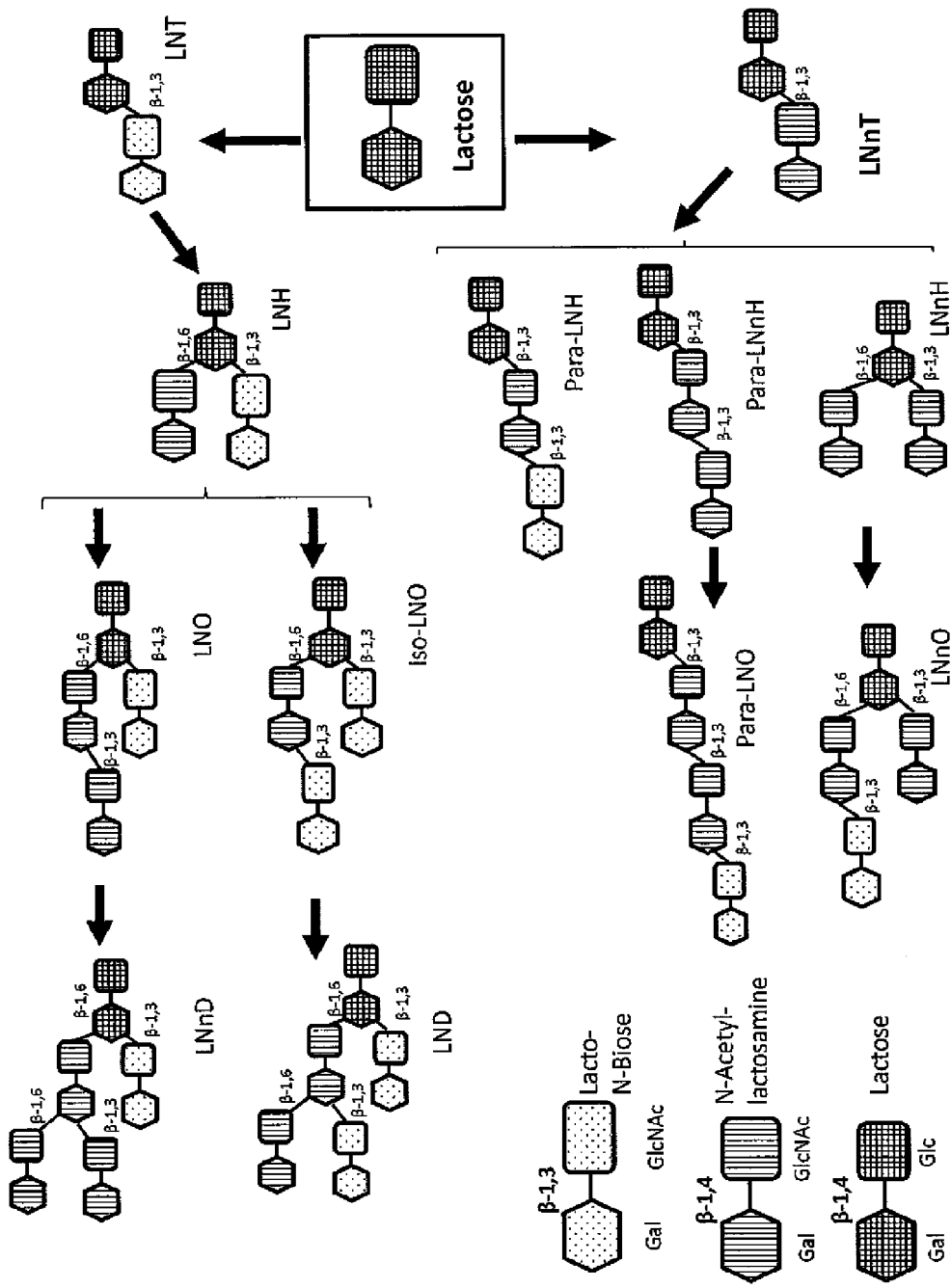
FIG. 1: depicts the presently known 13 core structures of human milk oligosaccharides (HMOs).
Figure 2:
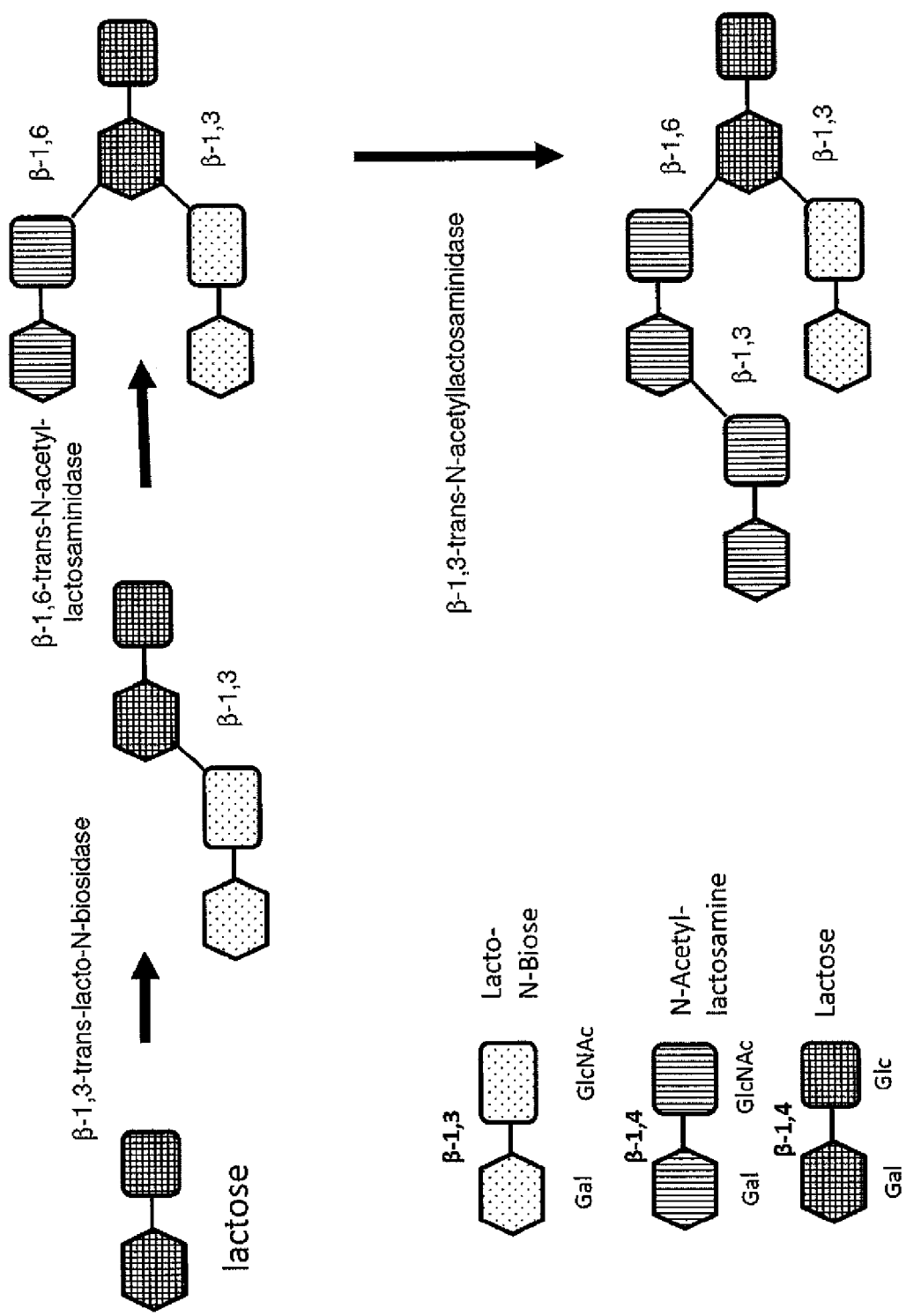
FIG. 2: depicts an exemplary synthesis of HMOs using lactose, N-acetyllactosaminyl donor and lacto-N-biosyl donor with the enzymes β-1,3-trans-lacto-N-biosidase, β-1, 3-trans-N-acetyllactosaminidase, and β-1,6-trans-N-acetyllactosaminidase.

According to a first aspect, the present invention provides a method for generating one or more human milk oligosaccharides (HMOs) or derivatives or precursors thereof, that is making one or more human milk oligosaccharides (HMOs) or derivatives or precursors thereof, the method comprising the steps of a) providing at least one compound as a universal donor selected from the group consisting of a compound of any of formulae 5 to 10

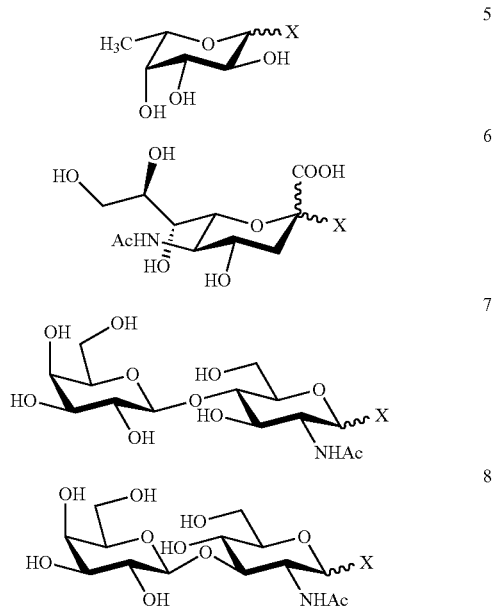

-continued

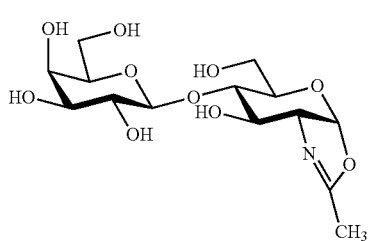

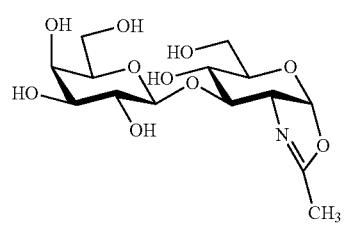

and salts thereof, wherein X is selected from the group consisting of azide, fluoro, optionally substituted phenoxy, optionally substituted pyridinyloxy, group A, group B, group C and group D

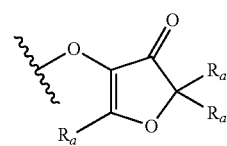   A

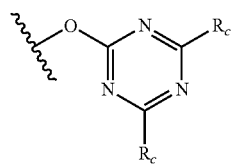   B

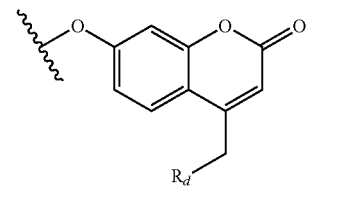   C

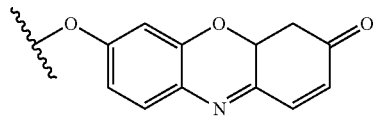   D wherein $R_a$ is independently H or alkyl, or two vicinal $R_a$ groups represent a $=C(R_b)_2$ group, wherein $R_b$ is independently H or alkyl, $R_c$ is independently selected from the group consisting of alkoxy, amino, alkylamino and dialkylamino, $R_d$ is selected from the group consisting of H, alkyl and —C(=O)$R_e$, wherein $R_e$ is OH, alkoxy, amino, alkylamino, dialkylamino, hydrazino, alkylhydrazino, dialkylhydrazino or trialkylhydrazino.

b) providing at least one compound as an acceptor selected from the group consisting of:
lactose
lactose derivatives of the following formula:

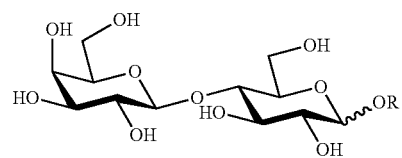

wherein R is a group removable by hydrogenolysis,
LNT:

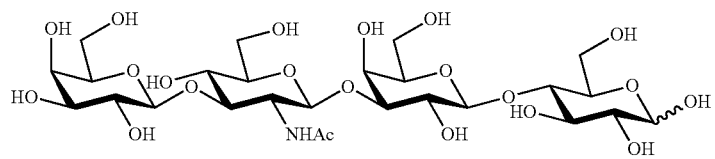

LNT derivatives of the formula:

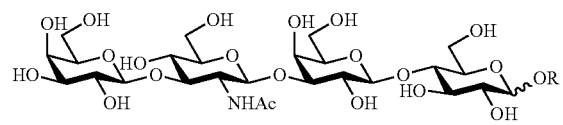

wherein R is a group removable by hydrogenolysis, or salts thereof

LNnT:

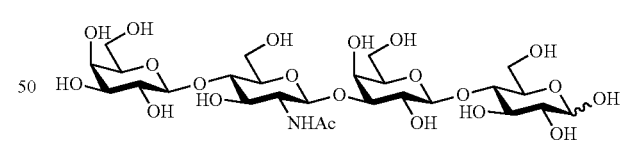

LNnT derivatives of the formula:

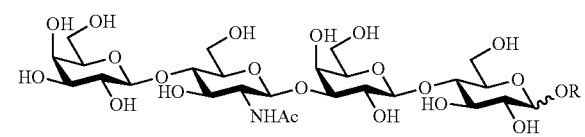

wherein R is a group removable by hydrogenolysis, or salts thereof c) providing at least one enzyme comprising a transglycosidase activity and/or a glycosynthase activity;

d) preparing a mixture of the donor(s), acceptor(s) and enzyme(s), provided in steps a), b) and c)

e) incubating the mixture prepared according to step d);

f) optionally: repeating any of steps a) to e), with the mixture obtained according to step e);

g) optionally subjecting the mixture obtained as a result of step e) or f) to a hydrogenolysis reaction.

According to a preferred embodiment of the first aspect, the present invention provides a method for generating one or more human milk oligosaccharides (HMOs) or derivatives or precursors thereof, that is making one or more human milk oligosaccharides (HMOs) or derivatives or precursors thereof, the method comprising the steps of a) providing at least one compound as a universal donor selected from the group consisting of a compound of any of formulae 5 to 10 defined above, or salts thereof, b) providing at least one compound as an acceptor selected from the group consisting of:
   lactose
   lactose derivatives of the following formula:

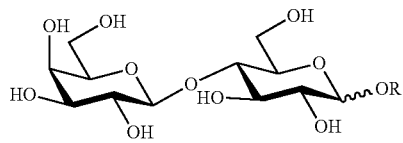

wherein R is a group removable by hydrogenolysis,
LNT:

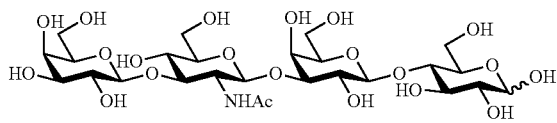

LNT derivatives of the formula:

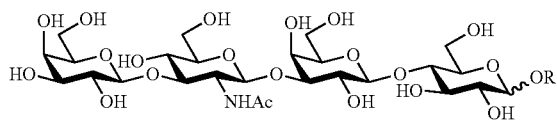

wherein R is a group removable by hydrogenolysis, or salts thereof
LNnT:

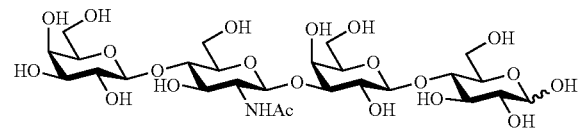

LNnT derivatives of the formula:

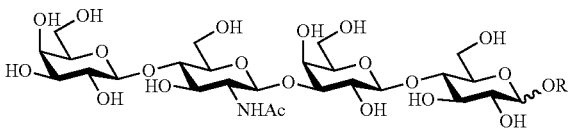

wherein R is a group removable by hydrogenolysis, c) providing at least one enzyme comprising a transglycosidase activity and/or a glycosynthase activity;

d) preparing a mixture of the donor(s), acceptor(s) and enzyme(s), provided in steps a), b) and c);

e) incubating the mixture prepared according to step d);

f) repeating at least one of the steps a) to c), then repeating step d) and step e) in the case where:

f-a) a single compound of formula 5 is provided as the universal donor in step a), a single acceptor is provided according to step b), the enzyme comprising a transglycosidase activity and/or a glycosynthase activity added in step c) is an enzyme having a trans-fucosidase and/or fucosynthase activity, and a single HMO or derivative or precursor thereof is made as a result of step e); or f-b) a single compound of formula 6 is provided as the universal donor in step a), a single acceptor is provided according to step b), the enzyme comprising a transglycosidase activity and/or a glycosynthase activity added in step c) is an enzyme having a trans-sialidase activity, and a single HMO or derivative or precursor thereof is made as a result of step e); or f-c) a single compound of formula 8 is provided as the universal donor in step a), a single acceptor is provided according to step b), the enzyme comprising a transglycosidase activity and/or a glycosynthase activity added in step c) is an enzyme having a trans-lacto-N-biosidase activity, and a single HMO or derivative or precursor thereof is made as a result of step e);

g) optionally: repeating at least one of the steps a) to c), then repeating step d) and step e) with the mixture obtained according to step e) or f);

h) optionally subjecting the mixture obtained as a result of step e), f) or g) to a hydrogenolysis reaction.

Suitably, the step f) is conducted where a single donor is provided in step a), a single acceptor is provided in step b), the enzyme provided in step c) is a single enzyme comprising a transglycosidase activity and/or a glycosynthase activity, and a single HMO or derivative or precursor thereof is made as a result of step e).

According to a more preferred embodiment of the first aspect, the present invention provides a method for generating more human milk oligosaccharides (HMOs) or derivatives or precursors thereof, that is making one or more human milk oligosaccharides (HMOs) or derivatives or precursors thereof, the method comprising the steps of a) providing at least one compound as a universal donor selected from the group consisting of a compound of any of formulae 5 to 10 defined above, or salts thereof, b) providing at least one compound as an acceptor selected from the group consisting of:
   lactose lactose derivatives of the following formula:

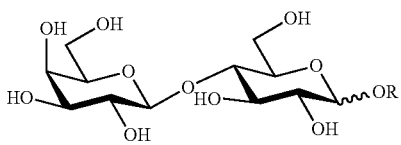

wherein R is a group removable by hydrogenolysis,
LNT:

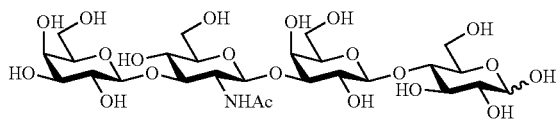

LNT derivatives of the formula:

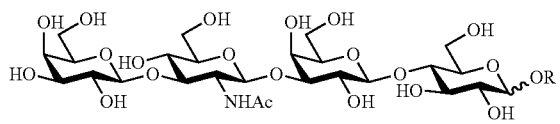

wherein R is a group removable by hydrogenolysis, or salts thereof
LNnT:

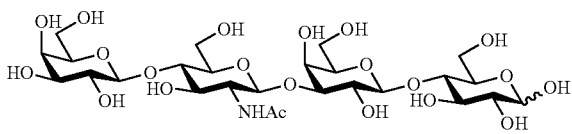

LNnT derivatives of the formula:

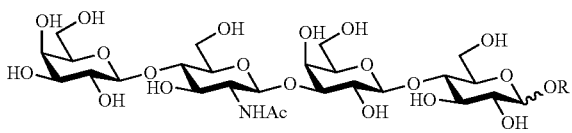

wherein R is a group removable by hydrogenolysis,
c) providing at least one enzyme comprising a transglycosidase activity and/or a glycosynthase activity;
d) preparing a mixture of the donor(s), acceptor(s) and enzyme(s), provided in steps a), b) and c);
e) incubating the mixture prepared according to step d);
f) repeating at least one of the steps a) to c), then repeating step d) and step e) when only one HMO or derivative or precursor thereof is made as a result of step e) above;
g) optionally repeating at least one of the steps a) to c), then repeating step d) and step e), with the mixture obtained as a result of step e) or f);
h) optionally subjecting the mixture obtained as a result of step e), f) or g) to a hydrogenolysis reaction.

According to the preferred and the more preferred embodiments above, at least one more additional incubation cycle is needed when only one product (HMO or HMO derivative or HMO precursor) is formed after the first incubation cycle. Lactose is not herein considered to be an HMO. This case may occur in some donor-acceptor pairs provided in steps a) and b). This situation includes cases where starting materials, that is compounds provided in steps a) and b) of the method, remain in the reaction mixture after the incubation step along with a single product formed during the incubation step. When repeating at least one of the steps a) to c), then step d) and step e), the at least one compound provided according to step a) is preferably different from that/those provided in the first cycle; the at least one compound provided according to step b) is preferably different from that/those provided in the first cycle, and the at least one enzyme provided according to step c) is preferably different from that provided in the first cycle, but at least one of the steps a) to c) must be different from that carried out in the first cycle.

In the context of the present invention the term "group removable by hydrogenolysis" refers to groups whereby a carbon-heteroatom single bond is cleaved or undergoes "lysis" by hydrogen. The heteroatom may vary, but it usually is oxygen, nitrogen, or sulfur. Hydrogenolysis represents an exception among protecting group chemistries, in which water can be used as a solvent. Hydrogenolysis itself is a powerful deprotection process suitable to remove O-benzyl/substituted O-benzyl moieties from an oligosaccharide scaffold in almost a quantitative manner under extremely gentle conditions preventing by-product formations. It is also an advantage of hydrogenolysis as a final deblocking procedure within a complex synthetic pathway that only a catalytic amount of the reagents are required for the completion of the reaction, and that the reaction provides exclusively toluene or substituted toluene derivatives as by-products. Both toluene and substituted toluene derivatives can easily be removed even in multi ton scales from water soluble oligosaccharide products via evaporation and/or extraction processes. Suitable groups for hydrogenolysis may include benzyl, diphenylmethyl (benzhydryl), 1-naphthylmethyl, 2-naphthylmethyl or triphenylmethyl (trityl) groups, each of which may be optionally substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). A particularly preferred protecting group is benzyl optionally substituted with one or more groups selected from alkyl or halogen. More preferably, the protecting group is selected from unsubstituted benzyl, 4-chlorobenzyl and 4-methylbenzyl. These particularly preferred and more preferable protecting groups have the advantage that the by-products of the hydrogenolysis are exclusively toluene or substituted toluene. Such by-products can easily be removed even in multi ton scales from water soluble oligosaccharide products via evaporation and/or extraction processes. Hydrogenolysis may be carried out by adding catalytic amounts of palladium, Raney nickel or another appropriate metal catalyst known for use in hydrogenolysis, resulting in the regeneration of the OH group. Groups of this type are well known to the skilled man and thoroughly discussed (see e.g. P. G. M. Wuts and T. W. Greene: *Protective Groups in Organic Synthesis*, John Wiley & Sons (2007)).

Furthermore, the term "HMO precursor" means an R-glycoside of an HMO which has been modified with a residue R to form a glycoside via a glycosidic bond.

Furthermore, the term "HMO derivative" means an oligosaccharide structurally similar to a HMO and R-glycosides thereof, preferably derivatives according to general formula 1, 2, 3 and 4.

Additionally, the term "fucosyl" within the context of the present invention means a L-fucopyranosyl group attached to the core oligosaccharide with α-interglycosidic linkage:

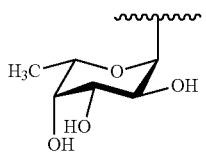

"N-acetyl-lactosaminyl" group within the context of the present invention means the glycosyl residue of N-acetyl-lactosamine (LacNAc, Galpβ1-4GlcNAcp) linked with β-linkage:

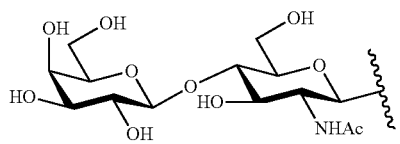

Furthermore, the term "lacto-N-biosyl" group within the context of the present invention means the glycosyl residue of lacto-N-biose (LNB, Galpβ1-3GlcNAcp) linked with β-linkage:

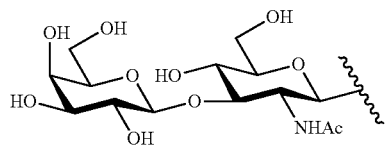

The term "sialyl" within the context of the present invention means the glycosyl residue of sialic acid (N-acetyl-neuraminic acid, Neu5Ac) linked with α-linkage:

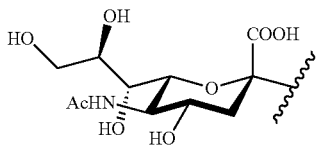

Additionally, the term "glycosyl residue comprising one or more N-acetyl-lactosaminyl and/or one or more lacto-N-biosyl units" within the context of the present invention means a linear or branched structure comprising the said units that are linked to each other by interglycosidic linkages.

The term "optionally substituted phenoxy" means a phenoxy group optionally substituted with 1 or 2 groups selected from nitro, halogen, alkyl, hydroxyalkyl, amino, formyl, carboxyl and alkoxycarbonyl, or two substituents in ortho position may form a methylenedioxy-group. Preferred substituents are nitro (preferably in 2- and/or 4-position), halogen (preferably fluoro and chloro). Especially preferred substituted phenoxy groups are selected from 4-nitrophenoxy, 2,4-dinitrophenoxy, 2-chloro-4-nitrophenoxy, 2-fluoro-4-nitrophenoxy, 3-fluoro-4-nitrophenoxy, 2-hydroxymethyl-4-nitrophenoxy, 3-hydroxymethyl-4-nitrophenoxy, 2-formyl-4-nitrophenoxy, 2-carboxy-4-nitrophenoxy, 2-methoxycarbonyl-4-nitrophenoxy, 5-fluoro-2-nitrophenoxy, 4-methoxycarbonyl-2-nitrophenoxy, 4-carboxy-2-nitrophenoxy, 2-aminophenoxy and 3,4-methylenedioxy-phenoxy.

The term "optionally substituted pyridinyloxy" means a pyridinyloxy, more preferably 2- or 4-pyridyloxy group, optionally substituted with 1 or 2 groups selected from nitro, halogen, alkyl and alkoxy. Especially referred pyridinyloxy groups are selected from 4-pyridinyloxy, 2-pyridinyloxy, 3-nitro-2-pyridinyloxy and 3-methoxy-2-pyridinyloxy.

According to step a) of the first aspect, including the preferred and more preferred embodiments, at least one universal donor is provided, and according to step b) of the first aspect, including the preferred and more preferred embodiments, at least one acceptor is provided. In the context of the present invention, the term "donor" is understood as a compound, which provides or transfers a specific moiety in a chemical reaction, e.g. a nucleophilic or electrophilic substitution reaction, to a further compound, preferably an acceptor. Particularly preferably, a "universal donor" is understood as a compound, which provides or transfers a specific moiety in a chemical reaction, e.g. a nucleophilic or electrophilic substitution reaction, to a further compound, preferably an acceptor, wherein the donor is not restricted to naturally occurring donors for the preparation of HMOs and may also lead to naturally occurring HMOs and/or to non-naturally occurring HMOs as a product. Such a universal donor is preferably as defined above. Likewise, the term "acceptor" is understood as a compound, which receives a specific moiety in a chemical reaction, e.g. nucleophilic or electrophilic substitution reaction, from a further compound, preferably a universal donor as defined herein. Such an acceptor is preferably as defined above.

Compounds for use as universal donors in step a) of the first aspect, including the preferred and more preferred embodiments, for the preparation of human milk oligosaccharides (HMOs), may preferably be selected from compounds according to formulae 5 to 8, wherein the substituents are preferably selected depending on the enzymes used during the method of the present invention. Preferably, the donors are selected depending on their a transglycosidase activity from compounds according to formulae 5 to 8, wherein X is optionally substituted 4-nitrophenoxy, group A, group B, group C, or from compounds 9 and 10. Likewise preferably, the donors are selected depending on their glycosynthase activity from compounds according to formulae 5 to 8, wherein X is azide or fluoro. Both selections may be carried out independently of each other or together.

Furthermore, compounds for use as universal donors in step a) of the first aspect, including the preferred and more preferred embodiments, for the preparation of human milk oligosaccharides (HMOs), may preferably be selected from compounds according to formulae 5 to 8, wherein X is 4-nitrophenoxy, 2,4-dinitrophenoxy, 2-chloro-4-nitrophenoxy, 2,5-dimethyl-3-oxo-(2H)-furan-4-yloxy, 2-ethyl-5-methyl-3-oxo-(2H)-furan-4-yloxy, 5-ethyl-2-methyl-3-oxo-(2H)-furan-4-yloxy, 4,6-dimethoxy-1,3,5-triazin-2-yloxy, 4,6-diethoxy-1,3,5-triazin-2-yloxy, 4-methylumbelliferyloxy.

In step c) of the method of the present invention for generating human milk oligosaccharides (HMOs) at least one enzyme comprising a transglycosidase activity and/or a glycosynthase activity is provided.

Enzymes suitable in step c) of the first aspect, including the preferred and more preferred embodiments, for the generation of human milk oligosaccharides (HMOs) typically comprise at least one enzyme comprising a transglycosidase activity and/or a glycosynthase activity, preferably selected from enzymes having, e.g. a fucosidase, trans-fucosidase or fucosynthase activity, a sialidase (neuraminidase) or transsialidase (transneuraminidase) activity, a lacto-N-biosidase or trans-lacto-N-biosidase activity and/or a N-acetyllactoaminidase or trans-N-acetyllactoaminidase activity, or any further enzyme having such an activity. Even more preferably, enzymes suitable in step d) of the first aspect, including the preferred and more preferred embodiments, for the generation of human milk oligosaccharides (HMOs) may be selected from the group comprising wild type or mutated glycosidases or transglycosidases, preferably wild type or mutated glycosidases or transglycosidases having a fucosidase, trans-fucosidase or fucosynthase activity, a sialidase (neuraminidase) or trans-sialidase (transneuraminidase) activity, a lacto-N-biosidase or trans-lacto-N-biosidase activity and/or a N-acetyllactoaminidase or trans-N-acetyllactoaminidase activity, or preferably having α-trans-fucosidase, α-trans-sialidase, β-trans-lacto-N-biosidase and/or β-trans-N-acetyllactosaminidase activity.

Enzymes suitable in step c) of the first aspect, including the preferred and more preferred embodiments, for the generation of human milk oligosaccharides (HMOs) furthermore may be selected from any genus known to a skilled person, to express or secrete at least one enzyme as defined above, e.g. an enzyme having a transglycosidase activity and/or a glycosynthase activity, preferably an enzyme having a fucosidase, trans-fucosidase or fucosynthase activity, a sialidase (neuraminidase) or trans-sialidase (transneuraminidase) activity, a lacto-N-biosidase or trans-lacto-N-biosidase activity and/or a N-acetyllactoaminidase or trans-N-acetyllactoaminidase activity, or preferably having α-trans-fucosidase, α-trans-sialidase, β-trans-lacto-N-biosidase and/or β-trans-N-acetyllactosaminidase activity, or any further enzyme having such an activity. Even more preferably, such enzymes suitable in step c) of the first aspect, including the preferred and more preferred embodiments, for the generation of human milk oligosaccharides (HMOs) may be selected from non-pathogenic bacteria selected from *Bacillus, Bifidobacterium, Lactobacillus, Leuconostoc, Lactococcus, Streptococcus, Streptomyces, Sulfolobus, Thermotoga*, or *Trypanosoma*.

Even more preferably, such enzymes suitable in step c) of the first aspect, including the preferred and more preferred embodiments, for the generation of human milk oligosaccharides (HMOs) are selected from the group comprising the non-pathogenic bacteria *Bacillus circulans*, lactic acid bacteria, such as *Bifidobacterium bifidum* JCM 1254, *Bifidobacterium bifidum* NCIMB 41171, *Bifidobacterium bifidum* NCIMB 41171, *Bifidobacterium bifidum* JCM1254, *Bifidobacterium bifidum* JCM1254, *Bifidobacterium bifidum* PRL2010, *Bifidobacterium bifidum* PRL2010, *Bifidobacterium bifidum* S17, *Bifidobacterium bifidum* S17, *Bifidobacterium dentium* Bd1, *Bifidobacterium longum* subsp. *infantis* ATCC 15697, *Bifidobacterium longum* subsp *longum* JDM 301, *Bifidobacterium longum* subsp. *infantis* JCM 1222, *Lactobacillus casei* BL23, *Streptomyces* sp., *Sulfolobus solfataricus* P2, *Thermotoga maritima* MSB8, and *Trypanosoma cruzi*.

Particularly preferred microorganisms in the above context, particularly for targeted glycosidases/transglycosidases/glycosynthases, comprise lactic acid bacteria. Lactic acid bacteria, and more particularly non-pathogenic bacteria from the genus *Bifidobacterium* contain a series of glycosidases including α-2,3/6 sialidases (GH33), α-1,2/3/4 fucosidases (GH29 and GH95), lacto-N-biosidases (GH20), β-galactosidases (GH2) and β-N-acetylhexosaminidases (GH20) that are able to recognize human milk oligosaccharides. Depending on the bifidobacteria strains, these glycosidases are intra- or extracellular enzymes.

A further aspect regarding the use of glycosidases and/or glycosynthases from lactic acid bacteria concerns the industrial importance of such bacteria since they have the GRAS (generally recognized as safe) status. According to another more preferred aspect the glycosidase and/or glycosynthases displaying a trans-fucosidase, trans-sialidase, trans-lacto-N-biosidase and/or trans-N-acetyllactosaminidase activity, preferably a α-trans-fucosidase, α-trans-sialidase, β-trans-lacto-N-biosidase and/or β-trans-N-acetyllactosaminidase activity, is a wild type or an engineered glycosidase, most preferably the wild type glycosidase is taken from the group consisting of lactic acid bacteria, wherein the glycosidase is converted to a transglycosidase by rational engineering or/and directed evolution. A glycosidase and/or glycosynthase selected from the group consisting of lactic acid bacteria is most preferably a glycosidase from *Bifidobacterium, Lactobacillus, Lactococcus, Streptococcus* or *Leuconostoc*. A glycosidase selected from the genus *Bifidobacterium* is most preferably a glycosidase from *Bifidobacterium longum* subsp. *Infantis, Bifidobacterium longum* subsp. *Longum, Bifidobacterium breve, Bifidobacterium bifidum* and *Bifidobacterium catenulatum*.

Furthermore, engineered fucosidases from thermophilic organisms such as *Sulfolobus solfataricus* and *Thermotoga maritima* have recently been developed, which may be used in the method of the present invention. These thermostable glycosidases have considerable potential for industrial applications since they can be used in biotechnological processes at elevated temperatures, and so facilitating the process, preventing risk of contamination, and increasing the solubility of the compounds used in the reaction.

According to another more preferred embodiment, the glycosidase and/or glycosynthase enzyme displaying a trans-fucosidase, trans-sialidase, trans-lacto-N-biosidase and/or trans-N-acetyllactosaminidase activity, preferably an α-trans-fucosidase, α-trans-sialidase, β-trans-lacto-N-biosidase and/or β-trans-N-acetyllactosaminidase activity, is a wild type or an engineered glycosidase. Most preferably, the wild type glycosidase is taken from the group consisting of thermophilic organisms, which glycosidase is converted to a transglycosidase by rational engineering or/and directed evolution. An α-L-fucosidase selected from thermophilic organisms is most preferably an α-L-fucosidase from *Thermotoga maritima* and *Sulfolobus solfataricus*.

Preferably, the at least one enzyme comprising a transglycosidase activity and/or a glycosynthase activity may be selected from an enzyme exhibiting a fucosidase, trans-fucosidase or fucosynthase activity, preferably as described in the following. In this context, enzymes having a fucosidase, trans-fucosidase or fucosynthase activity, more preferably an α-trans-fucosidase activity, are preferably selected from fucosidases in general, and more preferably from α-L-fucosidases, e.g. α-L-fucosidases as classified according to EC 3.2.1.38 and 3.2.1.51. α-L-Fucosidases are widely spread in living organisms such as mammals, plants, fungi and bacteria. These enzymes belong to the families 29 and 95 of the glycoside hydrolases (GH29 and GH95) as defined by the CAZY nomenclature (http://www.cazy.org). Fucosidases from GH 29 are retaining enzymes (3D structure: $(\beta/\alpha)_8$) whereas fucosidases from GH 95 are inverting enzymes (3D structure: $(\alpha/\alpha)_6$). The substrate specificity of the GH29 family is broad whereas that of the GH95 family is strict to α1,2-linked fucosyl residues. The GH29 family seems to be divided into two subfamilies. One subfamily typically has strict specificity towards α1,3- and α1,4-fucosidic linkages. The members of a further subfamily have broader specificity, covering all α-fucosyl linkages. α-L-fucosidases generally hydrolyse the terminal fucosyl residue from glycans. These enzymes are also capable of acting as catalysts for fucosylation reactions due to their transfucosylation activity and thus may be used in the context of the method of the present invention, preferably under kinetically controlled conditions.

Fucosidases, which may be employed in the context of the present invention, may also comprise engineered fucosidases. Such engineered fucosidases preferably comprise engineered α-L-fucosidases, preferably engineered fucosidases derived from fucosidases as described above, e.g. an engineered α-1,2-L-fucosynthase from *Bifidobacterium bifidum*, α-L-fucosynthases from *Sulfolobus solfataricus* and *Thermotoga maritime*, etc. Such engineered fucosidases show an acceptor dependent regioselectivity and are devoid of product hydrolysis activity. Furthermore, engineered fucosidases preferably comprise α-L-fucosidase from *Thermotoga maritima*, which has also been recently converted into an efficient α-L-trans-fucosidase by directed evolution (see Osanjo, G., et al., *Directed evolution of the alpha-L-fucosidase from Thermotoga maritima into an alpha-L-trans-fucosidase*. Biochemistry, 2007, 46(4): p. 1022-33).

Even more preferably, the at least one enzyme having a fucosidase and/or trans-fucosidase and/or fucosynthase activity may be selected from α-L-fucosidases derived from *Thermotoga maritima* MSB8, *Sulfolobus solfataricus* P2, *Bifidobacterium bifidum* JCM 1254, *Bifidobacterium bifidum* JCM 1254, *Bifidobacterium longum* subsp. *infantis* ATCC 15697, *Bifidobacterium longum* subsp. *infantis* ATCC 15697, *Bifidobacterium longum* subsp. *Infantis* JCM 1222, *Bifidobacterium bifidum* PRL2010, *Bifidobacterium bifidum* S17, *Bifidobacterium longum* subsp *longum* JDM 301, *Bifidobacterium dentium* Bd1, or *Lactobacillus casei* BL23, etc.

Even more preferably the at least one enzyme having a fucosidase and/or trans-fucosidase and/or fucosynthase activity may be selected from following α-L-fucosidases as defined according to the following deposit numbers gi|4980806 (*Thermotoga maritima* MSB8, SEQ ID NO: 1), gi|13816464 (*Sulfolobus solfataricus* P2, SEQ ID NO: 2), gi|34451973 (*Bifidobacterium bifidum* JCM 1254, SEQ ID NO: 3), gi|242345155 (*Bifidobacterium bifidum*, JCM 1254, SEQ ID NO: 4), gi|213524647 (*Bifidobacterium longum* subsp. *infantis*, ATCC 15697, SEQ ID NO: 5), gi|213522629 (*Bifidobacterium longum* subsp. *infantis* ATCC 15697), gi|213522799 (*Bifidobacterium longum* subsp. *infantis* ATCC 15697), gi|213524646 (*Bifidobacterium longum* subsp. *infantis* ATCC 15697), gi|320457227 (*Bifidobacterium longum* subsp. *infantis* JCM 1222), gi|320457408 (*Bifidobacterium longum* subsp. *infantis* JCM 1222), gi|320459369 (*Bifidobacterium longum* subsp. *infantis* JCM 1222), gi|320459368 (*Bifidobacterium longum* subsp. *infantis* JCM 1222), gi|310867039 (*Bifidobacterium bifidum* PRL2010), gi|310865953 (*Bifidobacterium bifidum* PRL2010), gi|309250672 (*Bifidobacterium bifidum* S17), gi|309251774 (*Bifidobacterium bifidum* S17), gi|296182927 (*Bifidobacterium longum* subsp *longum* JDM 301), gi|296182928 (*Bifidobacterium longum* subsp *longum* JDM 301), gi|283103603 (*Bifidobacterium dentium* Bd1), gi|190713109 (*Lactobacillus casei* BL23, SEQ ID NO: 6), gi|190713871 (*Lactobacillus casei* BL23, SEQ ID NO: 7), gi|190713978 (*Lactobacillus casei* BL23, SEQ ID NO: 8), etc., or a sequence exhibiting a sequence identity with one of the above mentioned enzyme sequences having a fucosidase and/or trans-fucosidase activity of at least 70%, more preferably at least 80%, equally more preferably at least 85%, even more preferably at least 90% and most preferably at least 95% or even 97%, 98% or 99% as compared to the entire wild type sequence on amino acid level.

Particularly preferred α-L-fucosidases with fucosidase/trans-fucosidase/fucosynthase activity are listed in the following Table 2:

TABLE 2

Preferred α-L-fucosidases

| GI number in GenBank Database | Organisms | SEQ ID NO: |
| --- | --- | --- |
| gi|4980806 | *Thermotoga maritima* MSB8 | 1 |
| gi|13816464 | *Sulfolobus solfataricus* P2 | 2 |
| gi|34451973 | *Bifidobacterium bifidum* JCM 1254 | 3 |
| gi|242345155 | *Bifidobacterium bifidum* JCM 1254 | 4 |
| gi|213524647 | *Bifidobacterium longum* subsp. *infantis* ATCC 15697 | 5 |
| gi|213522629 | *Bifidobacterium longum* subsp. *infantis* ATCC 15697 | — |
| gi|213522799 | *Bifidobacterium longum* subsp. *infantis* ATCC 15697 | — |
| gi|213524646 | *Bifidobacterium longum* subsp. *Infantis* ATCC 15697 | — |
| gi|320457227 | *Bifidobacterium longum* subsp. *infantis* JCM 1222 | — |
| gi|320457408 | *Bifidobacterium longum* subsp. *infantis* JCM 1222 | — |
| gi|320459369 | *Bifidobacterium longum* subsp. *infantis* JCM 1222 | — |
| gi|320459368 | *Bifidobacterium longum* subsp. *infantis* JCM 1222 | — |
| gi|310867039 | *Bifidobacterium bifidum* PRL2010 | — |
| gi|310865953 | *Bifidobacterium bifidum* PRL2010 | — |
| gi|309250672 | *Bifidobacterium bifidum* S17 | — |
| gi|309251774 | *Bifidobacterium bifidum* S17 | — |
| gi|296182927 | *Bifidobacterium longum* subsp *longum* JDM 301 | — |
| gi|296182928 | *Bifidobacterium longum* subsp *longum* JDM 301 | — |
| gi|283103603 | *Bifidobacterium dentium* Bd1 | — |
| gi|190713109 | *Lactobacillus casei* BL23 | 6 |
| gi|190713871 | *Lactobacillus casei* BL23 | 7 |
| gi|190713978 | *Lactobacillus casei* BL23 | 8 |

Likewise preferably, the at least one enzyme comprising a transglycosidase activity and/or a glycosynthase activity may be selected from an enzyme exhibiting a sialidase or trans-sialidase activity, preferably as described in the following. In this context, enzymes having a sialidase or trans-sialidase activity are preferably selected from a sialidase or trans-sialidase as described in the following, e.g. sialidases (EC 3.2.1.18) and trans-sialidases (EC 2.4.1.-) as classified according to the GH33 family. They are retaining enzymes. Sialidases and trans-sialidases are widely distributed in nature. They are found particularly in diverse virus families and bacteria, and also in protozoa, some invertebrates and mammals. These enzymes differ in their biochemical properties, e.g., kinetics, binding affinity or substrate preference. Nevertheless, they possess conserved domains and structural similarities. Trans-sialidases differ from sialidases since they can transfer sialic acids, preferably α-2,3-bonded sialic acids, from a donor molecule to an acceptor derivative, which is preferably a terminal galactose moiety with a β-interglycosidic linkage. As a result of this transfer, an α-glycosidic bond is be formed between the sialic acid and the acceptor. However, if there is no suitable acceptor, the trans-sialidase hydrolyses the sialic acid.

The first trans-sialidase enzyme described was found in *Trypanosoma cruzi*, a protozoa which causes Chagas disease. This trans-sialidase (TcTS) has been extensively studied. Since that time trans-sialidases have been detected in several other trypanosome types such as *Trypanosoma brucei gambiense*, *Trypanosoma brucei rhodesiense*, *Trypanosoma brucei brucei* and *Trypanosoma congolense*. Moreover, the existence of trans-sialidases has been shown in *Endotrypanum* types, in *Corynebacterium diphtheriae* and even in human plasma.

Sialidases can be classified into two different subgroups, endo- and exo-sialidases. The endo-sialidases hydrolyze sialic acid linkages internal to macromolecules, while the exo-sialidases attack terminal sialic acid linkages, and desialylate glycoproteins, glycopeptides, gangliosides, oligosaccharides and polysaccharides. Recently, sialidases from *Bifidobacterium bifidum* and *Bifidobacterium longum* subsp. *infantis* have been identified, cloned and characterized. These sialidases can cleave and so recognize both α-2,3- and α-2,6-linked sialosides. Sialidases from *Bifidobacterium longum* subsp. *infantis* have a consistent preference for α-2,6-linkage whereas sialidases from *Bifidobacterium bifidum* have a consistent preference for α-2,3-linkage. These enzymes are also capable of acting as catalysts for sialylation reactions due to their trans-sialidase activity and thus may be used in the context of the method of the present invention, preferably under kinetically controlled conditions.

Sialidases, which may be employed in the context of the present invention, may also comprise engineered sialidases. Based on sequence and structure comparisons, sialidase from *Trypanosoma rangeli* may be mutated at six positions, wherein the resulting mutant is able to display a significant level of trans-sialidase activity (see Paris, G., et al., *A sialidase mutant displaying trans-sialidase activity*. J Mol Biol, 2005. 345(4): p. 923-34).

Even more preferably, the at least one enzyme having a sialidase and/or trans-sialidase activity may be selected from sialidases or trans-sialidases derived from *Bifidobacterium longum* subsp. *infantis* ATCC 15697, *Bifidobacterium bifidum* JCM1254, *Bifidobacterium bifidum* S17, *Bifidobacterium bifidum* PRL2010, *Bifidobacterium bifidum* NCIMB 41171, *Trypanosoma cruzi*, etc.

Even more preferably the at least one enzyme having a sialidase and/or trans-sialidase activity may be selected from sialidases or trans-sialidases as defined according to the following deposit numbers: gi|213524659 (*Bifidobacterium longum* subsp. *infantis* ATCC 15697, SEQ ID NO: 9), gi|213523006 *Bifidobacterium longum* subsp. *infantis* ATCC 15697, SEQ ID NO: 10), siab2 (*Bifidobacterium bifidum* JCM1254), further sialidases or trans-sialidases from *Bifidobacterium bifidum* JCM1254), gi|309252191 (*Bifidobacterium bifidum* S17, SEQ ID NO: 11), gi|309252190 (*Bifidobacterium bifidum* S17, SEQ ID NO: 12), gi|310867437 (*Bifidobacterium bifidum* PRL2010, SEQ ID NO: 13), gi|310867438 (*Bifidobacterium bifidum* PRL2010, SEQ ID NO: 14), gi|224283484 (*Bifidobacterium bifidum* NCIMB 41171), gi|313140638 (*Bifidobacterium bifidum* NCIMB 41171), gi|47252690 (*Trypanosoma cruzi*, SEQ ID NO: 15), gi|432485 (*Trypanosoma cruzi*, SEQ ID NO: 16), gi|343957998 (*Trypanosoma congolense*, SEQ ID NO:20), gi|343958004 (*Trypanosoma congolense*, SEQ ID NO:21) etc., or a sequence exhibiting a sequence identity with one of the above mentioned enzyme sequences having a sialidase and/or trans-sialidase activity of at least 70%, more preferably at least 80%, equally more preferably at least 85%, even more preferably at least 90% and most preferably at least 95% or even 97%, 98% or 99% as compared to the entire wild type sequence on amino acid level.

Particularly preferred sialidases with sialidase/trans-sialidase activity are listed in the following Table 3:

TABLE 3

Preferred sialidases/trans-sialidases

| GI number in GenBank Database | Organisms | SEQ ID NO: |
|---|---|---|
| gi|213524659 | *Bifidobacterium longum* subsp. *infantis* ATCC 15697 | 9 |
| gi|213523006 | *Bifidobacterium longum* subsp. *infantis* ATCC 15697 | 10 |
| gi|309252191 | *Bifidobacterium bifidum* S17 | 11 |
| gi|309252190 | *Bifidobacterium bifidum* S17 | 12 |
| gi|310867437 | *Bifidobacterium bifidum* PRL2010 | 13 |
| gi|310867438 | *Bifidobacterium bifidum* PRL2010 | 14 |
| gi|224283484 | *Bifidobacterium bifidum* NCIMB 41171 | — |
| gi|313140638 | *Bifidobacterium bifidum* NCIMB 41171 | — |
| gi|47252690 | *Trypanosoma cruzi* | 15 |
| gi|432485 | *Trypanosoma cruzi* | 16 |
| gi|343957998 | *Trypanosoma congolense* | 20 |
| gi|343958004 | *Trypanosoma congolense* | 21 |

Additionally, the at least one enzyme comprising a transglycosidase activity and/or a glycosynthase activity may be preferably selected from an enzyme exhibiting a lacto-N-biosidase or trans-lacto-N-biosidase activity, preferably as described in the following. In this context, enzymes having a lacto-N-biosidase or trans-lacto-N-biosidase activity are preferably selected from a lacto-N-biosidase or trans-lacto-N-biosidase as described in the following, e.g. lacto-N-biosidases (EC 3.2.1.140) as classified according to the GH20 family. Lacto-N-biosidases typically proceed through a retaining mechanism. Only two lacto-N-biosidases from *Streptomyces* and *Bifidobacterium bifidum* have been described and characterized up to now, which may be utilized in the present invention as a lacto-N-biosidase or trans-lacto-N-biosidase (see Sano, M., K. Hayakawa, and I. Kato, Proc Natl Acad Sci USA, 1992. 89(18): p. 8512-6; Sano, M., K. Hayakawa, and I. Kato, J Biol Chem, 1993. 268(25): p. 18560-6; Wada, J., et al., Appl Environ Microbiol, 2008. 74(13): p. 3996-4004.). Lacto-N-biosidases specifically hydrolyse the terminal lacto-N-biosyl residue (β-D-Gal-(1→3)-D-GlcNAc) from the non-reducing end of oligosaccharides with the structure β-D-Gal-(1→3)-β-D-GlcNAc-(1→3)-β-D-Gal-(1→R). Wada et al. (supra) and Murata et al. (*Glycoconj. J.* 16, 189 (1999)) also demonstrated the ability of the lacto-N-biosidase from *Bifidobacterium bifidum* and *Aureobacterium* sp. L-101, respectively, to catalyze the transglycosylation by incubating donor substrates (such as lacto-N-tetraose and pNP-β-LNB) with acceptors (such as various 1-alkanols and lactose).

Even more preferably, the at least one enzyme having a lacto-N-biosidase or trans-lacto-N-biosidase activity may be selected from lacto-N-biosidases or trans-lacto-N-biosidases derived from *Bifidobacterium bifidum* JCM1254, *Bifidobacterium bifidum* PRL2010, *Bifidobacterium bifidum* NCIMB 41171, *Aureobacterium* sp. L-101 or *Streptomyces* sp., etc.

Even more preferably the at least one enzyme having a lacto-N-biosidase or trans-lacto-N-biosidase activity may be selected from lacto-N-biosidases or trans-lacto-N-biosidases as defined according to the following deposit numbers: gi|167369738 (*Bifidobacterium bifidum* JCM1254, SEQ ID NO: 17), gi|4096812 (*Streptomyces* sp., SEQ ID NO: 18), gi|310867103 (*Bifidobacterium bifidum* PRL2010), gi|313140985 (*Bifidobacterium bifidum* NCIMB 41171), etc., or a sequence exhibiting a sequence identity with one of the above mentioned enzyme sequences having a lacto-N-biosidase or trans-lacto-N-biosidase activity of at least 70%, more preferably at least 80%, equally more preferably at least 85%, even more preferably at least 90% and most preferably at least 95% or even 97%, 98% or 99% as compared to the entire wild type sequence on amino acid level.

Particularly preferred lacto-N-biosidases with lacto-N-biosidase or trans-lacto-N-biosidase activity are listed in the following Table 4:

TABLE 4

Preferred lacto-N-biosidases or trans-lacto-N-biosidases

| GI number in GenBank Database | Organisms | SEQ ID NO: |
|---|---|---|
| gi\|167369738 | *Bifidobacterium bifidum* JCM1254 | 17 |
| gi\|4096812 | *Streptomyces* sp. | 18 |
| gi\|310867103 | *Bifidobacterium bifidum* PRL2010 | — |
| gi\|313140985 | *Bifidobacterium bifidum* NCIMB 41171 | — |

Furthermore, the at least one enzyme comprising a transglycosidase activity and/or a glycosynthase activity may be preferably selected from an enzyme exhibiting a N-acetyllactosaminidase or trans-N-acetyllactosaminidase activity, preferably as described in the following. In this context, enzymes having a N-acetyllactosaminidase or trans-N-acetyllactosaminidase activity are preferably selected from a N-acetyllactosaminidase or trans-N-acetyllactosaminidase as described in the following, e.g. lacto-N-biosidases (EC 3.2.1.140) as classified according to the GH20 family. Particularly preferably, chitinase from *bacillus circulans*, more preferably chitinase A1 from *Bacillus Circulans* WL-12 as deposited under gi\|142688 (SEQ ID NO: 19), may be used as a N-acetyllactosaminidase or trans-N-acetyllactosaminidase, or a sequence exhibiting a sequence identity with one of the above mentioned enzyme sequences having a N-acetyllactosaminidase or trans-N-acetyllactosaminidase activity of at least 70%, more preferably at least 80%, equally more preferably at least 85%, even more preferably at least 90% and most preferably at least 95% or even 97%, 98% or 99% as compared to the entire wild type sequence on amino acid level. Notably, Shoda et al. showed that chitinase A1 from *B. Circulans* WL-12 is able to transfer N-acetyllactosamine with a β-1,6 glycosidic linkage using a 1,2-oxazoline derivative of N-acetyllactosamine (see Shoda, S.-i., et al., Cellulose, 2006. 13(4): p. 477-484.).

Particularly preferred N-acetyllactosaminidases or trans-N-acetyllactosaminidases are listed in the following Table 5:

TABLE 5

Preferred N-acetyllactosaminidases or trans-N-acetyllactosaminidases

| GI number in the GenBank Database | Organisms | SEQ ID NO: |
|---|---|---|
| gi\|142688 | *Bacillus circulans* | 19 |

As defined above, proteins comprising a transglycosidase and/or a glycosynthase activity as defined above may also comprise engineered proteins comprising a transglycosidase and/or a glycosynthase activity. It is particularly envisaged that wild type or mutated glycosidases displaying a transfucosidase, transsialidase, trans-lacto-N-biosidase and/or trans-N-acetyllactosaminidase activity, preferably a α-transfucosidase, α-transsialidase, β-trans-lacto-N-biosidase and/or β-trans-N-acetyllactosaminidase activity, can be used in the present invention to produce such oligosaccharides. Preparation of such enzymes is preferably carried out via site directed mutagenesis approaches or directed evolution.

In rational engineering novel altered enzymes (mutants) are created via site directed mutagenesis approaches, preferably by introduction of point mutations. This technique generally requires reliance on the static 3D protein structure. The mutations generally affect the active site of the enzymes such that they lose their ability to degrade their transglycosylation products but remain capable of synthesis. A preferred strategy consists of the replacement of the catalytic nucleophile by a non-nucleophilic residue. This modification results in the formation of an inactive mutant or an altered enzyme with reduced transglycosylation activity due the lack of appropriate environment for the formation of the reactive host-guest complex for transglycosylation. However, in the presence of a more active glycosyl donor (e.g. glycosyl fluoride) that mimics the glycosyl enzyme intermediate, the mutated enzyme is able to transfer efficiently the glycosyl moiety to a suitable acceptor generating a glycoside with inverted anomeric stereochemistry. Such a mutant glycosidase is termed a glycosynthase and their development represents one of the major advances in the use of glycosidases for synthetic purposes. In principle, the glycosynthase concept can be applied to all GH specificities and offer a large panel of enzymes potentially able to synthesize various oligosaccharides with very high yields, up to 95%.

The second preferred technique is called directed evolution. This strategy comprises random mutagenesis applied to the gene of the selected glycosidase and generates thus a library of genetically diverse genes expressing glycosidase. Generation of sequence diversity can be performed using well-known methodologies, the most preferable being the error prone polymerase chain reaction (epCR) method. This gene library may be inserted into suitable microorganisms such as *E. coli* or *S. cerevisiae* for producing recombinant variants with slightly altered properties. Clones expressing improved enzymes are then identified with a fast and reliable screening method, selected and brought into a next round of mutation process. The recursive cycles of mutation, recombination and selection are continued as far as mutant(s) with the desired activity and/or specificity is/are evolved. To date, different high-throughput screening methodologies for glycosidases including glycosynthases have been developed. Applying these approaches, effective engineered transglycosidases, including new and more efficient glycosynthases can and have been created and isolated. An α-L-fucosidase from *Thermotoga maritima* has been recently converted into an efficient α-L-transfucosidase by directed evolution. The transferase/hydrolysis ratio of the evolved enzyme was 30 times higher than the native enzyme (see Osanjo, G., et al., Biochemistry, 2007. 46(4): p. 1022-33).

Proteins comprising a transglycosidase and/or a glycosynthase activity as defined above may also comprise fragments or variants of those protein sequences. Such fragments or variants may typically comprise a sequence having a sequence identity with one of the above mentioned proteins sequences of at least 70%, more preferably at least 80%, equally more preferably at least 85%, even more preferably at least 90% and most preferably at least 95% or even 97%, 98% or 99% as compared to the entire wild type sequence on amino acid level.

"Fragments" of proteins or peptides in the context of the present invention may also comprise a sequence of a protein or peptide as defined herein, which is, with regard to its amino acid sequence N-terminally, C-terminally and/or intrasequentially truncated compared to the amino acid sequence of the original (native) protein. Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5'-, 3'- and/or intrasequentially truncated compared to the nucleic acid molecule of the original (native) nucleic acid molecule. A sequence identity with respect to such a fragment as defined herein may therefore preferably refer to the entire nucleic acid as defined herein.

"Variants" of proteins or peptides as defined in the context of the present invention (e.g. as encoded by a nucleic acid as defined herein) may be encoded by the nucleic acid molecule of apolymeric carrier cargo complex. Thereby, a protein or peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property.

"Variants" of proteins or peptides as defined in the context of the present invention (e.g. as encoded by a nucleic acid as defined herein) may also comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The proteins as added in step c) of the first aspect, including the preferred and more preferred embodiments, may be provided in a free form or alternatively be bound to or are immobilized onto a surface. In this specific case, the order of steps a), b) and c) is preferably inverted. Binding to or immobilization onto a surface may be carried out e.g. via electrostatic bonds, van der Waals-bonds, covalent bonds, etc. Binding to or immobilization onto a surface may be furthermore carried out, using a covalent linker or a crosslinker, or a Tag, as known to a skilled person for purification of proteins. Such tags comprise, inter alia, e.g. affinity tags or chromatography tags. Affinity tags may include e.g. chitin binding protein (CBP), maltose binding protein (MBP), glutathione-S-transferase (GST), or the Strep-Tag. The poly(His) tag is a widely-used protein tag, that binds to metal matrices. Chromatography tags are used to alter chromatographic properties of the protein to afford different resolution across a particular separation technique, and include e.g. polyanionic amino acids based tags, such as the FLAG-tag. The surface may be the surface of a bioreactor, or any suitable reaction chamber.

According to step d) a mixture is prepared from substances provided by steps a), b) and c). Preferably, such a mixture according to step d) represents a mixture of one, two, three, four, five, one to five, three to ten, five to ten or even more different donors as defined according to step a), one, two, three, four, five, one to five, three to ten, five to ten or even more different acceptors as defined according to step b), and one, two, three, four, five, two to five, two to ten, two to twenty, five to ten or even more different enzymes comprising transglycosidase activity and/or glycosynthase activity.

In a further step e) of the first aspect, including the preferred and more preferred embodiments, for the generation of human milk oligosaccharides (HMOs), the mixture containing at least one compound as defined according to step a), at least one compound as defined according to step b), and at least one enzyme as added according to step c), together forming a mixture according to step d), are incubated to allow generation of human milk oligosaccharides (HMOs) or derivatives thereof via enzymatic means using the at least one enzyme comprising a transglycosidase activity and/or a glycosynthase activity as defined herein. Such an incubation advantageously allows the generation of a multiplicity of different HMOs. Generation of such a multiplicity of different HMOs is based on the use of enzymes with different activities provided in step c), but also on the use of diverse universal donors and acceptors according to steps a) and b), preferably as a mixture as already outlined in step d). Utilizing this approach, the method of the present invention advantageously allows variation of the possible number and type of oligosaccharides obtainable by the method in a simple and cost efficient manner. The use of enzymes furthermore allows the preparation of various HMOs to be carried out in a stereoselective manner. Generation of HMOs preferably occurs by transferring glycosyl moieties (eg, a sialyl moiety, fucosyl moiety, N-acetyllactosaminyl moiety, or lacto-N-biosyl moiety) by forming new bonds at desired positions of the molecule, etc., in a well defined manner to obtain a mixture of various human milk oligosaccharides or derivatives thereof.

Incubation according to step e) of the first aspest, including the preferred and more preferred embodiments, preferably occurs with a concentration of (each of the) enzymes in a concentration of 1 mU/l to 1,000 U/l, preferably 10 mU/l to 100 U/l, when the activity capable of forming 1 µmol of specific product for a defined protein starting from a defined educt is defined as 1 unit (U), e.g. for a glycotransferase the production of a glycose-containing complex carbohydrate at 37° C. in 1 minute. The activity of each enzyme as defined herein may be assessed with respect to its naturally occurring or engineered substrate.

The incubation according to step e) of the first aspect, including the preferred and more preferred embodiments, may be carried out in a reaction medium, preferably an aqueous medium, comprising the mixture obtained according to step d) of the method of the present invention and optionally water; a buffer such as a phosphate buffer, a carbonate buffer, an acetate buffer, a borate buffer, a citrate buffer and a tris buffer, or combinations thereof; alcohol, such as methanol and ethanol; ester such as ethyl acetate; ketone such as acetone; amide such as acetamide; and the like.

Furthermore, the incubation according to step e) of the first aspect, including the preferred and more preferred embodiments, may be carried out in a reaction medium as defined above, wherein optionally a surfactant or an organic solvent may be added, if necessary. Any surfactant capable of accelerating the formation of a complex carbohydrate as defined according to the present invention as a possible product of the invention can be used as the surfactant. Examples include nonionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant may be used generally in a concentration of 0.1 to 50 g/l. The organic solvent may include xylene, toluene, fatty acid alcohol, acetone, ethyl acetate, and the like, which may be used in a concentration of generally 0.1 to 50 ml/l.

The incubation according to step e) of the first aspect, including the preferred and more preferred embodiments, may be furthermore carried out in a reaction medium as defined above, preferably having a pH 3 to 10, pH 5 to 10, preferably pH 6 to 8.

The incubation according to step e) of the first aspect, including the preferred and more preferred embodiments, may be furthermore carried out at a temperature of about 0° C. to about 100° C., preferably at a temperature of about 10 to about 50° C., e.g. at a temperature of about 20° C. to about 50° C. In the reaction medium, inorganic salts, such as $MnCl_2$ and $MgCl_2$, may be added, if necessary.

The incubation according to step e) of the method of the present invention may be carried out in a bioreactor. The bioreactor is preferably suitable for either a continuous mode or a discontinuous mode.

The incubation according to step e) of the first aspect, including the preferred and more preferred embodiments, may be carried out in a continuous or discontinuous mode. If carried out in a continuous mode, the method preferably provides for a continuous flow of compounds and/or enzymes as necessary, preferably by continuously providing educts of the reaction to the reaction mixture and continuously removing products from the reaction mixture, while maintaining the concentration of all components, including enzymes at a predetermined level. The enzymes used in a continuous mode may be added either in free form or as bound or immobilized to a surface.

With regard to the first aspect of the present invention, the addition of donors and/or acceptors and/or enzymes may be repeated according to an optional step f). Particularly preferably, any of steps a) to d) may be repeated, preferably with the mixture obtained according to step e). Such a mixture is preferably a mixture of at least one compound as defined herein for step a) and at least one compound as defined herein for step b) and at least one enzyme as defined herein according to step c). Such a stepwise proceeding may allow within multiple rounds the rational generation of a defined set of compounds in a controllable manner. It may also provide for a rational exclusion of specific components. To obtain such a variety of compounds, the compounds and/or enzymes may be added simultaneously or sequentially, more preferably compounds and/or enzymes may be added simultaneously in one step and/or sequentially in different steps.

Alternatively, a mixture with at least one compound as defined herein for step a) and at least one compound as defined herein for step b) and at least one enzyme as defined herein according to step c) may be incubated in one step without repetition of one or more steps. Such a proceeding may be preferable in certain circumstances, as it may lead to the largest variety of possible products.

With regard to the preferred and the more preferred embodiments of the first aspect, at least one more additional incubation cycle f) is needed when only one HMO or HMO derivative or precursor thereof is made after step e), as specified above. Particularly preferably, at least one of steps a) to c) shall be repeated, preferably with the mixture obtained according to step e). When repeating any of the steps a) to c), the at least one compound added according to step a) is preferably different to that/those provided in the first cycle, the at least one compound added according to step b) is preferably different to that/those provided in the first cycle, and the at least one enzyme added according to step c) is preferably different to that provided in the first cycle.

A person skilled in the art is able to explore and decide whether only one HMO or HMO derivative or precursor thereof is made after the first incubation step and whether at least one more incubation cycle is needed to achieve the goal. In a possible case, the selection of a particular donor, a particular acceptor and a particular enzyme leads to only one product, for example incubation of the system containing a sialic acid donor according to formula 6 (e.g. pNP sialic acid), an acceptor such as lactose or benzyl lactoside, and a 2-3-α-selective trans-sialidase enzyme results with high probability in the formation of one product, namely 3-sialyllactose (from lactose) or 3-sialyllactose benzyl glycoside (from benzyl lactoside). When more than one donor and/or more than one acceptor and/or more than enzyme are used for generating an HMO, HMO derivative or HMO precursor in one incubation cycle, more than one product is expected to be formed. Similarly, when the glycosidase and/or glycosynthase enzyme used has lesser (regio)selectivity, more than one product can be expected, even if only one acceptor is provided, as the enzyme is able to transfer the glycosyl moiety to various parts of the acceptor. Moreover, according to a general rule the proportion of the donor and acceptor can have a huge impact on the product diversity: the higher the donor-acceptor ratio, the higher the chance of obtaining more than one product in a one donor-one acceptor system. The skilled person has the repertoire of detection and monitoring methods, both qualitative and quantitative (e.g. TLC, HPLC, GC, GC-MS, electrophoresis, etc.) to find out whether one or more products have been formed.

Furthermore, with regard to the preferred and the more preferred embodiment of the first aspect, the addition acceptors and/or donors and/or enzymes may be repeated according to an optional step g). Such a mixture is preferably a mixture of at least one compound as defined herein for step a), at least one compound as defined herein for step b) and at least one enzyme as defined herein according to step c). When repeating at least one of the steps a) to c), then step d) and step e), the at least one compound provided according to step a) is preferably different from that/those provided in the previous cycle; the at least one compound provided according to step b) is preferably different from that/those provided in the previous cycle, and the at least one enzyme provided according to step c) is preferably different from that/those provided in the previous cycle, Such a stepwise proceeding may allow within multiple rounds the rational generation of a defined set of compounds in a controllable manner. It may also provide for a rational exclusion of specific components. To obtain such a variety of compounds, the compounds and/or enzymes may be added simultaneously or sequentially, and preferably compounds and/or enzymes may be added simultaneously in one step and/or sequentially in different steps.

Alternatively, a mixture with at least one compound as defined herein for step a) and at least one compound as defined herein for step b) and at least one enzyme as defined herein according to step c) may be incubated in one step without repetition of one or more steps. Such a proceeding may be preferable in certain circumstances, as it may lead to the largest variety of possible products.

The method of the present invention as defined above preferably leads to generation of compounds on the basis of universal donors as provided in step a) and acceptors as provided in step b) upon adding enzymes according to step c) and incubating the mixture (step e)). An optional or compulsory repetition of these steps and optionally a hydrogenolysis reaction may be carried out as defined above. Preferably, the method of the present invention as described herein results in either single human milk oligosaccharides (HMOs) or derivatives or precursors thereof, or a diversified mixture comprising two or more human milk oligosaccharides (HMOs) or derivatives or precursors thereof, the single compounds of which may be defined according to
compounds of general formula 1 and salts thereof:

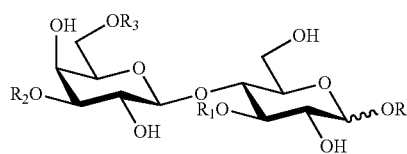

general formula 1 wherein
R is a group removable by hydrogenolysis,
$R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, $R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue;
compounds of general formula 2 and salts thereof

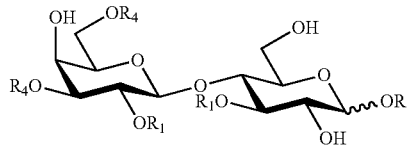

general formula 2 wherein
R is a group removable by hydrogenolysis,
$R_1$ independently of each other is fucosyl or H
$R_4$ independently of each other is sialyl or H,
with the proviso that at least one $R_1$ or $R_4$ is not H,
compounds of general formula 3 and salts thereof

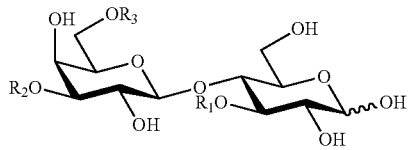

general formula 3 wherein
$R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue; and/or
compounds of general formula 4 and salts thereof

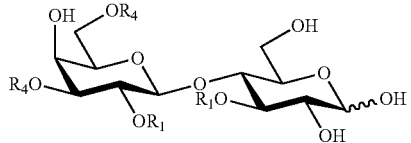

general formula 4 wherein
$R_1$ independently of each other is fucosyl or H
$R_4$ independently of each other is sialyl or H,
with the proviso that at least one $R_1$ or $R_4$ is not H.

Even more preferably, the method of the present invention for generation of human milk oligosaccharides (HMOs) results in either single human milk oligosaccharide derivatives, or a mixture comprising two or more human milk oligosaccharide (HMO) derivatives as defined above, preferably after incubation step e) and/or a repetition of steps according to step f) or g), wherein compounds of formulae 1 and 2 are further characterized by general formulae 1a, 1b or 2 and salts thereof

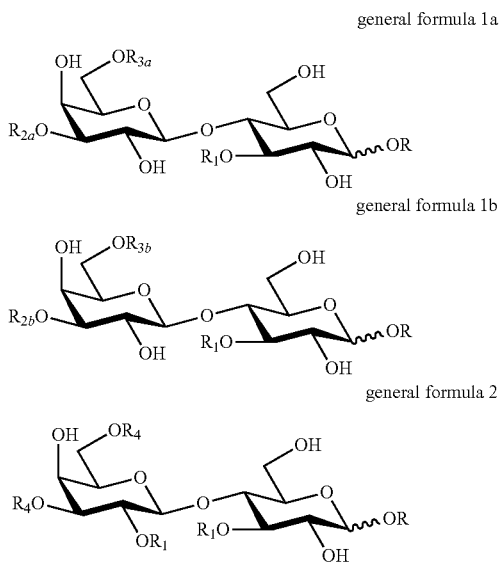

general formula 1a general formula 1b general formula 2 wherein
R, $R_1$ and $R_4$ are as defined above,
$R_{2a}$ is N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue,
$R_{3a}$ is H or N-acetyl-lactosaminyl group optionally substituted with a lacto-N-biosyl group; any N-acetyl-lactosaminyl and lacto-N-biosyl group can be substituted with one or more sialyl and/or fucosyl residue,
$R_{2b}$ is lacto-N-biosyl group optionally substituted with sialyl and/or fucosyl residue, and
$R_{3b}$ is H or N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue.

Particularly preferably, compounds obtained according to the method of the present invention for generation as defined above are characterized by their linkages and modifications. Preferably, the compounds obtained by the method of the present invention after incubation step e) and/or a repetition of steps according to step f) or g), preferably as defined according to general formulae 1a and 1b, are characterized in that:
the N-acetyl-lactosaminyl group in the glycosyl residue of $R_{2a}$ in general formula 1a is attached to the another N-acetyl-lactosaminyl group with 1-3 interglycosidic linkage,
the lacto-N-biosyl group in the glycosyl residue of $R_{2a}$ in general formula 1a is attached to the N-acetyl-lactosaminyl group with 1-3 interglycosidic linkage,
the lacto-N-biosyl group in the glycosyl residue of $R_{1a}$ in general formula 1a is attached to the N-acetyl-lactosaminyl group with 1-3 interglycosidic linkage,
the N-acetyl-lactosaminyl group in the glycosyl residue of $R_{3b}$ in general formula 1b is attached to the another N-acetyl-lactosaminyl group with 1-3 or 1-6 interglycosidic linkage,
the lacto-N-biosyl group in the glycosyl residue of $R_{3b}$ in general formula 1b is attached to the N-acetyl-lactosaminyl group with 1-3 interglycosidic linkage.

Preferably, the compounds obtained by the method of the present invention, after incubation step e) and/or a repetition of steps according to step f) and g), are characterized in that general formula 1a represents the R-glycosides of lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 1b represents the R-glycosides of lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

Preferably, the compounds obtained by the method of the present invention, after incubation step e) and/or a repetition of steps according to step f) or g), are characterized in that:
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

According to a further preferred aspect, compounds as obtained according to the method of the present invention, preferably compounds according to formulae 1 or 2 or of general subformulae 1a, 1b or 2 may be selected from the group of: R-glycosides of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, or salts thereof. The core structures of these compounds are shown in Table 6 below. The R-glycosides may be alpha or beta-anomers. Preferably, said R-glycosides are the beta-anomers.

TABLE 6

Core structures of R-glycosides of naturally occuring HMOs having a lactose, LNT or LNnT core

| Abbreviation | Chemical Structure |
|---|---|
| 2'-FL | Fuc(α1-2)Gal(β1-4)Glc |
| 3-FL | Gal(β1-4)Glc<br>        |<br>    Fuc(α1-3) |
| DFL | Fuc(α1-2)Gal(β1-4)Glc<br>                |<br>            Fuc(α1-3) |
| 3'-SL | Neu5Ac(α2-3)Gal(β1-4)Glc |
| FSL | Neu5Ac(α2-3)Gal(β1-4)Glc<br>                  |<br>              Fuc(α1-3) |
| LNT | Gal(β1-3)GlcNAc(β1-3)Gal(β1-4)Glc |
| LNFP I | Fuc(α1-2)Gal(β1-3)GlcNAc(β1-3)Gal(β1-4)Glc |

TABLE 6-continued

Core structures of R-glycosides of naturally occuring HMOs having a lactose, LNT or LNnT core

| Abbreviation | Chemical Structure |
|---|---|
| LNFP II | Gal(β1-3)GlcNAc(β1-3)Gal(β1-4)Glc<br>\|<br>Fuc(α1-4) |
| LNFP III | Gal(β1-4)GlcNAc(β1-3)Gal(β1-4)Glc<br>\|<br>Fuc(α1-3) |
| LNFP V | Gal(β1-3)GlcNAc(β1-3)Gal(β1-4)Glc<br>\|<br>Fuc(α1-3) |
| LNDFH I | Fuc(α1-2)Gal(β1-3)GlcNAc(β1-3)Gal(β1-4)Glc<br>\|<br>Fuc(α1-4) |
| LNDFH II | Gal(β1-3)GlcNAc(β1-3)Gal(β1-4)Glc<br>\|          \|<br>Fuc(α1-4)   Fuc(α1-3) |
| LNDFH III | Gal(β1-3)GlcNAc(β1-3)Gal(β1-4)Glc<br>\|          \|<br>Fuc(α1-3)   Fuc(α1-3) |
| LSTa | Neu5Ac(α2-3)Gal(β1-3)GlcNAc(β1-3)Gal(β1-4)Glc |
| LSTb | Neu5Ac(α2-6)<br>\|<br>Gal(β1-3)GlcNAc(β1-3)Gal(β1-4)Glc |
| LSTc | Neu5Ac(α2-6)Gal(β1-4)GlcNAc(β1-3)Gal(β1-4)Glc |
| F-LSTa | Neu5Ac(α2-3)Gal(β1-3)GlcNAc(β1-3)Gal(β1-4)Glc<br>\|<br>Fuc(α1-4) |
| F-LSTb | Neu5Ac(α2-6)<br>\|<br>Fuc(α1-2)Gal(β1-3)GlcNAc(β1-3)Gal(β1-4)Glc |
| F-LSTc | Neu5Ac(α2-6)Gal(β1-4)GlcNAc(β1-3)Gal(β1-4)Glc<br>\|<br>Fuc(α1-3) |
| DS-LNT | Neu5Ac(α2-6)<br>\|<br>Neu5Ac(α2-3)Gal(β1-3)GlcNAc(β1-3)Gal(β1-4)Glc |
| FDS-LNT I | Neu5Ac(α2-6)<br>\|<br>Neu5Ac(α2-3)Gal(β1-3)GlcNAc(β1-3)Gal(β1-4)Glc<br>\|<br>Fuc(α1-4) |
| FDS-LNT II | Neu5Ac(α2-6)<br>\|<br>Neu5Ac(α2-3)Gal(β1-3)GlcNAc(β1-3)Gal(β1-4)Glc<br>\|<br>Fuc(α1-3) |
| LNnT | Gal(β1-4)GlcNAc(β1-3)Gal(β1-4)Glc |

Most preferably, compounds as obtained according to the method of the present invention of generation of HMOs, preferably compounds according to formulae 1 or 2 or of general subformulae 1a, 1b or 2, may be selected from compounds wherein R is benzyl, or salts thereof.

According to a further specific aspect of the method of the present invention the compounds obtained according to the method of the present invention, preferably compounds according to any of formulae 1 or 2 or of general subformulae 1a, 1b or 2 or of general subformulae 1a, 1b or 2, are optionally subjected to a hydrogenolysis reaction subsequent to incubation according to step e) and/or a further repetition according to step f), resulting in the formation of HMOs characterized by general formulae 3 and 4.

Likewise preferably, the method of the present invention for generation of human milk oligosaccharides (HMOs) results in human milk oligosaccharides as defined above, preferably after incubation step e) and/or a repetition of steps according to step f) or g), wherein compounds of formulae 3 and 4 are further characterized by general formulae 3a, 3b or 4 and salts thereof

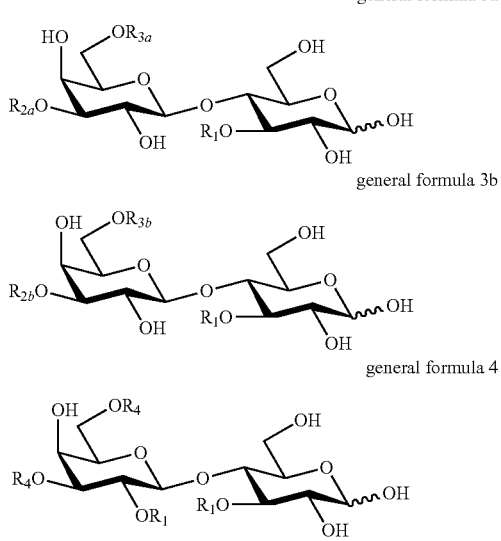

general formula 3a general formula 3b general formula 4 wherein $R_1$ and $R_4$ are as defined above, $R_{2a}$ is N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue, $R_{1a}$ is H or N-acetyl-lactosaminyl group optionally substituted with a lacto-N-biosyl group; any N-acetyl-lactosaminyl and lacto-N-biosyl group can be substituted with one or more sialyl and/or fucosyl residue, $R_{2b}$ is lacto-N-biosyl group optionally substituted with sialyl and/or fucosyl residue, $R_{3b}$ is H or N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue.

Particularly preferably, compounds obtained according to the method of the present invention for generation as defined above are characterized by their linkages and modifications. Preferably, the compounds obtained by the method of the present invention, after incubation step e) and/or a repetition of steps according to step f) or g), and as preferably defined according to general formulae 3a or 3b, are characterized in that:

the N-acetyl-lactosaminyl group in the glycosyl residue of $R_{2a}$ in general formula 3a is attached to another N-acetyl-lactosaminyl group with 1-3 interglycosidic linkage, the lacto-N-biosyl group in the glycosyl residue of $R_{2a}$ in general formula 3a is attached to the N-acetyl-lactosaminyl group with 1-3 interglycosidic linkage, the lacto-N-biosyl group in the glycosyl residue of $R_{1a}$ in general formula 3a is attached to the N-acetyl-lactosaminyl group with 1-3 interglycosidic linkage, the N-acetyl-lactosaminyl group in the glycosyl residue of $R_{3b}$ in general formula 3b is attached to another N-acetyl-lactosaminyl group with 1-3 or 1-6 interglycosidic linkage, the lacto-N-biosyl group in the glycosyl residue of $R_{3b}$ in general formula 3b is attached to the N-acetyl-lactosaminyl group with 1-3 interglycosidic linkage.

Preferably, the compounds obtained by the method of the present invention after incubation step e) and/or a repetition of steps according to step f) or g) are characterized in that general formula 3a represents lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 3b represents lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

Preferably, the compounds obtained by the method of the present invention, after incubation step e) and/or a repetition of steps according to step f) or g), are characterized in that:
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

According to a further preferred aspect, compounds as obtained according to the method of the present invention of generation of HMOs, preferably compounds according to general subformulae 3a, 3b or 4 may be selected from the group of: 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, or salts thereof. The core structures of these compounds are shown in Table 6 above.

Likewise preferably, the compounds obtained by the method of the present invention, after incubation step e) and/or a repetition of steps according to step f) or g), are obtained depending on the activity of the at least one enzyme comprising a transglycosidase activity and/or a glycosynthase activity as described above. Such an enzyme may be selected depending on the desired linkage or modification to be carried out during generation of HMOs using the method of the present invention.

Wild type or engineered fucosidases as defined above may be utilized herein, displaying transfucosidase activity and showing a $\alpha,1$-2, $\alpha,1$-3 and/or $\alpha,1$-4 regioselectivity are targeted in the present invention. Such wild type or engineered fucosidases preferably display transfucosidase activity and catalyze the transfer of the fucosyl residue to:
the galactose of the lacto-N-biosyl group with $\alpha,1$-2 interglycosidic linkage and/or
the N-acetyl-glucosamine of the lacto-N-biosyl group with $\alpha,1$-4 interglycosidic linkage and/or
the N-acetyl-glucosamine of the N-acetyl-lactosaminyl group with $\alpha,1$-3 interglycosidic linkage;

Such linkages are highly preferred in the context of the present method of the present invention and the compounds claimed herein, when using wild type or engineered fucosidases.

Additionally, wild type or engineered sialidases as defined above may be utilized herein, which display trans-sialidase activity and show a $\alpha,2$-3 and/or $\alpha,2$-6 regioselectivity. Such linkages are preferably targeted in the present invention. Such wild type or engineered sialidases preferably display trans-sialidase activity and catalyze the transfer of the sialyl residue to:
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

Such linkages are highly preferred in the context of the present method of the present invention and the compounds claimed herein, when using wild type or engineered sialidases.

Furthermore, wild type or engineered lacto-N-biosidases as defined above may be utilized herein, which display trans-lacto-N-biosidase activity and show a $\beta,1$-3 regioselectivity. Such linkages are preferably targeted in the present invention. Such wild type or engineered lacto-N-biosidases preferably display trans-lacto-N-biosidase activity and catalyze the transfer of the lacto-N-biosyl residue to an N-acetyl-lactosaminyl group with 1-3 interglycosidic linkage are targeted in the present invention. Such linkages are highly preferred in the context of the present method of the present invention and the compounds claimed herein, when using wild type or engineered lacto-N-biosidases.

Finally, wild type or engineered glycosidases as defined above may be utilized herein, which display trans-N-acetyl-lactosaminidase activity and show a $\beta,1$-3 and/or $\beta,1$-6 regioselectivity are targeted in the present invention. Such wild type or engineered glycosidases preferably display trans-N-acetyllactosaminidase activity and catalysize the transfer of the N-acetyl-lactosaminyl residue to another N-acetyl-lactosaminyl group with 1-3 or 1-6 interglycosidic linkage. Such linkages are highly preferred in the context of the present method of the present invention and the compounds claimed herein, when using wild type or engineered N-acetyllactosaminidases.

According to another specific aspect of the method of the present invention the compounds obtained according to the method of the present invention, preferably compounds according to any of formulae 1, 2, 3 or 4 or of general subformulae 1a, 1b or 2 or of general subformulae 3a, 3b or 4 are optionally subjected to a purification reaction preferably via crystallization or precipitation.

According to a specific aspect of the method of the present invention the compounds obtained according to the method of the present invention, preferably compounds according to any of formulae 1, 2, 3 or 4 or of general subformulae 1a, 1b or 2 or of general subformulae 3a, 3b or 4 are optionally spray-dried.

According to a very particular aspect, the compounds obtained according to the present method of the present invention may be one or more naturally occurring HMO R-glycosides, preferably compounds according to formulae 1 or 2 or of general subformulae 1a, 1b or 2, or one or more naturally occurring HMOs, preferably compounds according to formulae 3 or 4 or of general subformulae 3a, 3b or 4. Naturally occurring HMOs are listed in TADASU URASHIMA et al, MILK OLIGOSACCHARIDES, Nova Biomedical Books, New York, 2011, ISBN: 978-1-61122-831-1, Table 4 in pp. 14-25.

Furthermore, according to a very particular aspect, the compounds obtained according to the present method of the present invention may be an HMO, wherein the HMO is derivatized with benzyl.

According to a further specific aspect of the method of the present invention the compounds obtained according to the method of the present invention, preferably single compounds or mixture of two or more compounds according to any of formulae 1 or 2 or of general subformulae 1a, 1b or 2 are optionally subjected to a hydrogenolysis reaction resulting in the formation of single HMOs or mixture of two or more HMOs characterized by general formulae 3 and 4.

According to an optional hydrogenolysis step, single compounds or mixture of two or more compounds according to any of formulae 1 or 2 or of general subformulae 1a, 1b or 2 after step e), f) or g) may be subjected to a hydrogenolysis reaction, e.g. as defined herein. In this context, such an optional hydrogenolysis step is preferably carried out to obtain the naturally occurring naked HMOs, e.g. as defined according to any of formulae as defined above, and to preferably remove possible protecting groups, such as benzyl groups.

Catalytic hydrogenolysis typically takes place in a protic solvent or in a mixture of protic solvents. A protic solvent may be selected from the group consisting of water, acetic acid or $C_1$-$C_6$ alcohols. A mixture of one or more protic solvents with one or more suitable aprotic organic solvents partially or fully miscible with the protic solvent(s) (such as THF, dioxane, ethyl acetate or acetone) may also be used. Water, one or more $C_1$-$C_6$ alcohols or a mixture of water and one or more $C_1$-$C_6$ alcohols are preferably used as the solvent system. Solutions containing the carbohydrate derivatives in any concentration or suspensions of the carbohydrate derivatives in the solvent(s) used are also applicable. The reaction mixture is stirred at a temperature in the range of 10-100° C., preferably between 20-50° C., in a hydrogen atmosphere of 1-50 bar absolute (100 to 5000 kPa) in the presence of a catalyst such as palladium, Raney nickel or any other appropriate metal catalyst, preferably palladium on charcoal or palladium black, until reaching the completion of the reaction. Transfer hydrogenolysis may also be performed, when the hydrogen is generated in situ from cyclohexene, cyclohexadiene, formic acid or ammonium formate. Addition of organic or inorganic bases or acids and/or basic and/or acidic ion exchange resins can also be used to improve the kinetics of the hydrogenolysis. The use of basic substances is especially preferred when halogen substituents are present on the substituted benzyl moieties of the precursors and/or the formation of mannosamine base is desirable. Preferred organic bases include, but are not limited to, triethylamine, diisopropyl ethylamine, ammonia, ammonium carbamate and diethylamine. An organic or an inorganic acid is favourably used as a co-solvent or additive in cases when mannosamine salts are the intended products. Preferred acids include, but are not limited to, formic acid, acetic acid, propionic acid, chloroacetic acid, dichloroacetic acid, trifluoroacetic acid, HCl and HBr. The conditions proposed above allow simple, convenient and delicate removal of the solvent(s) giving rise to a mixture or blend of pure HMOs.

Accordingly, a further aspect of the present invention relates to providing single compounds or a mixture of two or more compounds, which compounds are characterized by general formula 1 and salts thereof

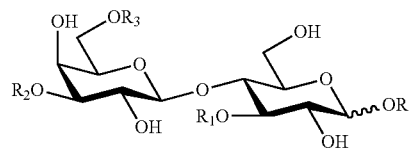

general formula 1 wherein

R is a group removable by hydrogenolysis, $R_1$ is fucosyl or H, $R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, $R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, with the proviso that, if provided alone, the compound is not LNnT R-glycoside or LNT benzyl glycoside;

or general formula 2 and salts thereof

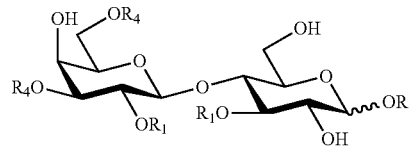

general formula 2 wherein

R is a group removable by hydrogenolysis, $R_1$ independently of each other is fucosyl or H $R_4$ independently of each other is sialyl or H, with the proviso that, that at least one of $R_1$ or $R_4$ is not H, and, if provided alone, the compound is not 3'-sialyllactose benzyl glycoside sodium salt or 6'-sialyllactose R-glycoside.

Even more preferably, the invention relates to either single human milk oligosaccharide derivatives, or a diversified mixture comprising two or more human milk oligosaccharide (HMOs) derivatives, wherein compounds of formulae 1 and 2 defined above are further characterized by general formulae 1a, 1b or 2 and salts thereof

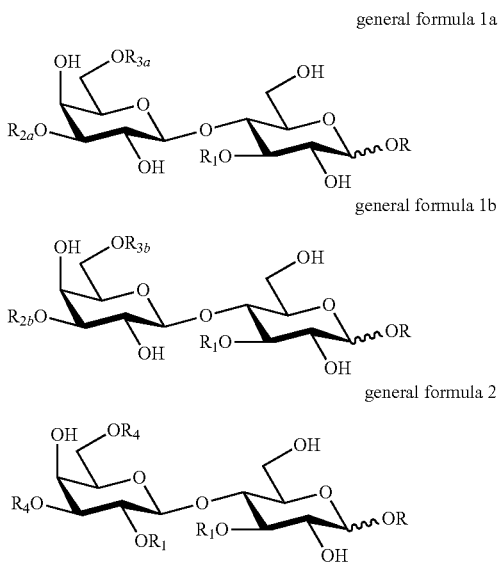

general formula 1a general formula 1b general formula 2 wherein
R, $R_1$ and $R_4$ are as defined above,
$R_{2a}$ is N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue,
$R_{1a}$ is H or N-acetyl-lactosaminyl group optionally substituted with a lacto-N-biosyl group; any N-acetyl-lactosaminyl and lacto-N-biosyl group can be substituted with one or more sialyl and/or fucosyl residue,
$R_{2b}$ is lacto-N-biosyl group optionally substituted with sialyl and/or fucosyl residue, and
$R_{3b}$ is H or N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue.

Particularly preferably, compounds defined above are characterized by their linkages and modifications. Preferably, the compounds defined according to general formulae 1a and 1b, are characterized in that:
the N-acetyl-lactosaminyl group in the glycosyl residue of $R_{2a}$ in general formula 1a is attached to another N-acetyl-lactosaminyl group with 1-3 interglycosidic linkage,
the lacto-N-biosyl group in the glycosyl residue of $R_{2a}$ in general formula 1a is attached to the N-acetyl-lactosaminyl group with 1-3 interglycosidic linkage,
the lacto-N-biosyl group in the glycosyl residue of $R_{1a}$ in general formula 1a is attached to the N-acetyl-lactosaminyl group with 1-3 interglycosidic linkage,
the N-acetyl-lactosaminyl group in the glycosyl residue of $R_{3b}$ in general formula 1b is attached to another N-acetyl-lactosaminyl group with 1-3 or 1-6 interglycosidic linkage,
the lacto-N-biosyl group in the glycosyl residue of $R_{3b}$ in general formula 1b is attached to the N-acetyl-lactosaminyl group with 1-3 interglycosidic linkage.

Preferably, the compounds characterized by general formula 1a represent the R-glycosides of lacto-N-tetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 1b represent the R-glycosides of lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

According to a further preferred aspect, compounds as defined above may be selected from the group of: R-glycosides of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, or salts thereof. The R-glycosides may be alpha or beta-anomers. Preferably, said R-glycosides are the beta-anomers and more preferably R is benzyl.

According to a further embodiment, the method of the present invention further comprises addition of the compounds obtained in the incubation step or after the hydrogenolysis step to a consumable product, preferably as defined herein. The consumable product is preferably at least one of a pharmaceutical or nutritional formulation and preferably a liquid or a solid. According to another embodiment, the method may further comprise the addition of pharmaceutically acceptable carriers and/or the addition of prebiotics to the compounds obtained in the incubation step.

According to a second aspect, the present invention also provides a compound, particularly a mixture of HMOs, characterized and specified above, obtained or obtainable by the method of the present invention as described herein.

According to a further embodiment of the second aspect, the present invention provides a compound, preferably a mixture of compounds, more preferably a mixture of HMOs, obtained or obtainable by the method of the present invention as described herein. In this context, such a mixture of compounds obtained or obtainable by the method of the present invention as described herein is preferably to be understood as a mixture of at least 2 to 10, 2 to 10, 2 to 20, 2 to 20, 2 to 100, 2 to 200, or even more different compounds as generally defined above. Such compounds may be preferably selected without restriction from any of the compounds as defined according to any of formulae 1, 2, 3 or 4 or of any subformulae or selection as defined above.

According to a third aspect, the present invention also provides compounds which may be utilized in the present invention, e.g. as acceptor, and compounds which may be obtained during the method of the present invention of generation of HMOs.

The present invention also provides or utilizes salts of herein defined compounds. Such salts may be preferably selected from salts of the compounds according to general formulae 1-4 or subformulae thereof, which contain at least one sialyl residue, in salt form: an associated ion pair consisting of the negatively charged acid residue of sialylated oligosaccharides falling under general formulae 1-4 or subformulae thereof and one or more cations in any stoichiometric proportion. Cations, as used in the present context, are atoms or molecules with positive charge. The cation may be inorganic or organic. Preferred inorganic cations are ammonium ion, alkali metal, alkali earth metal and transition metal ions, more preferably $Na^+$, $K^+$, $Ca^{2+}$, $Mg^{2+}$, $Ba^{2+}$, $Fe^{2+}$, $Zn^{2+}$, $Mn^{2+}$ and $Cu^{2+}$, most preferably $K^+$, $Ca^{2+}$, $Mg^{2+}$, $Ba^{2+}$, $Fe^{2+}$ and $Zn^{2+}$. Basic organic compounds in positively charged form may be relevant organic cations. Such preferred positively charged counterparts are diethyl amine, triethyl amine, diisopropyl ethyl amine, ethanolamine, diethanolamine, triethanolamine, imidazole, piperidine, piperazine, morpholine, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having a free amino group on the N-terminal, etc., all in protonated form. Such salt formations can be used to modify characteristics of the complex molecule as a whole, such as stability, compatibility to excipients, solubility and the ability to form crystals.

According to a particular embodiment of the third aspect, the compounds as defined herein may be subjected to a hydrogenolysis reaction, e.g. as defined herein, preferably, if R is not H, even more preferably, if R is benzyl. Such a hydrogenolysis reaction is preferably carried out as described above. Preferably, R may be as defined herein to be cleavable in a hydrogenolysis reaction, preferably as described above.

In a further embodiment of the third aspect, compounds or a mixture of compounds, more preferably a mixture of HMOs, obtained or obtainable by the method of the present invention as described herein or any further compound as defined herein, may be used for the preparation of a consumable product, preferably for the preparation of a pharmaceutical composition, a nutritional formulation or a food supplement. Such a compound or mixture of compounds, more preferably a mixture of HMOs, obtained or obtainable by the method of the present invention as described herein is particularly effective in the improvement and maturation of the immune system of neonatal infants, and has preventive effect against secondary infections following viral infections such as influenza. The use of compounds or a mixture of compounds, more preferably a mixture of HMOs, obtained or obtainable by the method of the present invention as described herein as prebiotic enhances the beneficial effects and efficiency of probiotics, such as *Lactobacillus* and *Bifidobacterium* species, in promoting the development of an early bifidogenic intestinal microbiota in infants, in reducing the risk of development or allergy and/or asthma in infants, and in preventing and treating pathogenic infections in such as diarrhea in infants.

In a fourth aspect, the present invention provides a pharmaceutical composition, comprising compounds or a mixture of compounds, more preferably a mixture of HMOs, obtained or obtainable by the method of the present invention as described herein, and preferably a pharmaceutically acceptable carrier. "Pharmaceutically acceptable carriers" include but are not limited to additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. The dosage form for administration includes, for example, tablets, powders, granules, pills, suspensions, emulsions, infusions, capsules, injections, liquids, elixirs, extracts and tinctures.

In a fifth aspect, nutritional formulations are provided such as foods or drinks, comprising compounds or a mixture of compounds, more preferably a mixture of HMOs, obtained or obtainable by the method of the present invention as described herein. The nutritional formulation may contain edible micronutrients, vitamins and minerals as well. The amounts of such ingredient may vary depending on whether the formulation is intended for use with normal, healthy infants, children, adults or subjects having specialized needs (e.g. suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolyzed cornstarch, etc.) and proteins from casein, soy-bean, whey or skim milk, or hydrolysates of these proteins, but protein from other source (either intact or hydrolysed) may be used as well. Vitamins may be chosen from the group consisting of vitamin A, B1, B2, B5, B6, B12, C, D, E, H, K, folic acid, inositol and nicotinic acid. The nutritional formula may contain the following minerals and trace elements: Ca, P, K, Na, Cl, Mg, Mn, Fe, Cu, Zn, Se, Cr or I.

According to a general embodiment of the fifth aspect, a nutritional formulation as defined above may further contain one or more probiotics, e.g. lacto bacteriae, *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet. Probiotics are preferably also contained in the nutritional formulation in an amount sufficient to achieve the desired effect in an individual, preferably in infants, children and/or adults.

In a preferred embodiment, the nutritional formulation as defined above is an infant formula. In the context of the present invention, the term "infant formula" preferably means a foodstuff intended for particular nutritional use by infants during the first 4-6 months or even 4 to 12 months of life and satisfying by itself the nutritional requirements of infants. It may contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet.

In a sixth aspect, a food supplement may be provided. Such a food supplementcontains ingredients as defined for nutritional food above, e.g. compounds or a mixture of compounds, more preferably a mixture of HMOs, obtained or obtainable by the method of the present invention as described herein, vitamins, minerals, trace elements and other micronutritients, etc. The food supplement may be for example in the form of tablets, capsules, pastilles or a liquid. The supplement may contain conventional additives selected from but not limited to binders, coatings, emulsifiers, solubilising agents, encapsulating agents, film forming agents, adsorbents, carriers, fillers, dispersing agents, wetting agents, gellifying agents, gel forming agents, etc.

According to a preferred embodiment, the food supplement is a digestive health functional food as the administration of compounds or a mixture of compounds, more preferably a mixture of HMOs, obtained or obtainable by the method of the present invention as described herein, provides a beneficial effect on digestive health. A digestive health functional food is preferably a processed food used with the intention of enhancing and preserving digestive health by utilizing compounds or a mixture of compounds, more preferably a mixture of HMOs, obtained or obtainable by the method of the present invention as described herein, as physiologically functional ingredients or components in forms of tablet, capsule, powder, etc. Different terms such as dietary supplement, nutraceutical, designed food, or health product may also be used to refer to a digestive health functional food.

In a further aspect, compounds or a mixture of compounds, more preferably a mixture of HMOs, obtained or obtainable by the method of the present invention as described herein, may be used for the preparation of nutritional formulations including foods, drinks and feeds, preferably infant formulas, food supplements and digestive health functional foods, preferably any of these as described above. The nutritional formulation may be prepared in any usual manner.

According to another aspect of the present invention is provided glycosyl donors used in the present invention which are characterized by general formulae 5'-8'

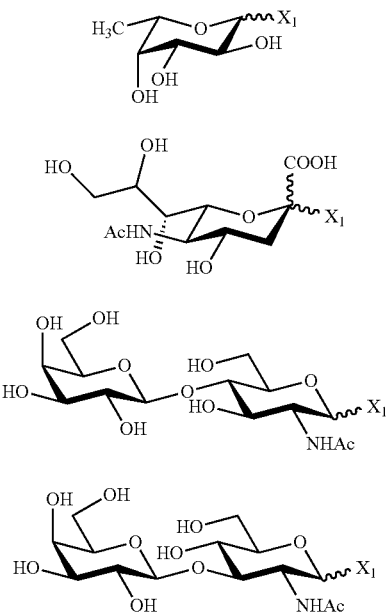

wherein $X_1$ is group A or group B

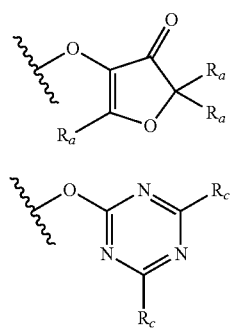

wherein $R_a$ is independently H or alkyl, or two vicinal $R_a$ groups represent a=$C(R_b)_2$ group, wherein $R_b$ is independently H or alkyl, and $R_c$ is independently selected from the group consisting of alkoxy, amino, alkylamino and dialkylamino, and/or a compound of any of the following formulae

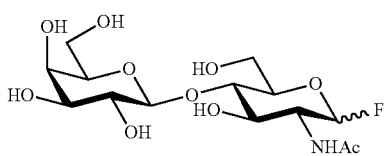

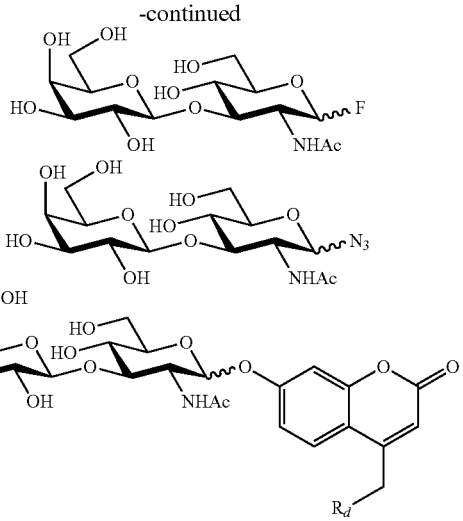

wherein $R_d$ is selected from the group consisting of H, alkyl and —C(=O)$R_e$, and wherein $R_e$ is OH, alkoxy, amino, alkylamino, dialkylamino, hydrazino, alkylhydrazino, dialkylhydrazino or trialkylhydrazino, or a salt of any of the aforementioned compounds.

In preferred compounds $X_1$ is group A, wherein $R_a$ is independently H or $C_{1-6}$ alkyl, preferably H or methyl. These compounds are especially advantageous donors in glycosylation/transglycosylation reactions because their water solubility is high, the leaving group after glycosylation can be detected easily by UV detection, and $X_1$ leaving group, being a natural aroma of fruits, causes no regulatory obstacles when using in the food industry.

In the present invention, if not otherwise indicated, different features of alternatives and embodiments may be combined with each other, where suitable.

Whilst the invention has been described with reference to a preferred embodiment, it will be appreciated that various modifications are possible within the scope of the invention.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

EXPERIMENTAL

Example 1

General Procedure for Transglycosylation Reactions

A solution of appropriate glycosyl donor(s) such as derivatives of general formula 5 to 10 and glycosyl acceptor(s) (10 mM-1M) was incubated in an incubation buffer at a pH range from 5.0 to 9.0 with recombinant glycosidase, α-transglycosidase or α-glycosynthase, such as α-fucosidase, α-transfucosidase, α-fucosynthase, α-sialidase, α-transsialidase, β-lacto-N-biosidase β-trans-lacto-N-biosidase, β-N-acetyllactosaminidase or β-trans-N-acetyllactosaminidase. The reaction mixture was stirred at a temperature in the range of from 20 to 70° C. Samples were taken at different times of the reaction, the reaction was stopped by the addition of 1M $NaHCO_3$-solution at pH=10 and products were analyzed by HPLC, or/and LC-MS, or/and LC-MS-MS. After completion, the enzyme was denatured and centrifuged.

The resulting solution was evaporated under reduced pressure. After lyophilisation, the dry residue was dissolved in water and products were purified by biogel chromatography (P-2 Biogel, 16×900 mm) with water or by reverse phase chromatography.

The following recombinant enzymes were used and tested in the transglycosylation reaction:

Transfucosidase P25 from *Thermotoga maritima* (see seq. ID 1) containing mutations G226S Y237H T264A L322P Transfucosidase M3 from *Thermotoga maritima* (see seq. ID 1) containing mutations Y237H Y267F L322P.

Transsialidase from *Trypanosoma cruzi* (see seq. ID 15, 16)

Fucosidase Blon_2336 from *Bifidobacterium longum* subsp. *infantis* ATCC 15697 (see seq. ID 5)

These transglycosidases were produced in *E. coli* as reported in Osanjo et al. *Biochemistry* 46, 1022 (2007), Sela et al. *Appl. Environ. Microbiol.* 78, 795 (2012), Agusti et al. *Glycobiology* 14, 659 (2004) and Neubacher et al. *Org. Biomol. Chem.* 3, 1551 (2005). Purified transglycosidases were stored at −20° C. to +4° C.

Example 2

Sialylation Using p-Nitrophenyl Sialoside Donor

General procedure: a solution of 2-O-(p-nitrophenyl)-α-D-sialoside (75 µmol) and the appropriate sialyl acceptor (35 µmol) in degassed incubation buffer (1.0 ml, 100 mM Tris/HCl, pH 7.5, 50 mg BSA, 0.02% $NaN_3$) was incubated with recombinant transsialidase from *T. cruzi* (80 µl, 1.3 mg/ml) at 23° C. for 24 h. The reaction was monitored by TLC (butanol/acetic acid/water 5:2:2). After completion, the enzyme was denatured and centrifuged before the supernatant is lyophilized. The dry residue was dissolved in water and purified by biogel chromatography (P-2 Biogel, 16×900 mm) with water or by reverse phase chromatography. The yields vary between 45-85%.

4-Chlorobenzyl 3'-O-sialyl-β-lactoside $^1$H-NMR (500 MHz, $D_2O$): δ [ppm]=7.46-7.42 (m, 4H, $H_{(a/b)arom}$); 4.91 (d, 1H, $CH_2$a-Bn); 4.74 (d, 1H, $CH_2$b-Bn); 4.55-4.52 (m, 2H, H-1/H-1'); 4.11 (dd, 1H, H-3'); 2.76 (dd, 1H, H-3"$_{eq}$); 2.04 (s, 3H, $COCH_3$); 1.81 (dd, 1H, H-3"$_{ax}$).

$J_{(a,b)-Bn}$=11.8; $J_{2',3'}$=9.9; $J_{3',4'}$=2.9; $J_{3"ax,3"eq}$=12.4; $J_{3"ax,4"}$=12.1; $J_{3"eq,4"}$=4.5 Hz.

$^{13}$C-NMR (126 MHz, $D_2O$): δ [ppm]=135.2, 133.5 (quart. $C_{arom}$); 130.2 ($CH_{a\text{-}arom}$); 128.6 ($CH_{b\text{-}arom}$); 102.6 (C-1'); 101.1 (C-1); 51.7 (C-5"); 39.6 (C-3"); 22.0 ($COCH_3$).

4-Methylbenzyl 3'-O-sialyl-β-lactoside $^1$H-NMR (500 MHz, $D_2O$): δ [ppm]=7.36 (d, 2H, H-a$_{arom}$); 7.28 (d, 2H, H-b$_{arom}$); 4.89 (d, 1H, $CH_2$a-Bn); 4.72 (d, 1H, $CH_2$b-Bn); 4.54-4.52 (m, 2H, H-1/H-1'); 4.12 (dd, 1H, H-3'); 2.76 (dd, 1H, H-3"$_{eq}$); 2.35 (s, 3H, $CH_3$-Tol); 2.04 (s, 3H, $COCH_3$); 1.81 (dd, 1H, H-3"$_{ax}$).

$J_{(a,b)arom}$=7.9; $J_{(a,b)-Bn}$=11.5; $J_{2',3'}$=9.9; $J_{3',4'}$=3.0; $J_{3"ax,3"eq}$=12.5; $J_{3",4"}$=12.2; $J_{3"eq,4"}$=4.6 Hz.

$^{13}$C-NMR (126 MHz, $D_2O$): δ [ppm]=138.8, 133.4 (quart. $C_{arom}$); 129.3 ($CH_{a\text{-}arom}$); 129.0 ($CH_{b\text{-}arom}$); 102.6 (C-1'); 100.9 (C-1); 99.8 (C-2"); 51.7 (C-5"); 39.6 (C-3"); 22.0 ($COCH_3$); 20.2 ($CH_3$-Tol).

2-Naphthylmethyl 3'-O-sialyl-β-lactoside $^1$H-NMR (500 MHz, $D_2O$): δ [ppm]=7.99-7.97 (m, 4H, H-arom); 7.62-7.59 (m, 3H, H-arom); 5.10 (d, 1H, $CH_2$a-Bn); 4.95 (d, 1H, $CH_2$b-Bn); 4.60 (d, 1H, H-1); 4.53 (d, 1H, H-1'); 4.12 (dd, 1H, H-3'); 2.77 (dd, 1H, H-3"$_{eq}$); 2.04 (s, 3H, $COCH_3$); 1.81 (dd, 1H, H-3"$_{ax}$).

$J_{(a,b)-Bn}$=11.9; $J_{1',2'}$=8.0; $J_{1',2'}$=7.9; $J_{2',3'}$=9.9; $J_{3',4'}$=3.0; $J_{3"ax,3"eq}$=12.5; $J_{3"ax,4"}$=12.1; $J_{3"eq,4"}$=4.6 Hz.

$^{13}$C-NMR (126 MHz, $D_2O$): δ [ppm]=128.3, 127.9, 127.7, 127.6, 126.6, 126.5 ($CH_{arom}$); 102.6 (C-1'); 101.1 (C-1); 51.7 (C-5"); 22.0 ($COCH_3$).

3-Phenylbenzyl 3'-O-sialyl-β-lactoside $^1$H-NMR (400 MHz, $D_2O$): δ [ppm]=7.75-7.44 (m, 9H, H-arom); 4.99 (d, 1H, $CH_2$a-Bn); 4.82 (d, 1H, $CH_2$b-Bn); 4.57 (d, 1H, H-1); 4.53 (d, 1H, H-1'); 4.13 (dd, 1H, H-3'); 2.78 (dd, 1H, H-3"$_{eq}$); 2.05 (s, 3H, $COCH_3$); 1.82 (dd, 1H, H-3"$_{ax}$).

$J_{(a,b)-Bn}$=11.8; $J_{1,2}$=8.0; $J_{1',2'}$=7.9; $J_{2',3'}$=9.9; $J_{3',4'}$=3.1; $J_{3"ax,3"eq}$=12.5; $J_{3"ax,4"}$=12.0; $J_{3"eq,4"}$=4.6 Hz.

$^{13}$C-NMR (100 MHz, $D_2O$): δ [ppm]=140.9, 140.3, 137.5 (quart. $C_{arom}$); 129.4, 129.2, 127.9, 127.8, 127.1, 127.0, 126.9, ($CH_{arom}$); 102.7 (C-1'); 101.2 (C-1); 99.6 (C-2"); 51.8 (C-5"); 39.7 (C-3"); 22.1 ($COCH_3$).

Benzyl 3'''-O-sialyl-β-LNnT $^1$H-NMR (400 MHz, $D_2O$): see FIG. 3.

Example 3

Sialylation Using p-Nitrophenyl Sialoside Donor

General procedure: a solution of 2-O-(p-nitrophenyl)-α-D-sialoside (47-51 mM) and benzyl β-LNT (24-37 mM) in incubation buffer (0.5 ml, 100 mM Tris/HCl, pH 7.0) was incubated with recombinant transsialidase from *T. cruzi* (21-108 µg/ml) at 15° C. Samples were taken after 3, 6 and 24 hours (50 µl each) and analyzed by HPLC. Formation of sialyl-β-LNT benzyl glycoside was detected with 65-95% conversion.

Example 4

Sialylation Using p-Nitrophenyl Sialoside Donor

General procedure: a solution of 2-O-(p-nitrophenyl)-α-D-sialoside (50 mM) and 3-FL (25-50 mM) in incubation buffer (0.5 ml, 100 mM Tris/HCl, pH 7.0) was incubated with recombinant transsialidase from *T. cruzi* (21-108 µg/ml) at 15° C. Samples were taken after 3, 6 and 24 hours (50 µl each) and qualitatively analyzed by TLC. Formation of sialyl-fucosyllactose was detected with medium conversion rate.

Example 5

Sialylation Using p-Nitrophenyl Sialoside Donor

General procedure: a solution of 2-O-(p-nitrophenyl)-α-D-sialoside (50 mM) and LNT (25-50 mM) in incubation buffer (0.5 ml, 100 mM Tris/HCl, pH 7.0) was incubated with recombinant transsialidase from *T. cruzi* (21-108 μg/ml) at 15° C. Samples were taken after 3, 6 and 24 hours (50 μl each) and qualitatively analyzed by TLC. Formation of sialyl-LNT was detected with high conversion rate.

Example 6

Fucosylation Using the Following Transfucosidases

P25 from *Thermotoga Maritima* containing mutations G226S Y237H T264A L322P;

M3 from *Thermotoga Maritima* containing mutations Y237H Y267F L322P.

General procedure: a solution of fucosyl donor and acceptor in degassed incubation buffer (0.5 ml, 50 mM citrate-phosphate, 145 mM NaCl, pH 5.5) was incubated with transfucosidase at 60° C. (except for fucosyl fluoride as donor, where the incubation was carried out at 35° C.). Sample was taken after 21 hours and the conversion determined by HPLC.
Results:
P25 Mutant:
  200 mM 2,5-dimethyl-4-oxo-3-furanyl α-L-fucopyranoside, 200 mM lactose, conversion: 6% 2'-FL
  500 mM 2,5-dimethyl-4-oxo-3-furanyl α-L-fucopyranoside, 500 mM lactose, conversion: 9% 2'-FL
  500 mM 2,5-dimethyl-4-oxo-3-furanyl α-L-fucopyranoside, 1000 mM lactose, conversion: 22% 2'-FL
  200 mM 2,5-dimethyl-4-oxo-3-furanyl α-L-fucopyranoside, 200 mM LNT, conversion: 13% fucosylated LNT (position of fucosylation not determined)
  500 mM 2,5-dimethyl-4-oxo-3-furanyl α-L-fucopyranoside, 500 mM LNT, conversion: 10% fucosylated LNT (position of fucosylation not determined)
M3 mutant:
  200 mM 2,5-dimethyl-4-oxo-3-furanyl α-L-fucopyranoside, 200 mM lactose, conversion: 19% 2'-FL
  500 mM 2,5-dimethyl-4-oxo-3-furanyl α-L-fucopyranoside, 1000 mM lactose, conversion: 35% 2'-FL
  200 mM 2,5-dimethyl-4-oxo-3-furanyl α-L-fucopyranoside, 200 mM LNT, conversion: 19% fucosylated LNT (position of fucosylation not determined)
  500 mM 2,5-dimethyl-4-oxo-3-furanyl α-L-fucopyranoside, 500 mM LNT, conversion: 20% fucosylated LNT (position of fucosylation not determined)
  200 mM fucosyl fluoride, 200 mM LNT, conversion: 10% fucosylated LNT (position of fucosylation not determined).

Example 7

Sialylation of Multiple Acceptors Using p-Nitrophenyl Sialoside Donor

Protocol: A solution of pNP-α-NeuAc as donor (150 mM) with 3-fucosyllactose, lacto-N-tetraose and lacto-N-neotetraose as acceptors (50 mM each) was incubated in incubation buffer Tris-HCl (100 mM) at a pH 7.0 with recombinant transsialidase from *Trypanosoma cruzi*. The reaction mixture was stirred at a temperature of 30° C. for 24 h. Products were analyzed by HPLC and LC-MS using reference standards (for SFL, LSTa, LSTd).

Products detected: 3'-sialyl-3-fucosyllactose, LSTa: Neu5Acα2-3Galβ1-3GlcNAcβ1-3Galβ1-4Glc, sialylated lacto-N-neotetraose (LSTd): Neu5Acα2-3Galβ1-4GlcNAcβ1-3Galβ1-4Glc, disialylated Lacto-N-tetraose and/or disialylated lacto-N-neotetraose, correct molecular mass was confirmed by LC-MS (1290 [M+H]$^+$, 1307 [M+NH$_4$]$^+$, 1328 [M+K]$^+$).

Example 8

Sialylation of Multiple Acceptors Using p-Nitrophenyl Sialoside as Donor

Protocol: A solution of pNP-α-NeuAc as donor (100 mM) with lacto-N-tetraose-β-OBn and lacto-N-neotetraose-β-OBn as acceptors (50 mM each) was incubated in incubation buffer Tris-HCl (100 mM) at a pH 7.0 with recombinant transsialidase from *Trypanosoma cruzi*. The reaction mixture was stirred at a temperature of 30° C. for 30 min. Products were analyzed by HPLC and LC-MS.

Example 9

Glycosylation of LNT Using Multiple Donors and Enzymes

Protocol: In a first cycle, a solution of α-L-fucosyl fluoride as donor (200 mM) with lacto-N-tetraose as acceptor (200 mM) was incubated in incubation buffer KHPO$_4$ (100 mM) at pH 7.0 with the recombinant transfucosidase M3 from *Thermotoga maritima*. The reaction mixture was stirred at a temperature of 30° C. for 24 hours.

In a second cycle, the pH of the resulting reaction mixture was adjusted to 7.0 and the solution was incubated at 30° C. for an additional 30 min after adding 200 mM of α-L-fucosyl fluoride and the recombinant fucosidase Blon_2336 from *Bifidobacterium longum* subsp. *infantis* ATCC 15697.

In a third cycle, the pH of the resulting reaction mixture was adjusted to 7.0 and the solution was incubated at 30° C. for an additional 24 h after adding 50 mM of pNP-α-NeuAc and the recombinant transsialidase from *Trypanosoma cruzi*. The reaction was stopped by addition of 1M NaHCO$_3$-solution at pH=10 and products were analyzed by HPLC, LC-MS and LC-MS-MS.

LC-MS Conditions:
  Instrument: AB Sciex API 2000 tandem MS
  Ionization mode: electrospray in positive mode
  Scan type: Q1MS
  Sample insertion mode: HPLC
  Column: TSK Gel amide 80 (Tosoh, 3 μm, 150×4.6 mm)
  Eluent: 10 mM ammonium formate buffer pH=6-acetonitrile: 30%/70%
  Flow rate: 1 ml/min
  Injected volume: 5 μl
Result:

| Retention time (min) | Molecular mass (Dalton) | Mass (Dalton) of the main fragment ions of the MH$^+$ in MS/MS |
|---|---|---|
| 12.2 | 998 (sialyl LNT) | 819, 657, 546, 454, 366, 274, 204, 186, 168 |
| 16.3 | 707 | |
| 19.7 | 853 (fucosyl LNT I) | 512, 366, 204, 186, 138 |
| 25.7 | 853 (fucosyl LNT II) | 512, 366, 350, 204, 186, 138 |

Example 10

Glycosylation of LNnT Using Multiple Donors and Enzymes

Protocol: In a first cycle, a solution of α-L-fucosyl fluoride as donor (200 mM) with lacto-N-tetraose as acceptor (200 mM) was incubated in incubation buffer KHPO$_4$ (100 mM) at pH 7.0 with the recombinant transfucosidase M3 from *Thermotoga maritima*. The reaction mixture was stirred at a temperature of 30° C. for 24 hours.

In a second cycle, the pH of the resulting reaction mixture was adjusted to 7.0 and the solution was incubated at 30° C. for an additional 30 min after adding 200 mM of α-L-fucosyl fluoride and the recombinant fucosidase Blon_2336 from *Bifidobacterium longum* subsp. *infantis* ATCC 15697.

In a third cycle, the pH of the resulting reaction mixture was adjusted to 7.0 and the solution was incubated at 30° C. for an additional 24 h after adding 50 mM of pNP-α-NeuAc and the recombinant transsialidase from *Trypanosoma cruzi*. The reaction was stopped by addition of 1M $NaHCO_3$-solution at pH=10 and products were analyzed by HPLC, LC-MS and LC-MS-MS.

Results (HPLC Condition: See Example 9):

| Retention time (min) | Molecular mass (Dalton) | Mass (Dalton) of the main fragment ions of the $MH^+$ in MS/MS |
| --- | --- | --- |
| 11.2 | 998 (sialyl LNnT) | 657, 546, 454, 366, 292, 274, 204, 138 |
| 16.9 | 707 | |
| 25.1 | 853 (fucosyl LNnT) | 512, 366, 204, 186, 138 |

Example 11

Fucosylation Reactions

General procedure: A solution of the appropriate fucosyl donor (such as p-nitrophenyl α-L-fucopyranoside, α-L-fucosyl fluoride, 2,5-dimethyl-3-oxo-(2H)-furan-4-yl α-L-fucopyranoside or 2'-O-fucosyllactose) and acceptor (10-500 mmol, donor acceptor ratio is 5:1 to 1:5) was incubated in degassed incubation buffer at a pH range from 5.0 to 9.0) with recombinant α-fucosidase, α-transfucosidase or α-fucosynthase. The reaction mixture was stirred for 24 hours at a temperature range from 20 to 70° C. Samples were taken at different times of the reaction, the reaction was stopped by the addition of 1M $NaHCO_3$-solution at pH=10 and analyzed by TLC and/or HPLC. After completion, the enzyme was denatured and centrifuged. The resulting solution was evaporated under reduced pressure. After lyophilisation, the dry residue was dissolved in water and purified by biogel chromatography (P-2 Biogel, 16×900 mm) with water or by reverse phase chromatography. The yields vary between 2.5-85%.

Recombinant Enzymes Used and Tested in this Set of Transfucosylation Reactions:

P25 from *Thermotoga Maritima* (see seq. ID 1) containing mutations G226S Y237H T264A L322P;

M3 from *Thermotoga Maritima* (see seq. ID 1) containing mutations Y237H Y267F L322P.

These transfucosidases were produced in *E. coli* as reported in G. Osanjo et al. *Biochemistry* 46, 1022 (2007). Purified transfucosidases P25 and M3 are stored at −20° C. or +4° C., respectively.

Optimal buffer for the enzymes: 50 mM sodium citrate/phosphate buffer and 150 mM NaCl, pH=5.5.

Optimum temperature: 60° C. (except for α-L-fucosyl fluoride acceptor, where the temperature is 35° C.).

LC-MS Conditions:
Instrument: AB Sciex API 2000 tandem MS
Ionization mode: electrospray in positive mode
Scan type: Q1MS
Sample insertion mode: HPLC
Column: Phenomenex HILIC 250×4.6 mm
Flow: isocratic (water-acetonitrile 22:78)
Flow rate: 1 ml/min
Injected volume: 5 μl a) acceptor: Galβ1-4Glcβ1-O-Bn
donor: p-nitrophenyl α-L-fucopyranoside, α-L-fucosyl fluoride or 2,5-dimethyl-3-oxo-(2H)-furan-4-yl α-L-fucopyranoside
product: Fucα1-2Galβ1-4Glcβ1-O-Bn (identified by comparison to the standard sample made by chemical means from 2'-O-fucosyllactose)

Characteristic $^1$H NMR peaks (DMSO-$d_6$) δ: 7.41-7.25 (m, 5H, aromatic), 5.20 (d, 1H, $J_{1'',2''}$=2 Hz, H-1'), 4.82 and 4.59 (ABq, 2H, $J_{gem}$=12.3 Hz, —$CH_2$Ph), 4.32 (d, 1H, $J_{1',2'}$=7.31 Hz, H-1'), 4.28 (d, 1H, $J_{1,2}$=7.79 Hz, H-1), 1.05 (d, 1H, $J_{5'',6''}$=6.43 Hz, H-6").

$^{13}$C NMR (DMSO-$d_6$) δ: 137.97, 128.15, 128.15, 127.58, 127.58 and 127.43 (aromatic), 101.86, 100.94 and 100.20 (C-1, C-1' and C-1"), 77.68, 76.78, 75.36, 75.33, 74.70, 73.79, 73.45, 71.60, 69.72, 69.69, 68.74, 68.20, 66.38, 60.23 and 59.81 (C-2, C-3, C-4, C-5, C-6, C-2', C-3', C-4', C-5', C-6', C-2", C-3", C-4", C-5" and $\underline{C}H_2$Ph), 16.47 (C-6").

b) acceptor: Galβ1-4Glcβ1-O—$CH_2$-(4-$NO_2$-Ph)
donor: p-nitrophenyl α-L-fucopyranoside or 2,5-dimethyl-3-oxo-(2H)-furan-4-yl α-L-fucopyranoside
product: Fucα1-2Galβ1-4Glcβ1-O—$CH_2$-(4-$NO_2$-Ph) (identified by comparison to the standard sample made by chemical means from 2'-O-fucosyllactose)

Characteristic $^1$H NMR peaks (DMSO-$d_6$) δ: 8.20 and 7.68 (each d, 4H, aromatic), 5.04 (d, 1H, $J_{1'',2''}$=2 Hz, H-1"), 4.97 and 4.76 (ABq, 2H, $J_{gem}$=12.3 Hz, —$CH_2$Ph), 4.40 (d, 1H, $J_{1',2'}$=9.53 Hz, H-1'), 4.32 (d, 1H, $J_{1,2}$=8.04 Hz, H-1), 1.04 (d, 1H, $J_{5'',6''}$=6.43 Hz, H-6").

$^{13}$C NMR (DMSO-$d_6$) δ: 162.38, 147.68, 127.95, 127.95, 123.33 and 123.33 (aromatic), 102.18, 100.95 and 100.18 (C-1, C-1' and C-1"), 77.62, 76.74, 75.36, 75.36, 74.61, 73.78, 73.45, 71.59, 69.67, 68.74, 68.67, 68.21, 66.38, 60.22 and 59.77 (C-2, C-3, C-4, C-5, C-6, C-2', C-3', C-4', C-5', C-6', C-2", C-3", C-4", C-5" and $\underline{C}H_2$Ph), 16.45 (C-6").

c) acceptor: Galβ1-3GlcNAcβ1-3Galβ1-4Glcβ1-O-Bn
donor: α-L-fucosyl fluoride, 2'-O-fucosyllactose or 2,5-dimethyl-3-oxo-(2H)-furan-4-yl α-L-fucopyranoside
product: monofucosylated Galβ1-3GlcNAcβ1-3Galβ1-4Glcβ1-O-Bn, correct molecular mass was confirmed by LC-MS (944 $[M+H]^+$, 961 $[M+NH_4]^+$, 966 $[M+Na]^+$)

d) acceptor: Galβ1-4GlcNAcβ1-3Galβ1-4Glcβ1-O-Bn
donor: α-L-fucosyl fluoride, 2'-O-fucosyllactose or 2,5-dimethyl-3-oxo-(2H)-furan-4-yl α-L-fucopyranoside
product: mono fucosylated Galβ1-4GlcNAcβ1-3Galβ1-4Glcβ1-O-Bn, correct molecular mass was confirmed by LC-MS (944 $[M+H]^+$, 961 $[M+NH_4]^+$, 966 $[M+Na]^+$)

Example 12

Manufacture of Acceptor Benzyl/Substituted Benzyl Glycosides

A) Benzyl/Substituted Benzyl Lactosides

A1) General procedure: lactose (5 g, 14.6 mmol) and TsOH.$H_2$O (0.2 g, 1.05 mmol) were added in one portion to a mixture of DMF (20 ml) and benzaldehyde dimethyl acetal (5.5 ml, 35.4 mmol, 2.4 eq.) at room temperature. The reaction mixture was vigorously stirred at 70° C. under exclusion of humidity for 1 hour. After cooling triethyl amine (0.15 ml) was added then the volatile components (MeOH, triethyl amine, remaining benzaldehyde dimethyl acetal) were removed in vacuo. To the reaction mixture the benzyl bromide derivative (1.5 eq.)—predissolved in 5-10 ml of DMF, if the reagent is a solid—was added and the mixture was cooled to 0° C. for 20 min. Still under cooling NaH (0.8 g of a 55% dispersion in mineral oil, 1.3 eq.) was added in one portion, and the mixture was stirred under cooling until the hydrogen formation stopped then at room temperature for 2-3 hours. Methanol (2 ml) was added carefully and the reaction was stirred for a further 5 min. The reaction mixture was portioned between 100 ml of DCM and 100 ml of water and extracted. The water layer was back-extracted twice with 100 ml of DCM. The combined organic phases were evaporated; the residue was dissolved in 100 ml of acetonitrile and extracted with 100 ml of hexane. The acetonitrile was distilled off and the residue was taken up in isopropanol (10 ml) and isopropyl ether (50 ml) at 50° C. The clear solution was cooled to −20° C. for between 2-12 hours. The crystals obtained were filtered off and washed twice with TBME and dried. Recrystallization can be carried out from a mixture of TBME (~50 ml) and ethanol (~20 ml).

4-Chlorobenzyl 4',6'-O-benzylidene-β-lactoside

Yield: 1.71 g

4-Methylbenzyl 4',6'-O-benzylidene-β-lactoside

Yield: 3.20 g

3-Phenylbenzyl 4',6'-O-benzylidene-β-lactoside

Yield: 2.70 g

2-Naphthylmethyl 4',6'-O-benzylidene-β-lactoside

Yield: 1.77 g

B1) To a mixture of one of the above benzylidene acetals (500 mg) in methanol (10 ml) and water (0.5 ml) TFA was added at room temperature and the reaction mixture was stirred for 2-4 hours under exclusion of humidity then evaporated. The remaining material was co-evaporated with ethanol 3-4 times giving a crude solid, which, after drying, can be recrystallized from a mixture of methanol (~10-35 ml) and water (~O-2 mL).

4-Chlorobenzyl β-lactoside

Yield: 333 mg
$^{13}$C-NMR (75.1 MHz, D$_2$O): δ=135.25, 133.67, 130.30, 128.70, 103.00, 101.13, 78.39, 75.44, 74.89, 74.49, 72.88, 72.58, 71.03, 70.83, 68.62, 61.11, 60.13.

4-Methylbenzyl β-lactoside

Yield: 439 mg
$^{13}$C-NMR (75.1 MHz, D$_2$O): δ=138.91, 133.50, 129.37, 129.07, 103.01, 100.96, 78.43, 75.44, 74.87, 74.52, 72.90, 72.59, 71.47, 71.03, 68.63, 61.11, 60.17, 20.34.

3-Phenylbenzyl β-lactoside

Yield: 438 mg
$^{13}$C-NMR (75.1 MHz, d$_6$-DMSO/d$_4$-MeOH/D$_2$O 8:1:1): δ=140.29, 140.24, 138.88, 129.13, 129.02, 127.66, 126.88, 126.83, 126.03, 125.90, 103.95, 102.03, 80.76, 75.65, 75.07, 75.00, 73.34, 73.28, 70.66, 69.81, 68.27, 60.56.

2-Naphthylmethyl β-lactoside

Yield: 378 mg
$^{13}$C-NMR (75.1 MHz, D$_2$O/d$_6$-DMSO): δ=134.96, 133.24, 133.12, 128.59, 128.31, 128.08, 127.46, 126.98, 126.90, 126.79, 103.26, 101.59, 78.89, 75.62, 75.09, 74.81, 73.14, 72.81, 71.33, 71.14, 68.75, 61.22, 60.39.

B) Galβ1-3GlcNAcβ1-3Galβ1-4Glcβ1-O-Bn (1-O-benzyl-β-LNT) can be prepared according to A. Malleron et al. *Carbohydr. Res.* 341, 29 (2006).

C) Galβ1-4GlcNAcβ1-3Galβ1-4Glcβ1-O-Bn (1-O-benzyl-β-LNnT) can be prepared according to WO 2011/100980.

Example 13

Manufacture of 2,5-dimethyl-3-oxo-(2H)-furan-4-yl α-L-fucopyranoside a) The solution of 2,3,4-tri-O-(4-methoxybenzyl)-L-fucopyranose trichloroacetimidate (a/β mixture, prepared from 85 mmol of 2,3,4-tri-O-(4-methoxybenzyl)-L-fucopyranose and trichloroacetonitrile in the presence of NaH in quantitative yield) in diethyl ether (100 ml) was added to a mixture of 2,5-dimethyl-4-hydroxy-3-oxo-(2H)-furan (85 mmol) and TMS-triflate (1.2 ml) in diethyl ether (200 ml) at −14° C. After 3 hours the cooling bath was removed and the stirring continued for 1 hour. The reaction mixture was diluted with ethyl acetate and extracted with sat. NaHCO$_3$-solution (3×150 ml) and brine (150 ml). The organic phase was dried over Na$_2$SO$_4$ and evaporated. The resulting syrup was purified by column chromatography yielding 23.27 g of 2,5-dimethyl-3-oxo-(2H)-furan-4-yl 2,3,4-tri-O-(4-methoxybenzyl)-α-L-fucopyranoside as a thick yellow syrup in a 1:1 mixture of diastereoisomers. Selected NMR chemical shifts in CDCl$_3$: anomeric protons: 5.32 and 5.57 ppm, J$_{1,2}$=3.4 Hz; anomeric carbons: 113.81 and 113.95 Hz.

b) A suspension of the above product and Pd on charcoal (12.5 g) in ethyl acetate (1 l) was stirred at room temperature for 6 hours under H$_2$. The catalyst was filtered off and washed with ethyl acetate. The combined filtrate was evaporated to a solid mass which was suspended in ethyl acetate and allowed to stand at 5° C. for overnight. The crystalline material was filtered off and dried. The mother liquor was subjected to column chromatography. The combined products gave 5.50 g of 2,5-dimethyl-3-oxo-(2H)-furan-4-yl α-L-fucopyranoside as white solid in 1:1 mixture of diastereoisomers. Selected NMR chemical shifts in DMSO-d$_6$: anomeric protons: 5.07 and 5.52 ppm, J$_{1,2}$=2.6 Hz; anomeric carbons: 100.19 and 101.03 Hz. Purity by GC (after silylation): 98.9%.

The invention claimed is:

1. A method for making a mixture of human milk oligosaccharides (HMOs) or derivatives or precursors thereof, the method comprising the steps of
   a) providing at least one donor selected from the group consisting of compounds of any of formulae 5 to 10

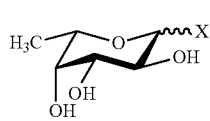

5

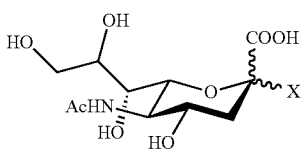

6

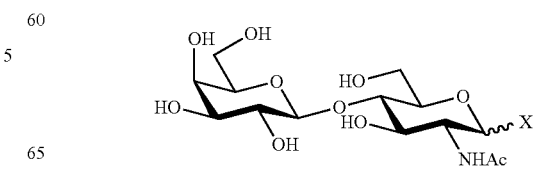

7

-continued

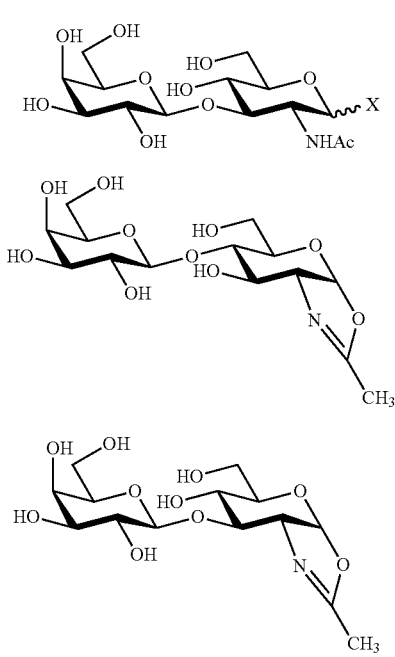

and salts thereof,
wherein X is selected from the group consisting of azide, fluoro, optionally substituted phenoxy, optionally substituted pyridinyloxy, group A, group B, group C and group D

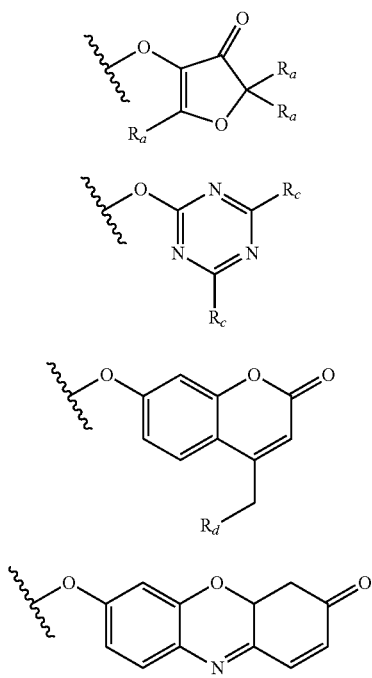

wherein $R_a$ is independently H or alkyl, or two vicinal $R_a$ groups represent a=C($R_b$)$_2$ group, wherein $R_b$ is independently H or alkyl, $R_c$ is independently selected from the group consisting of alkoxy, amino, alkylamino and dialkylamino, $R_d$ is selected from the group consisting of H, alkyl and —C(=O)$R_e$, wherein $R_e$ is OH, alkoxy, amino, alkylamino, dialkylamino, hydrazino, alkylhydrazino, dialkylhydrazino or trialkylhydrazino;

b) providing at least one acceptor selected from the group of compounds consisting of:
lactose
lactose derivatives of the following formula:

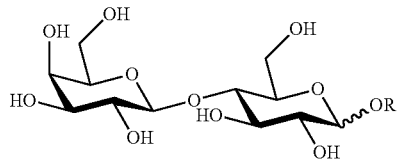

wherein R is a group removable by hydrogenolysis, LNT:

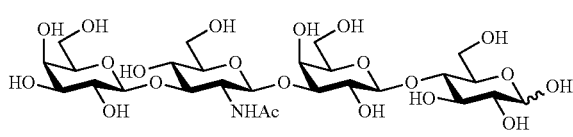

LNT derivatives of the formula:

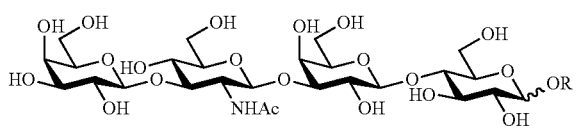

wherein R is a group removable by hydrogenolysis, or salts thereof
LNnT:

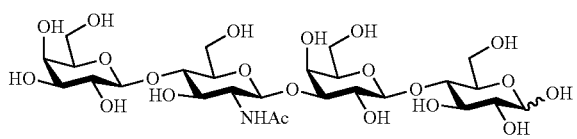

LNnT derivatives of the formula:

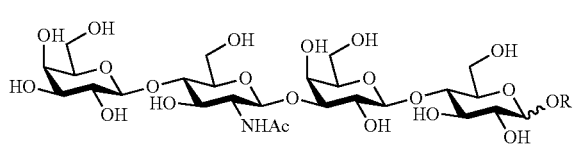

wherein R is a group removable by hydrogenolysis, or salts thereof c) providing at least one enzyme comprising a transglycosidase activity and/or a glycosynthase activity;

d) preparing a mixture of the at least one donor, at least one acceptor and at least one enzyme provided in steps a), b) and c);

e) incubating the mixture prepared according to step d);

in the case where a single HMO or derivative or precursor thereof is made as a result of step e), repeating at least one of the steps a) to c), then repeating step d) and step e);

g) optionally: repeating at least one of the steps a) to c), then repeating step d) and step e) with the mixture obtained according to step e) or f);

h) optionally subjecting the mixture obtained as a result of step e), f) or g) to a hydrogenolysis reaction.

2. The method according to claim 1, wherein two, three, four, five, one to five, three to ten, or five to ten different donors are provided in step a).

3. The method according to claim 1, wherein two, three, four, five, one to five, three to ten, or five to ten different acceptors are provided in step b).

4. The method according to claim 1, wherein two, three, four, five, one to five, three to ten, or five to ten different enzymes are provided in step c).

5. The method according to claim 1, wherein the donors, acceptors, or enzymes are added simultaneously or sequentially.

6. The method according to claim 1, wherein
the donors are selected from compounds according to formulae 5 to 8, wherein X is optionally substituted 4-nitrophenoxy, group A, group B, group C, or from compounds 9 and 10, when the enzyme selected in step c) has transglycosidase activity; and/or
the donors are selected dependent on the activity of the selected glycosynthase(s) from compounds according to formulae 5 to 8, wherein X is azide or fluoro when the enzyme provided in step c) has glycosynthase activity.

7. The method according to claim 1, wherein the donors are selected from compounds according to formulae 5 to 8, wherein X is 4-nitrophenoxy, 2,4-dinitrophenoxy, 2-chloro-4-nitrophenoxy, 2,5-dimethyl-3-oxo-(2H)-furan-4-yloxy, 2-ethyl-5-methyl-3-oxo-(2H)-furan-4-yloxy, 5-ethyl-2-methyl-3-oxo-(2H)-furan-4-yloxy, 4,6-dimethoxy-1,3,5-triazin-2-yloxy, 4,6-diethoxy-1,3,5-triazin-2-yloxy, or 4-methylumbelliferyloxy.

8. The method according to claim 1, wherein the at least one enzyme comprising transglycosidase activity and/or glycosynthase activity is an enzyme comprising a trans-fucosidase, trans-sialidase, trans-lacto-N-biosidase and/or trans-N-acetyllactosaminidase activity.

9. The method according to claim 1, wherein incubation leads to a mixture of human milk oligosaccharides or derivatives or precursors thereof, wherein at least one compound of the mixture is defined according to
compounds of general formula 1 and salts thereof

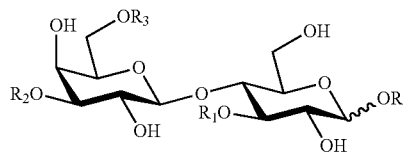

general formula 1 wherein
R is a group removable by hydrogenolysis,
$R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue;
compounds of general formula 2 and salts thereof

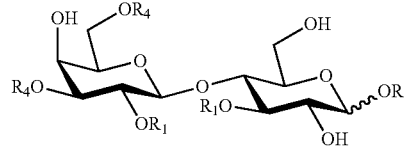

general formula 2 wherein
R is a group removable by hydrogenolysis,
$R_1$ independently of each other is fucosyl or H
$R_4$ independently of each other is sialyl or H,
with the proviso that at least one $R_1$ or $R_4$ is not H;
compounds of general formula 3 and salts thereof

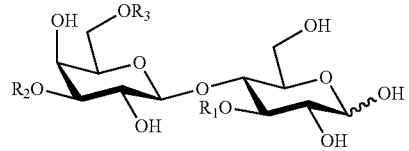

general formula 3 wherein
$R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue; and/or
compounds of general formula 4 and salts thereof

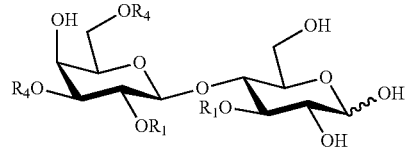

general formula 4 wherein
$R_1$ independently of each other is fucosyl or H
$R_4$ independently of each other is sialyl or H
with the proviso that at least one $R_1$ or $R_4$ is not H.

10. The method according to claim 9, wherein compounds of formulae 1 and 2 are further characterized by general formulae 1a, 1b or 2 or salts thereof

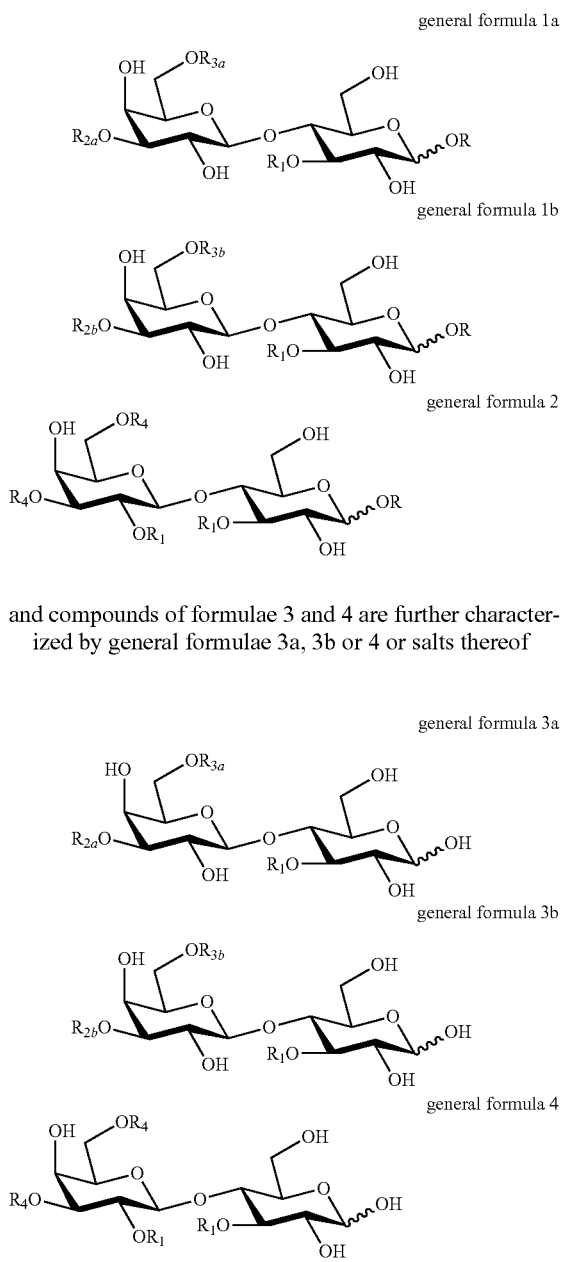

general formula 1a general formula 1b general formula 2 and compounds of formulae 3 and 4 are further characterized by general formulae 3a, 3b or 4 or salts thereof general formula 3a general formula 3b general formula 4 wherein

R, $R_1$ and $R_4$ are as defined in claim 9, $R_{2a}$ is N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue, $R_{3a}$ is H or N-acetyl-lactosaminyl group optionally substituted with a lacto-N-biosyl group; any N-acetyl-lactosaminyl and lacto-N-biosyl group can be substituted with one or more sialyl and/or fucosyl residue, $R_{2b}$ is lacto-N-biosyl group optionally substituted with sialyl and/or fucosyl residue, and $R_{3b}$ is H or N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue.

11. The method according to claim 10, wherein
the N-acetyl-lactosaminyl group in the glycosyl residue of $R_{2a}$ in general formula 1a or 3a is attached to another N-acetyl-lactosaminyl group with 1-3 interglycosidic linkage,
the lacto-N-biosyl group in the glycosyl residue of $R_{2a}$ in general formula 1a or 3a is attached to the N-acetyl-lactosaminyl group with 1-3 interglycosidic linkage,
the lacto-N-biosyl group in the glycosyl residue of $R_{3a}$ in general formula 1a or 3a is attached to the N-acetyl-lactosaminyl group with 1-3 interglycosidic linkage,
the N-acetyl-lactosaminyl group in the glycosyl residue of $R_{3b}$ in general formula 1b or 3b is attached to the another N-acetyl-lactosaminyl group with 1-3 or 1-6 interglycosidic linkage,
the lacto-N-biosyl group in the glycosyl residue of $R_{3b}$ in general formula 1b or 3b is attached to the N-acetyl-lactosaminyl group with 1-3 interglycosidic linkage.

12. The method according to claim 10, wherein general formula 1a represents the R-glycosides of lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, general formula 1b represents the R-glycosides of lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue, general formula 3a represents lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 3b represents lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

13. The method according to claim 9, wherein
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

14. The method according to claim 9, wherein the compounds are selected from the group consisting of: R-glycosides of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, and salts thereof.

15. The method according to claim 9, wherein the compound according to general formula 1 or general formula 2 is the beta anomer with respect to the OR group.

16. The method according to claim 9, wherein the compounds are selected from the group consisting of: 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II, and salts thereof.

17. The method according to claim 1, wherein the compounds obtained in the incubation step are subjected to a hydrogenolysis reaction.

18. The method according to claim 1, wherein the compounds obtained in the incubation or hydrogenolysis step are subsequently purified.

19. The method according to claim 1, further comprising a step of spray-drying the compounds obtained in step e), f), g) or h).

20. The method of claim 1, further comprising addition of the compounds obtained in the incubation or hydrogenolysis step to a consumable product.

21. The method of claim 20, further comprising the addition of pharmaceutically acceptable carriers and/or the addition of prebiotics to the compounds obtained in the incubation or hydrogenolysis step.

22. The method according to claim 8, wherein the at least one enzyme comprising transglycosidase activity and/or glycosynthase activity is an enzyme comprising an α-trans-fucosidase, α-trans-sialidase, β-trans-lacto-N-biosidase and/or β-trans-N-acetyllactosaminidase activity.

23. The method according to claim 15, wherein R is benzyl.

24. The method according to claim 18, wherein purification is via crystallization or precipitation.

25. The method according to claim 20, wherein the consumable product is at least one of a pharmaceutical or nutritional formulation.

* * * * *